United States Patent
Shin et al.

(10) Patent No.: US 10,700,286 B2
(45) Date of Patent: Jun. 30, 2020

(54) ORGANIC COMPOUND AND ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Chang Ju Shin, Suwon-si (KR); Jinseok Hong, Suwon-si (KR); Dong Wan Ryu, Suwon-si (KR); Eun Sun Yu, Suwon-si (KR); Hanill Lee, Suwon-si (KR); Chunkeun Jang, Suwon-si (KR); Sung-Hyun Jung, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/417,454

(22) Filed: Jan. 27, 2017

(65) Prior Publication Data

US 2017/0279053 A1    Sep. 28, 2017

(30) Foreign Application Priority Data

Mar. 23, 2016    (KR) .................... 10-2016-0034769

(51) Int. Cl.
| | | |
|---|---|---|
| *H01L 51/50* | (2006.01) | |
| *H01L 51/00* | (2006.01) | |
| *C07D 307/77* | (2006.01) | |
| *C07D 333/50* | (2006.01) | |
| *H01L 51/52* | (2006.01) | |

(52) U.S. Cl.
CPC ........ *H01L 51/0061* (2013.01); *C07D 307/77* (2013.01); *C07D 333/50* (2013.01); *H01L 51/0059* (2013.01); *H01L 51/0073* (2013.01); *H01L 51/0074* (2013.01); *H01L 51/5012* (2013.01); *H01L 51/5064* (2013.01); *H01L 51/5206* (2013.01); *H01L 51/5221* (2013.01)

(58) Field of Classification Search
None
See application file for complete search history.

(56) References Cited

U.S. PATENT DOCUMENTS

| | | | |
|---|---|---|---|
| 2004/0164292 A1 | 8/2004 | Tung et al. | |
| 2014/0319494 A1 | 10/2014 | Miyashita et al. | |
| 2015/0255726 A1 | 9/2015 | Kawamura et al. | |
| 2016/0133850 A1* | 5/2016 | Matsuura | H01L 51/5064 257/40 |

(Continued)

FOREIGN PATENT DOCUMENTS

| | | |
|---|---|---|
| CN | 103058987 A | 4/2013 |
| CN | 104638202 A | 5/2015 |

(Continued)

OTHER PUBLICATIONS

Office Action dated Mar. 28, 2019, and/or the accompanying Search Report dated Mar. 20, 2019, of the corresponding Chinese Patent Application No. 201710158941.1.

(Continued)

*Primary Examiner* — Gregory D Clark
(74) *Attorney, Agent, or Firm* — Lee IP Law, P.C.

(57) ABSTRACT

An organic compound represented by Chemical Formula 1, an organic optoelectric device including the organic compound, and a display device including the organic optoelectric device are disclosed.

11 Claims, 3 Drawing Sheets

(56) References Cited

U.S. PATENT DOCUMENTS

2017/0125689 A1* 5/2017 Lee ...................... C07D 333/76

FOREIGN PATENT DOCUMENTS

| | | | |
|---|---|---|---|
| CN | 104649955 A | | 5/2015 |
| CN | 107849000 | | 3/2018 |
| KR | 10-2011-0127784 A | | 11/2011 |
| KR | 10-2012-0116881 A | | 10/2012 |
| KR | 10-2011-0107051 | * | 4/2013 ............. C09K 11/06 |
| KR | 10-2013-0042901 A | | 4/2013 |
| KR | 1020110107051 | * | 4/2013 |
| KR | 10-2013-0110347 A | | 10/2013 |
| KR | 10-2014-0015305 A | | 2/2014 |
| KR | 10-2014-0021293 A | | 2/2014 |
| KR | 10-2014-0043224 A | | 4/2014 |
| KR | 10-2014-0055137 A | | 5/2014 |
| KR | 10-2014-0067914 A | | 6/2014 |
| KR | 10-2014-0079595 A | | 6/2014 |
| KR | 10-2014-0102089 A | | 8/2014 |
| KR | 10-2014-0103436 A | | 8/2014 |
| KR | 10-2014-0147374 A | | 12/2014 |
| KR | 10-2015-0022898 A | | 3/2015 |
| KR | 10-2015-0052705 A | | 5/2015 |
| KR | 10-2015-0079664 A | | 7/2015 |
| KR | 10-2015-0097703 A | | 8/2015 |
| KR | 10-2015-0098631 A | | 8/2015 |
| KR | 10-1551526 B1 | | 9/2015 |
| KR | 10-2016-0055675 A | | 5/2016 |
| KR | 10-2017-0030289 A | | 3/2017 |
| WO | WO 2015/174639 A1 | | 11/2015 |
| WO | WO 2015/182887 A1 | | 12/2015 |
| WO | WO 2015/194791 A2 | | 12/2015 |

OTHER PUBLICATIONS

Chinese Office Action dated Feb. 6, 2020.

* cited by examiner

ORGANIC COMPOUND AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0034769 filed in the Korean Intellectual Property Office on Mar. 23, 2016, the entire contents of which are incorporated herein by reference.

BACKGROUND

1. Field

An organic compound, an organic optoelectric device, and a display device are disclosed.

2. Description of the Related Art

An organic optoelectric device is a device that converts electrical energy into photoenergy, and vice versa.

An organic optoelectric device may be classified as follows in accordance with its driving principles. One is an optoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectric device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode.

Performance of an organic light emitting diode may be affected by characteristics of the organic layer, and among them, may be mainly affected by characteristics of an organic material of the organic layer. Particularly, development for an organic material being capable of increasing hole and electron mobility and simultaneously increasing electrochemical stability is needed so that the organic light emitting diode may be applied to a large-size flat panel display.

SUMMARY

An embodiment provides an organic compound capable of realizing an organic optoelectric device having high efficiency and a long life-span.

Another embodiment provides an organic optoelectric device including the organic compound.

Yet another embodiment provides a display device including the organic optoelectric device.

According to an embodiment, an organic compound represented by Chemical Formula 1 is provided.

[Chemical Formula 1]

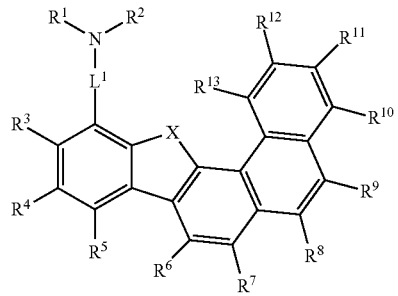

In Chemical Formula 1,

X is O or S, $L^1$ is a single bond, a substituted or unsubstituted C6 to C30 arylene group, or a substituted or unsubstituted C2 to C30 heterocyclic group, $R^1$ and $R^2$ are independently a substituted or unsubstituted C1 to C20 alkyl group, a substituted or unsubstituted C6 to C30 aryl group, a substituted or unsubstituted C2 to C30 heterocyclic group, a substituted or unsubstituted C3 to C40 silyl group, or a combination thereof, and $R^3$ to $R^{13}$ are independently hydrogen, deuterium, a halogen, a cyano group, a hydroxyl group, an amino group, a substituted or unsubstituted C1 to C20 amine group, a nitro group, a substituted or unsubstituted C1 to C20 alkyl group, a substituted or unsubstituted C6 to C30 aryl group, a substituted or unsubstituted C1 to C20 alkoxy group, a substituted or unsubstituted C6 to C20 aryloxy group, a substituted or unsubstituted C2 to C30 heterocyclic group, a substituted or unsubstituted C3 to C40 silyl group, or a combination thereof.

Another embodiment provides an organic optoelectric device including an anode and a cathode facing each other and at least one organic layer between the anode and the cathode, wherein the organic layer includes the organic compound.

Yet another embodiment provides a display device including the organic optoelectric device.

An organic optoelectric device having high efficiency and a long life-span may be realized.

DETAILED DESCRIPTION

Figure 1:
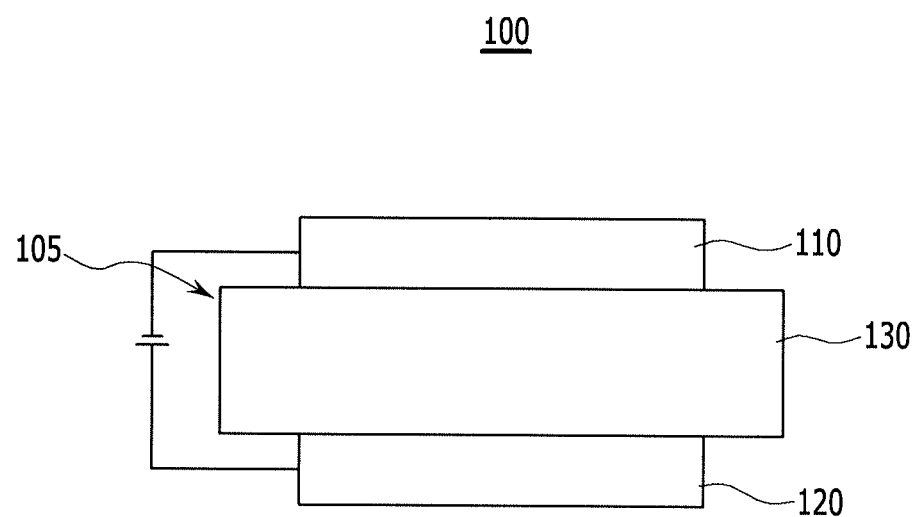
FIGS. 1 to 3 are cross-sectional views showing organic light emitting diodes according to embodiments.

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to one substituted with deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heterocyclic group, a C1 to C20 alkoxy group, a fluoro group, a C1 to C10 trifluoroalkyl group such as a trifluoromethyl group, or a cyano group, instead of at least one hydrogen of a substituent or a compound.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heterocyclic group, C1 to C20 alkoxy group, fluoro group, C1 to C10 trifluoroalkyl group such as trifluoromethyl group and the like, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one heteroatom selected from the group consisting of N, O, S, P, and Si, and remaining carbons in one functional group.

In the present specification, "an aryl group" refers to a group having at least one hydrocarbon ring aromatic moiety, and broadly hydrocarbon ring aromatic moieties linked by a single bond and a non-aromatic fused ring including hydrocarbon ring aromatic moieties fused directly or indirectly. An aryl group may be monocyclic, polycyclic or fused ring polycyclic (i.e., rings sharing adjacent pairs of carbon atoms) functional group.

In the present specification, "a heterocyclic group" includes a heteroaryl group, and a cyclic group including at least one heteroatom selected from N, O, S, P, and Si instead of carbon (C) of a cyclic compound such as an aryl group, a cycloalkyl group, a fused ring or a combination thereof. When the heterocyclic group is a fused ring, each or entire ring of the heterocyclic group may include at least one heteroatom.

More specifically, a substituted or unsubstituted C6 to C30 aryl group and/or a substituted or unsubstituted C2 to C30 heterocyclic group refer to a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, a combination thereof, or a combined fused ring of the foregoing groups, but is not limited thereto.

In the present specification, a substituted or unsubstituted arylene group or a substituted or unsubstituted heteroarylene group refer to a substituted or unsubstituted aryl group or a substituted or unsubstituted heteroaryl group which is defined above and has two linking points, for example, a substituted or unsubstituted phenylene group, a substituted or unsubstituted naphthylene group, a substituted or unsubstituted anthracenylene group, a substituted or unsubstituted phenanthrylene group, a substituted or unsubstituted naphthacenylene group, a substituted or unsubstituted pyrenylene group, a substituted or unsubstituted biphenylene group, a substituted or unsubstituted terphenylene group, a substituted or unsubstituted quaterphenylene group, a substituted or unsubstituted chrysenylene group, a substituted or unsubstituted triphenylenylene group, a substituted or unsubstituted perylenylene group, a substituted or unsubstituted indenylene group, a substituted or unsubstituted furanylene group, a substituted or unsubstituted thiophenylene group, a substituted or unsubstituted pyrrolylene group, a substituted or unsubstituted pyrazolylene group, a substituted or unsubstituted iimidazolylene group, a substituted or unsubstituted triazolylene group, a substituted or unsubstituted oxazolylene group, a substituted or unsubstituted thiazolylene group, a substituted or unsubstituted oxadiazolylene group, a substituted or unsubstituted thiadiazolylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted benzofuranylene group, a substituted or unsubstituted benzothiophenylene group, a substituted or unsubstituted benzimidazolylene group, a substituted or unsubstituted indolylene group, a substituted or unsubstituted quinolinylene group, a substituted or unsubstituted isoquinolinylene group, a substituted or unsubstituted quinazolinylene group, a substituted or unsubstituted quinoxalinylene group, a substituted or unsubstituted naphthyridinylene group, a substituted or unsubstituted benzoxazinylene group, a substituted or unsubstituted benzthiazinylene group, a substituted or unsubstituted acridinylene group, a substituted or unsubstituted phenazinylene group, a substituted or unsubstituted phenothiazinylene group, a substituted or unsubstituted phenoxazinylene group, a substituted or unsubstituted fluorenylene group, a substituted or unsubstituted dibenzofuranylene group, a substituted or unsubstituted dibenzothiophenylene group, a substituted or unsubstituted carbazolylene group, a combination thereof, or a combined fused ring of the foregoing groups, but is not limited thereto.

In the specification, hole characteristics refer to an ability to donate an electron to form a hole when an electric field is applied and that a hole formed in the anode may be easily injected into the light-emitting layer, and a hole formed in a light-emitting layer may be easily transported into an anode and transported in the light-emitting layer due to conductive characteristics according to a highest occupied molecular orbital (HOMO) level.

In addition, electron characteristics refer to an ability to accept an electron when an electric field is applied and that an electron formed in a cathode may be easily injected into the light-emitting layer, and an electron formed in a light-emitting layer may be easily transported into a cathode and transported in the light-emitting layer due to conductive characteristics according to a lowest unoccupied molecular orbital (LUMO) level.

In the specification, an organic optoelectric device or an organic photoelectric display device refers to have the same meaning as an organic light emitting diode or an organic light emitting diode (OLED) display.

Hereinafter, an organic compound according to an embodiment is described.

An organic compound according to an embodiment is represented by Chemical Formula 1.

[Chemical Formula 1]

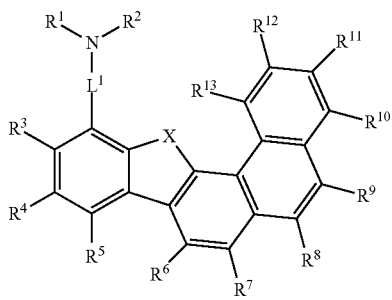

In Chemical Formula 1,

X is O or S, $L^1$ is a single bond, a substituted or unsubstituted C6 to C30 arylene group, or a substituted or unsubstituted C2 to C30 heterocyclic group, $R^1$ and $R^2$ are independently a substituted or unsubstituted C1 to C20 alkyl group, a substituted or unsubstituted C6 to C30 aryl group, a substituted or unsubstituted C2 to C30 heterocyclic group, a substituted or unsubstituted C3 to C40 silyl group, or a combination thereof, and $R^3$ to $R^{13}$ are independently hydrogen, deuterium, a halogen, a cyano group, a hydroxyl group, an amino group, a substituted or unsubstituted C1 to C20 amine group, a nitro group, a substituted or unsubstituted C1 to C20 alkyl group, a substituted or unsubstituted C6 to C30 aryl group, a substituted or unsubstituted C1 to C20 alkoxy group, a substituted or unsubstituted C6 to C20 aryloxy group, a substituted or unsubstituted C2 to C30 heterocyclic group, a substituted or unsubstituted C3 to C40 silyl group, or a combination thereof.

The organic compound represented by Chemical Formula 1 is an amine compound substituted with a fused ring having a heteroatom, and the amine compound is boned at an ortho position of a ring closest to the fused ring having the heteroatom.

In an organic light emitting diode, a layer (a hole transport layer (HTL), an electron transport layer (ETL)) neighboring an emission layer should have a higher Si energy level than the emission layer to increase luminous efficiency and a life-span, and particularly, the hole transport layer (HTL) should have a high LUMO energy level to effectively block electrons transported through the emission layer from the electron transport layer (ETL). The organic compound represented by Chemical Formula 1 is the amine compound bonded at the ortho position of a ring closest to the fused ring and thus has higher Si energy level and LUMO energy level than amine compounds bonded at other positions of the fused ring and accordingly, may increase efficiency and a life-span of the organic light emitting diode. In addition, the organic compound has the fused ring group and maintains a flat molecular structure and thus may have a large effect on increasing stability of a thin film and thus increasing the life-span.

Furthermore, the fused ring of the organic compound represented by Chemical Formula 1 has one more ring fused at a position of R' and R" compared with a fused ring represented by Chemical Formula A and thus may further increase the molecular flatness and maintain a stable thin film state during formation of an organic deposition film and resultantly have a large effect on realizing an organic light emitting diode having high efficiency and a long life-span and simultaneously, electrochemical and thermal stability under a low driving voltage.

[Chemical Formula A]

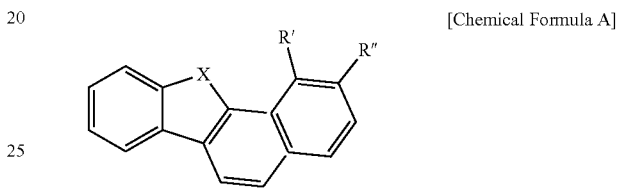

The organic compound represented by Chemical Formula 1 may be, for example represented by one selected from Chemical Formula 2-1 to Chemical Formula 2-4.

[Chemical Formula 2-1]

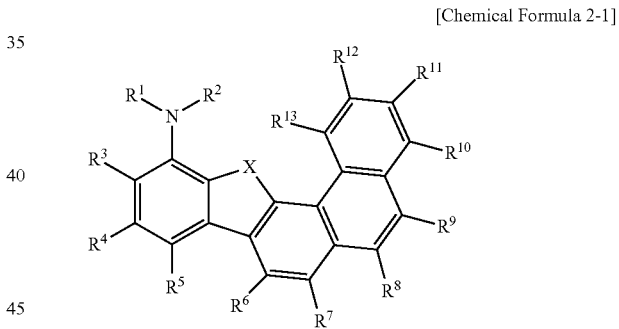

[Chemical Formula 2-2]

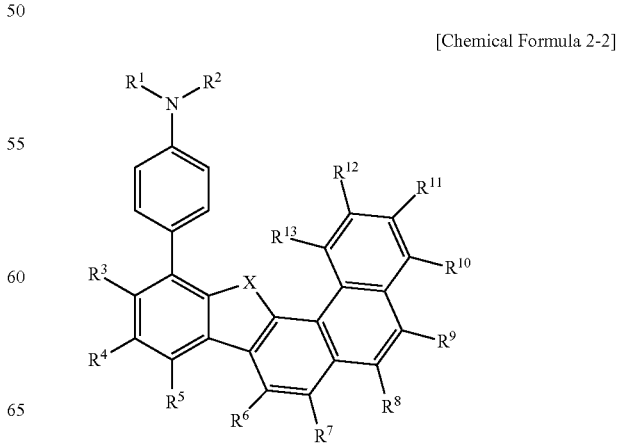

-continued

[Chemical Formula 2-3]

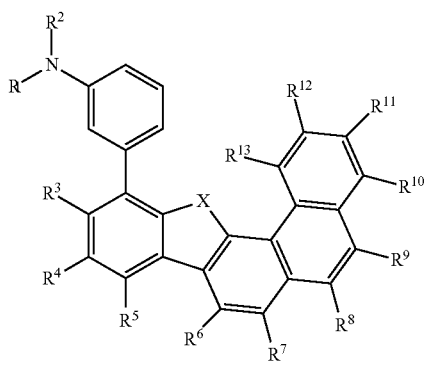

[Chemical Formula 2-4]

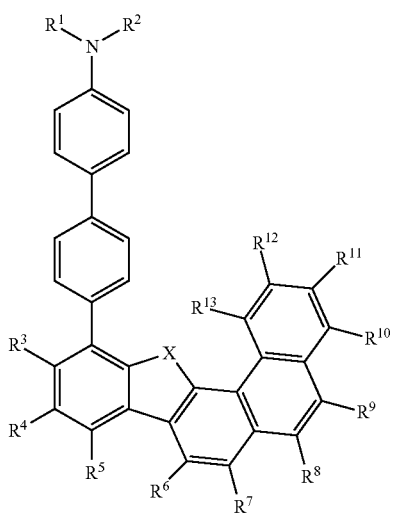

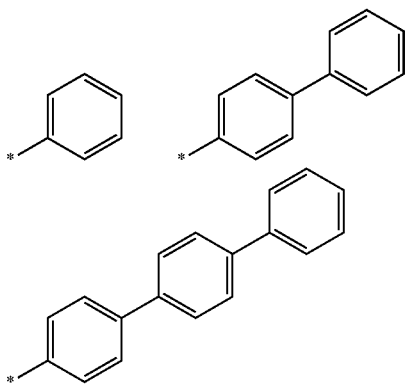

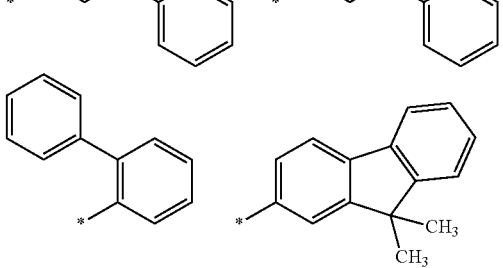

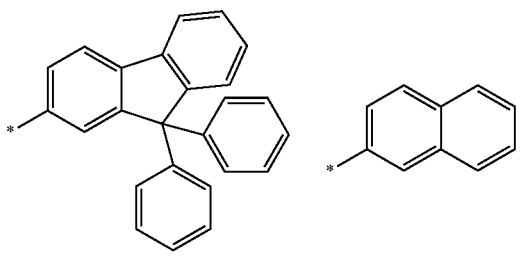

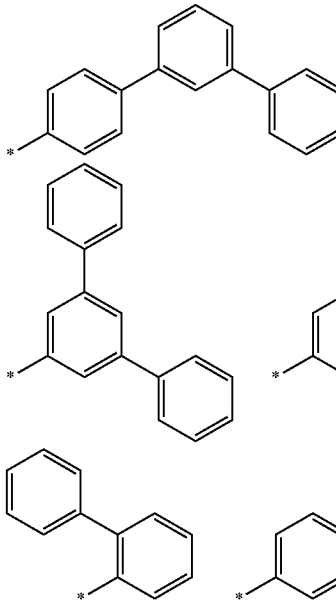

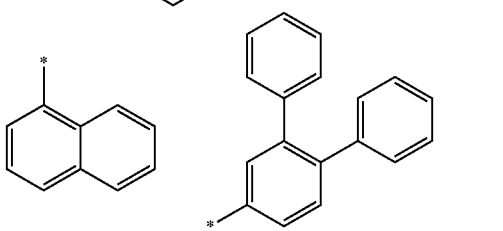

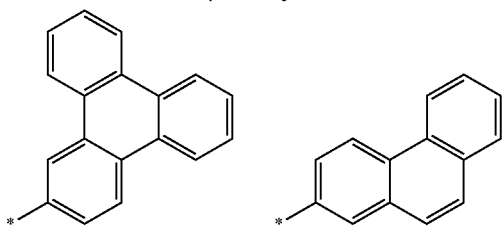

In Chemical Formula 2-1 to Chemical Formula 2-4,
X is O or S,
$R^1$ to $R^{13}$ are independently hydrogen, deuterium, a halogen, a cyano group, a hydroxyl group, an amino group, a substituted or unsubstituted C1 to C20 amine group, a nitro group, a substituted or unsubstituted C1 to C20 alkyl group, a substituted or unsubstituted C6 to C30 aryl group, a substituted or unsubstituted C1 to C20 alkoxy group, a substituted or unsubstituted C6 to C20 aryloxy group, a substituted or unsubstituted C2 to C30 heterocyclic group, a substituted or unsubstituted C3 to C40 silyl group, or a combination thereof.

The $R^1$ and $R^2$ may independently be a substituted or unsubstituted C6 to C30 aryl group or a substituted or unsubstituted (monovalent) C3 to C12 heterocyclic group.

For example, the $R^1$ and $R^2$ are independently a substituted or unsubstituted phenyl group, a substituted or unsubstituted biphenyl group, a substituted or unsubstituted triphenylene group, a substituted or unsubstituted terphenyl group, a substituted or unsubstituted fluorene group, a substituted or unsubstituted bisfluorene group, a substituted or unsubstituted naphthyl group, a substituted or unsubstituted isochrysene group, a substituted or unsubstituted anthracene group, a substituted or unsubstituted dibenzofuran group, a substituted or unsubstituted dibenzothiophenyl group, a combination thereof, or a fused ring of a combination thereof.

For example, the $R^1$ and $R^2$ may independently be one of groups of Group 1, but are not limited thereto.

-continued

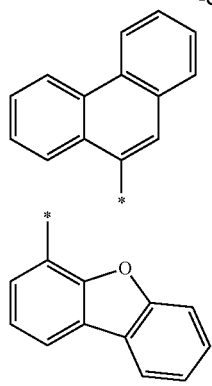

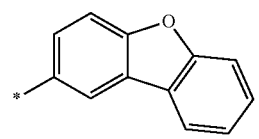

E-1 to Chemical Formula(CF) E-9, but is not limited thereto. Hereafter, "CF" means "Chemical Formula".

[CF A-1]

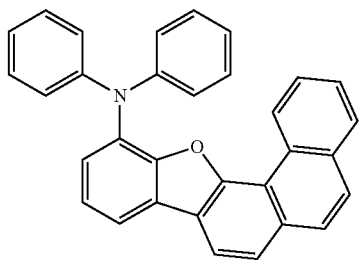

[CF A-2]

[CF A-3]

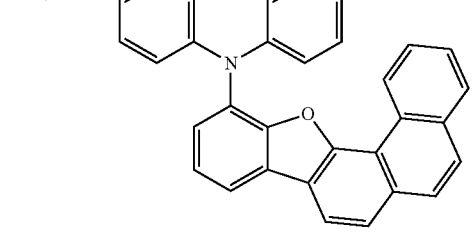

[CF A-4]

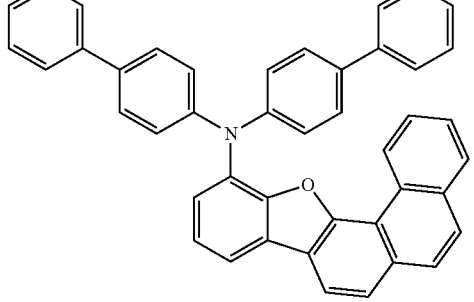

The organic compound represented by Chemical Formula 1 may be selected from Chemical Formula(CF) A-1 to Chemical Formula(CF) A-9, Chemical Formula(CF) B-1 to Chemical Formula(CF) B-93, Chemical Formula(CF) C-1 to Chemical Formula(CF) C-12, Chemical Formula(CF) D-1 to Chemical Formula(CF) D-9, and Chemical Formula(CF)

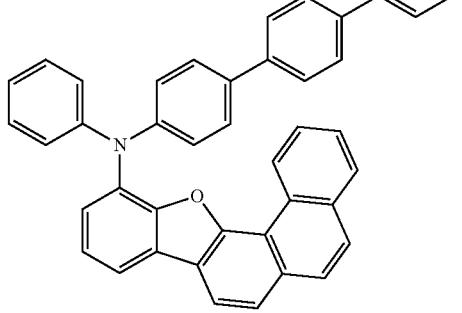

[CF A-5]
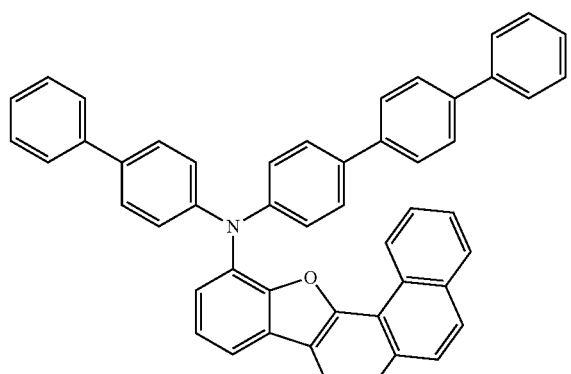
[CF A-6]
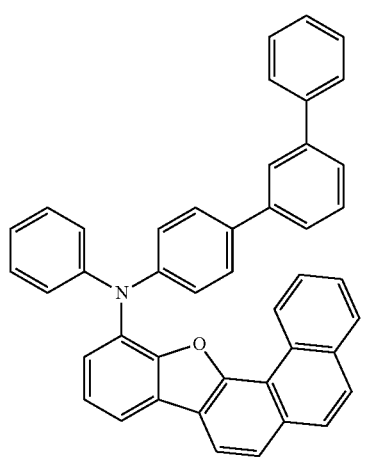
[CF A-7]
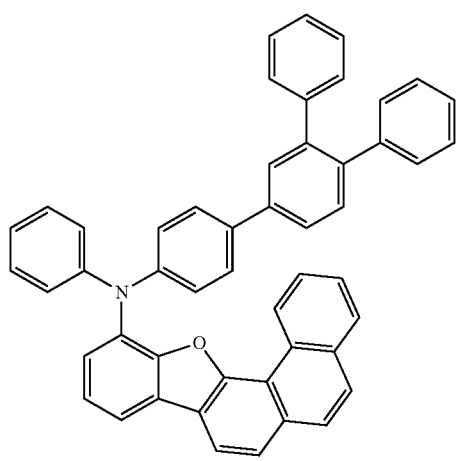
[CF A-8]
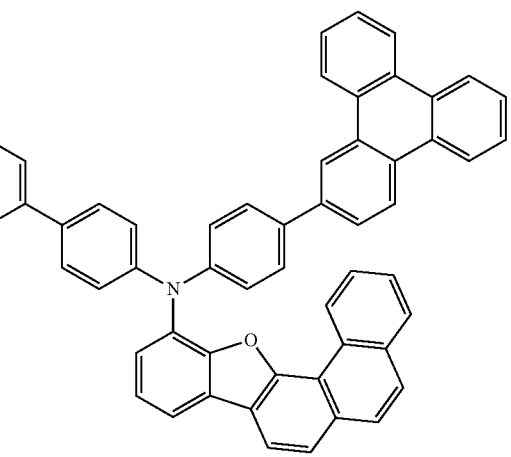
[CF A-9]
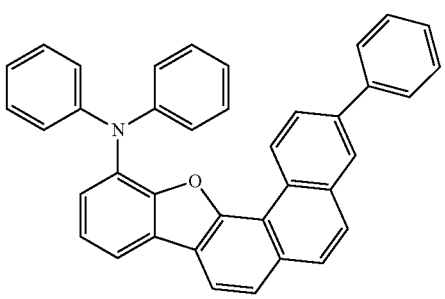
[CF B-1]
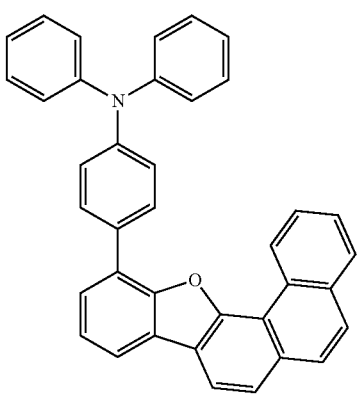
[CF B-2]
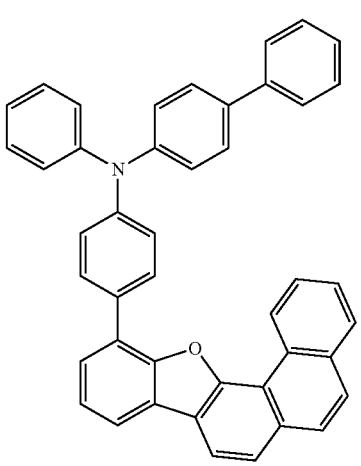

[CF B-3]
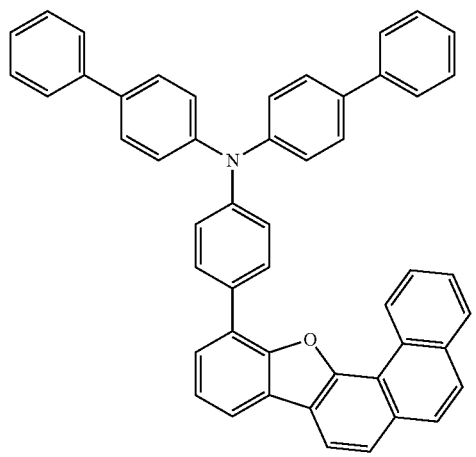
[CF B-6]
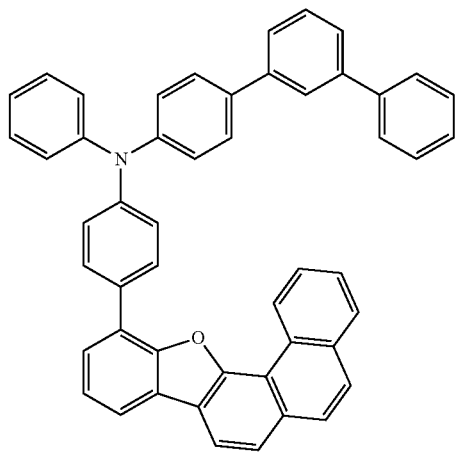
[CF B-4]
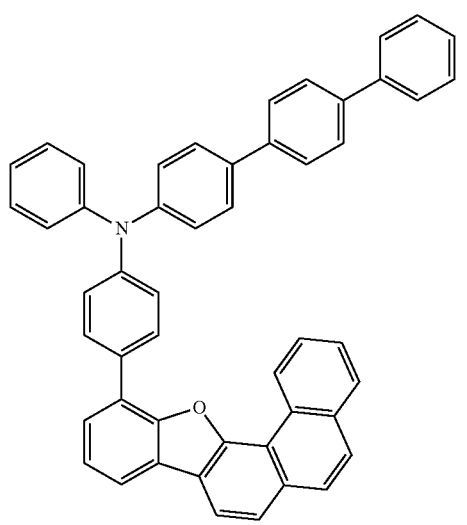
[CF B-7]
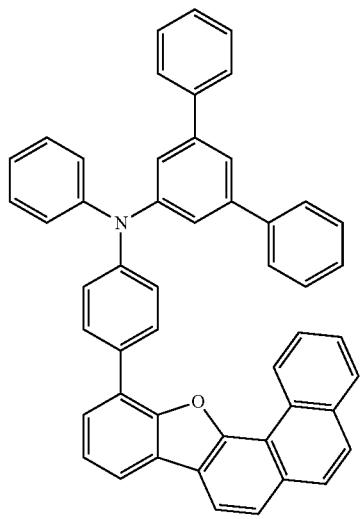
[CF B-5]
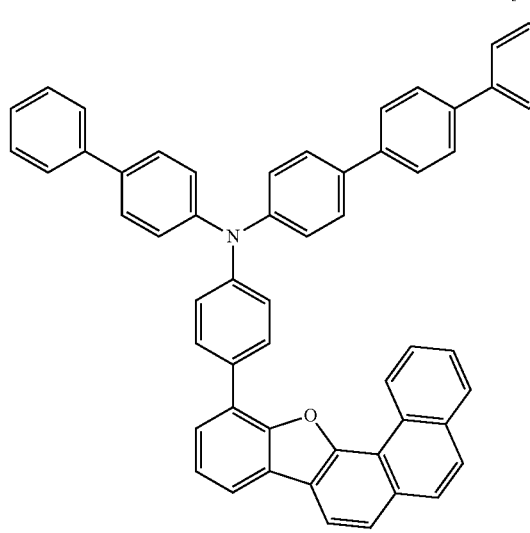
[CF B-8]
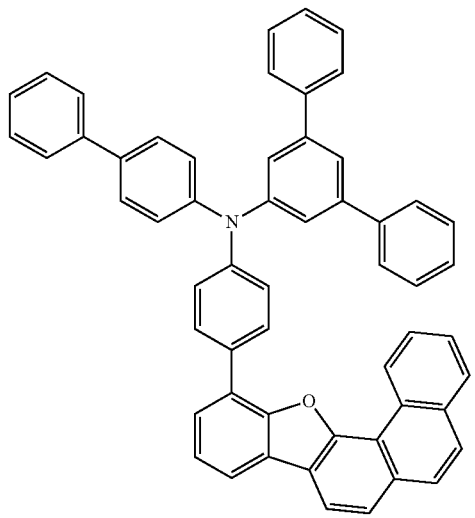

[CF B-9]
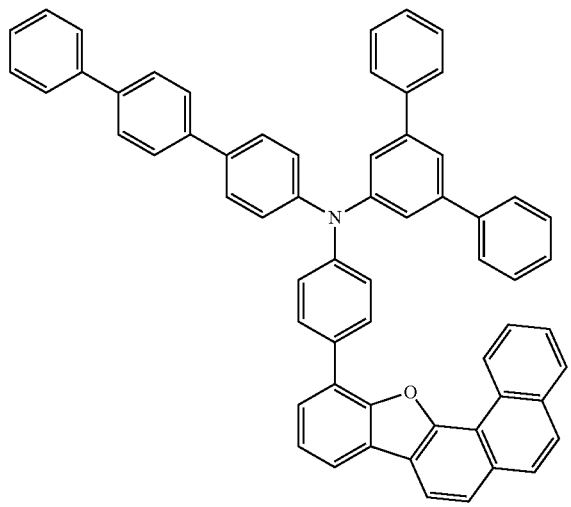
[CF B-10]
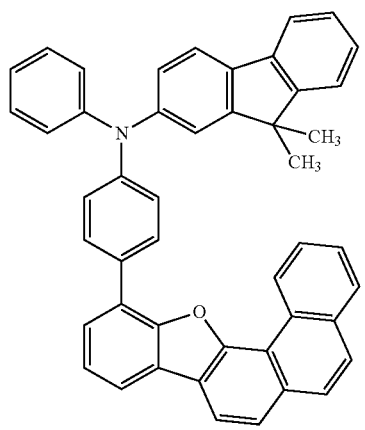
[CF B-11]
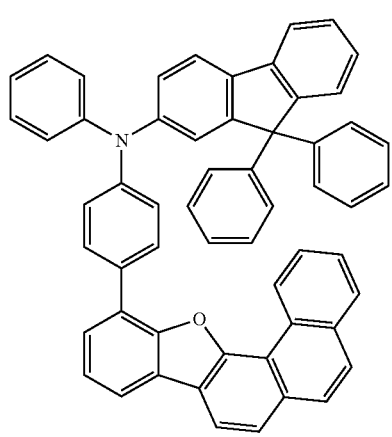
[CF B-12]
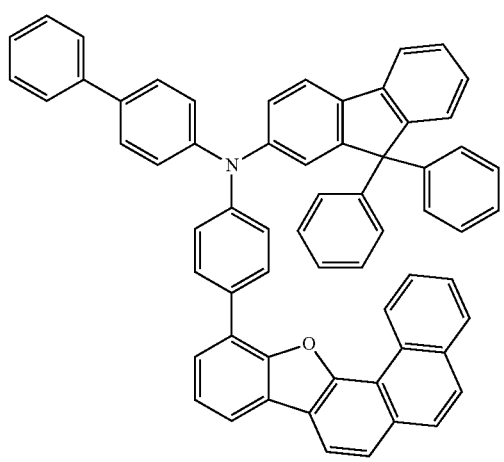
[CF B-13]
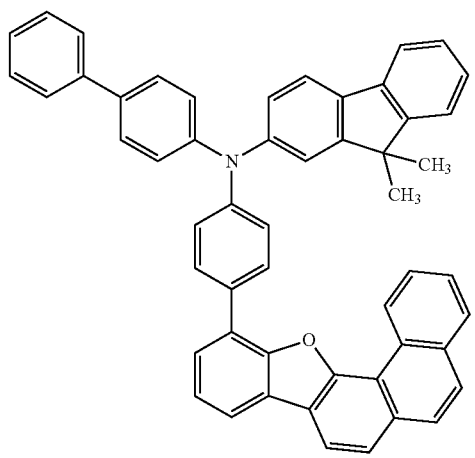
[CF B-14]
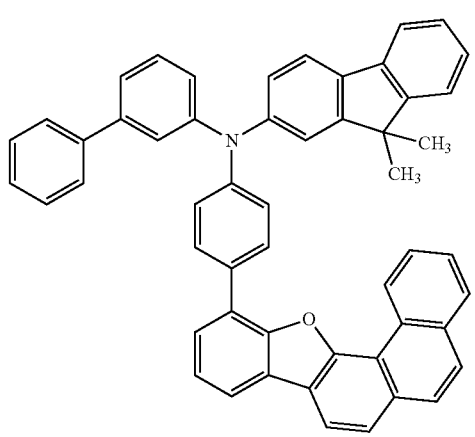

[CF B-15]
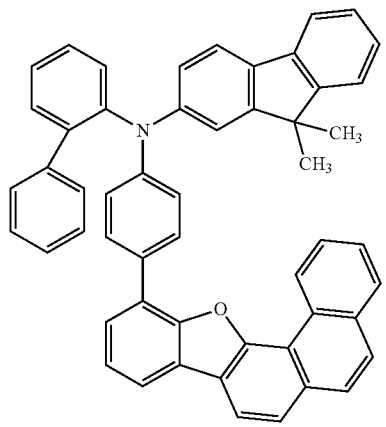
[CF B-16]
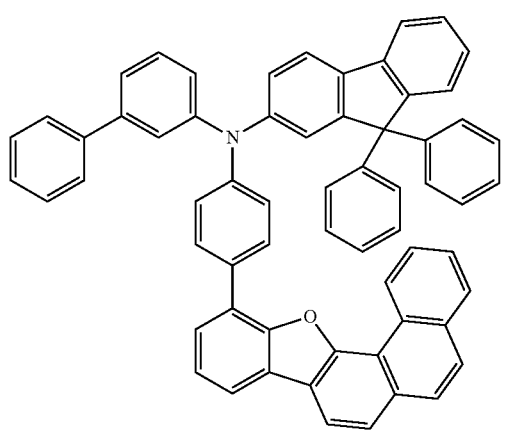
[CF B-17]
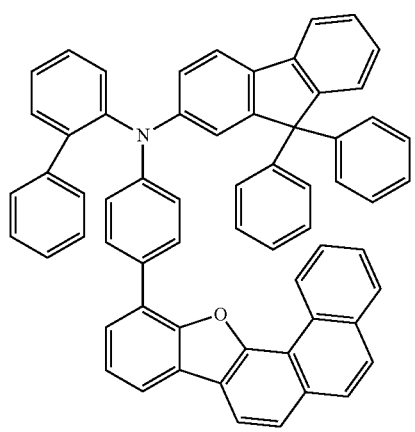
[CF B-18]
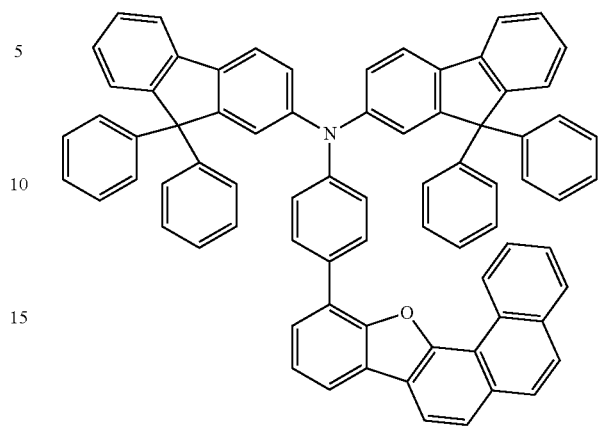
[CF B-19]
[CF B-20]
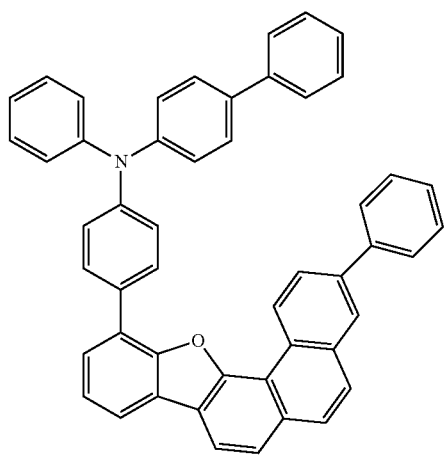

[CF B-21]
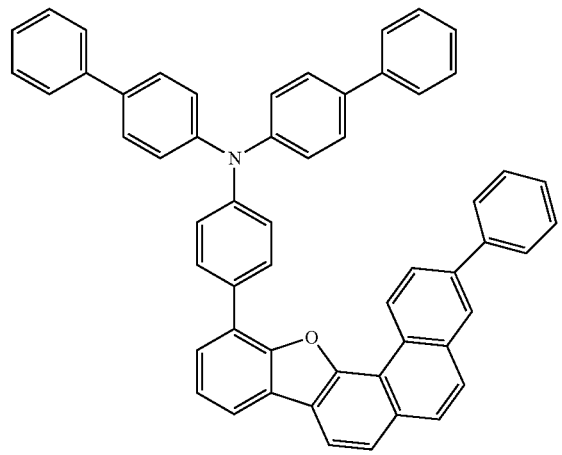
[CF B-22]
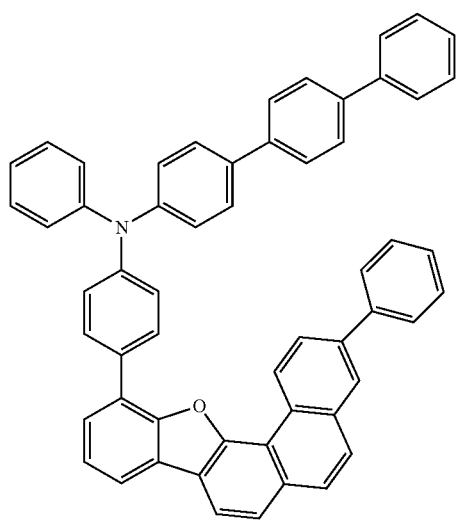
[CF B-23]
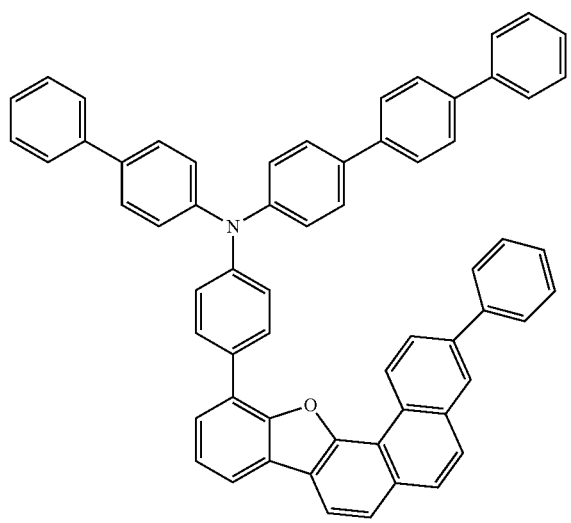
[CF B-24]
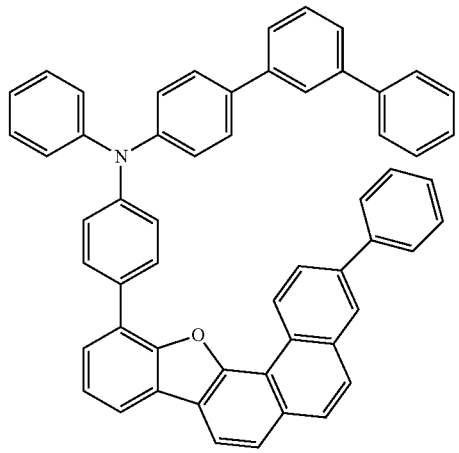
[CF B-25]
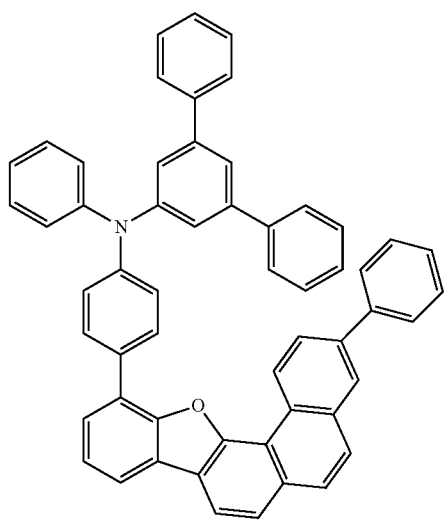
[CF B-26]
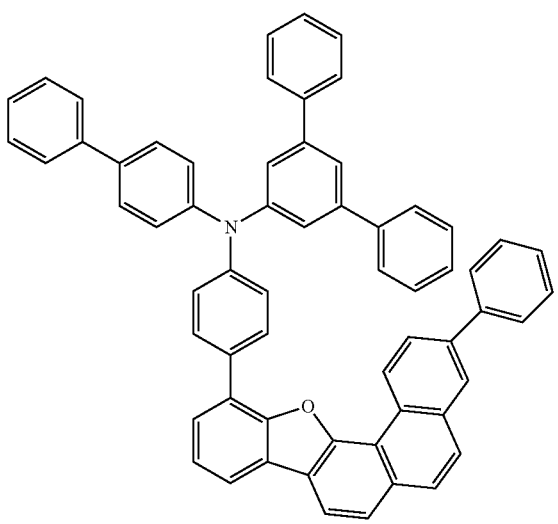

[CF B-27]
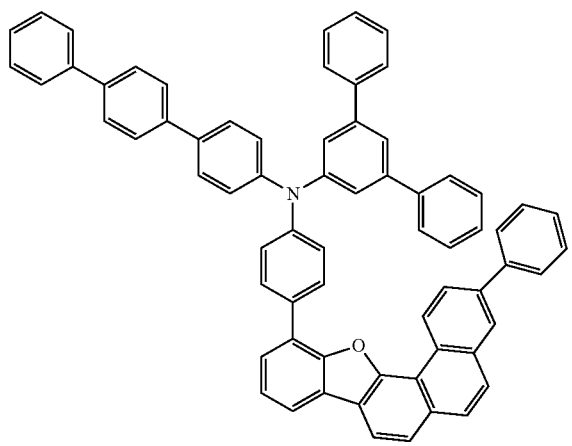
[CF B-30]
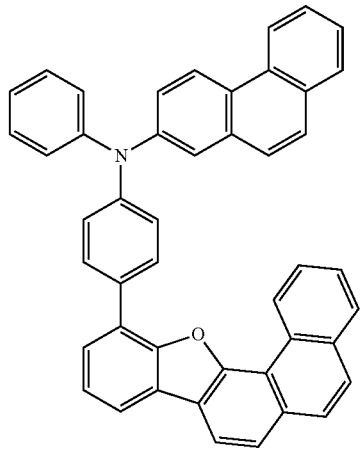
[CF B-28]
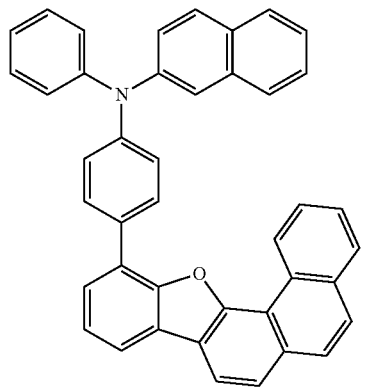
[CF B-31]
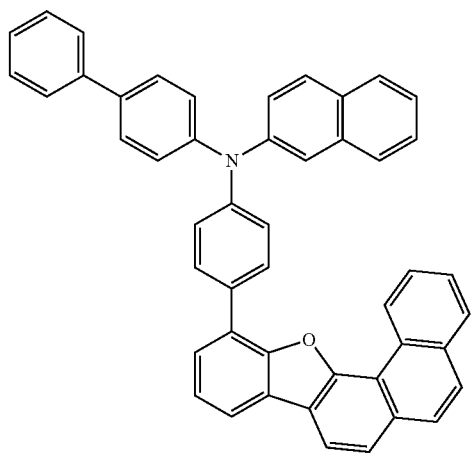
[CF B-29]
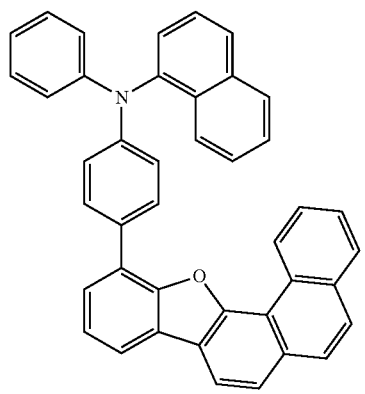
[CF B-32]
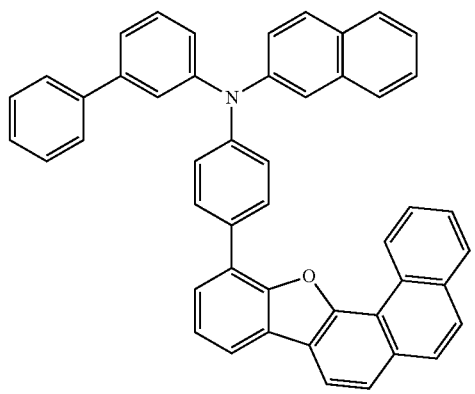

[CF B-33]
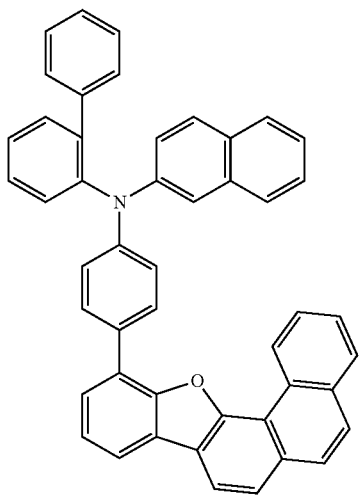
[CF B-34]
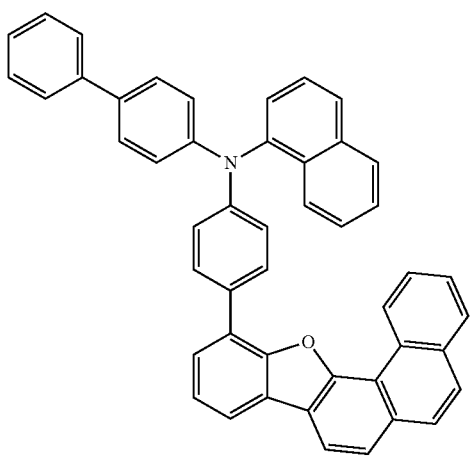
[CF B-35]
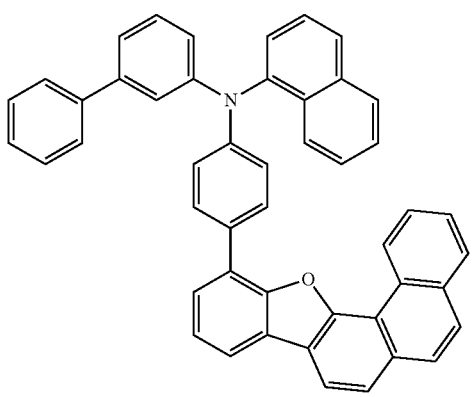
[CF B-36]
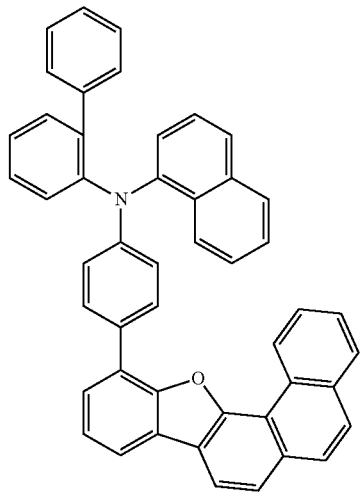
[CF B-37]
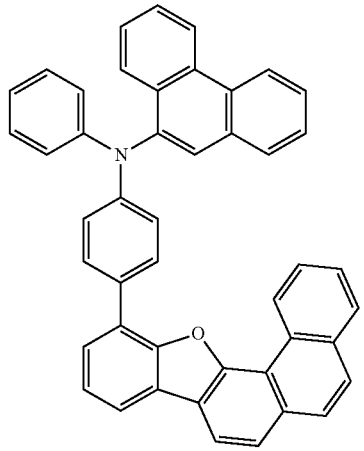
[CF B-38]
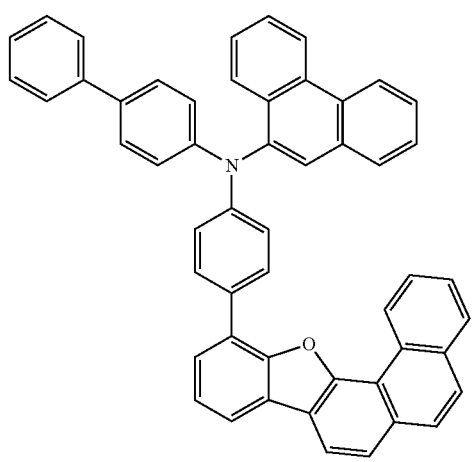

[CF B-39]
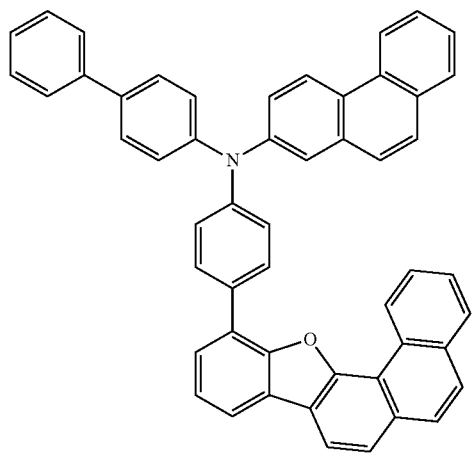
[CF B-40]
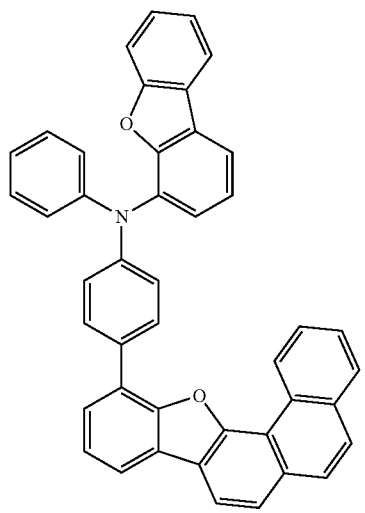
[CF B-41]
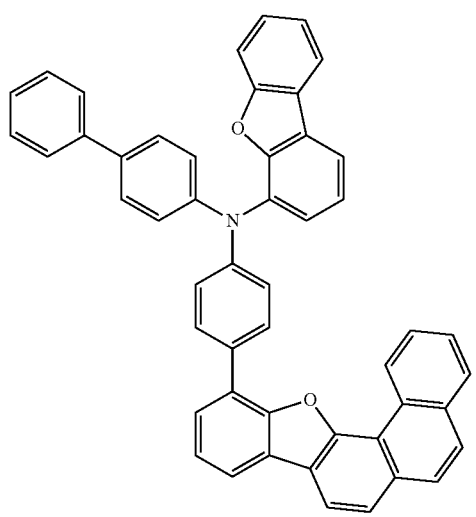
[CF B-42]
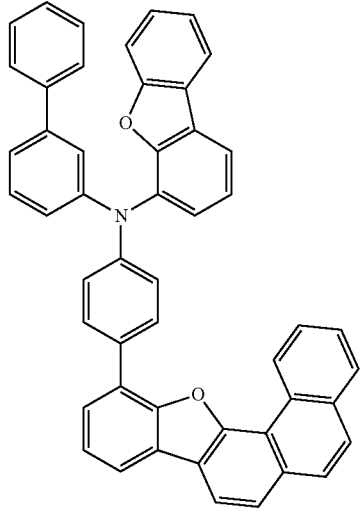
[CF B-43]
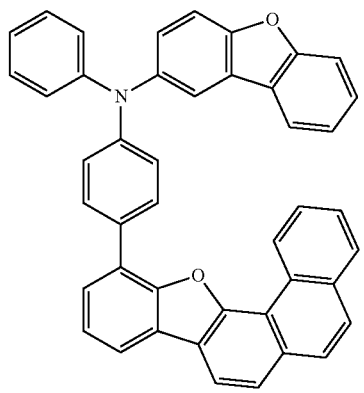
[CF B-44]
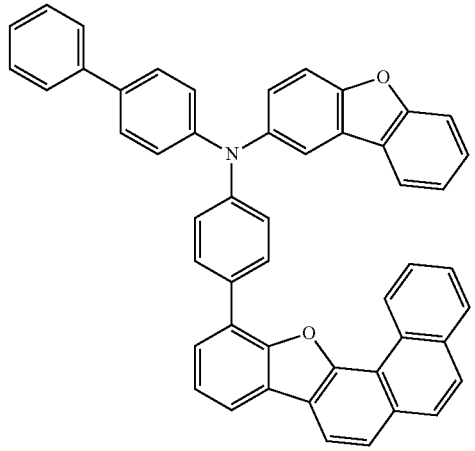

[CF B-45]
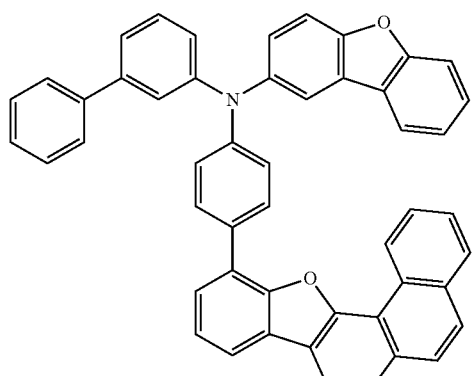
[CF B-48]
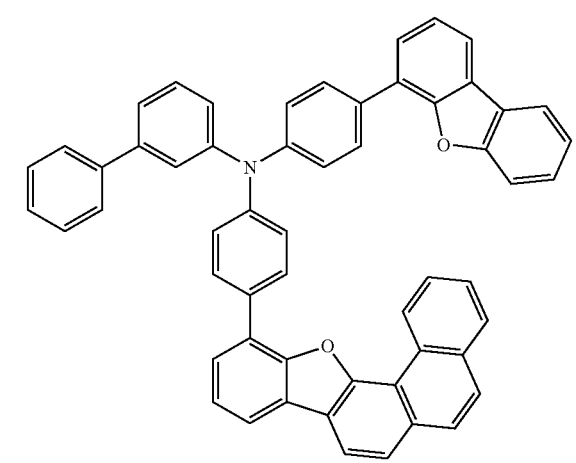
[CF B-46]
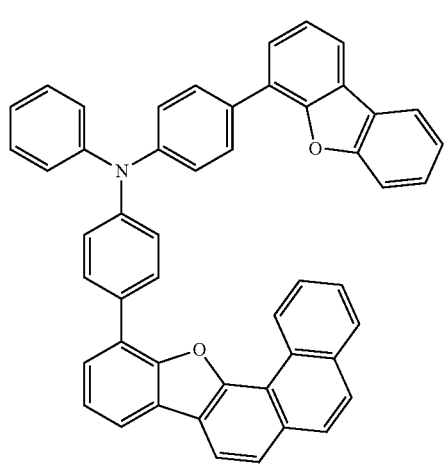
[CF B-49]
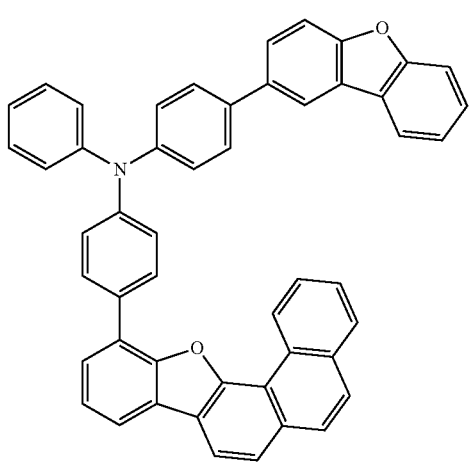
[CF B-47]
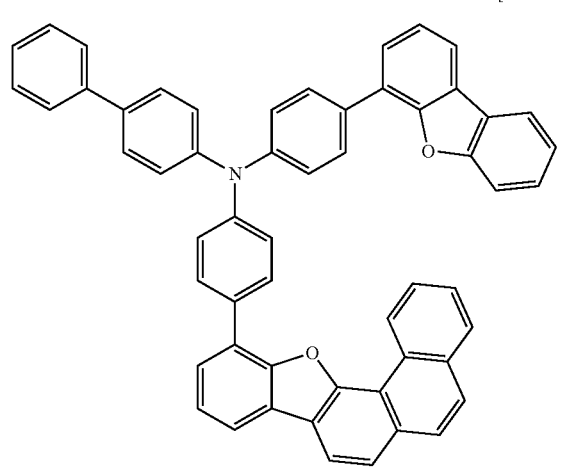
[CF B-50]
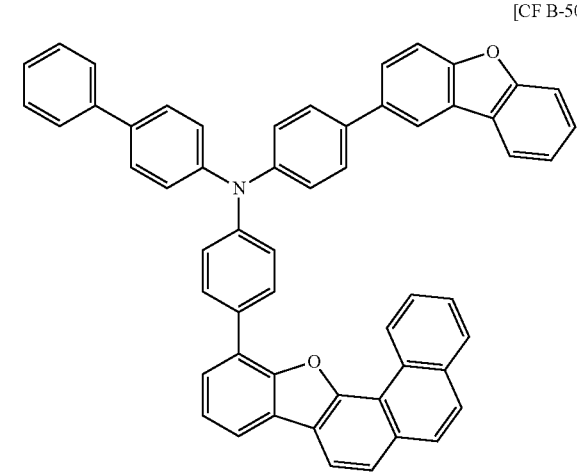

[CF B-51]
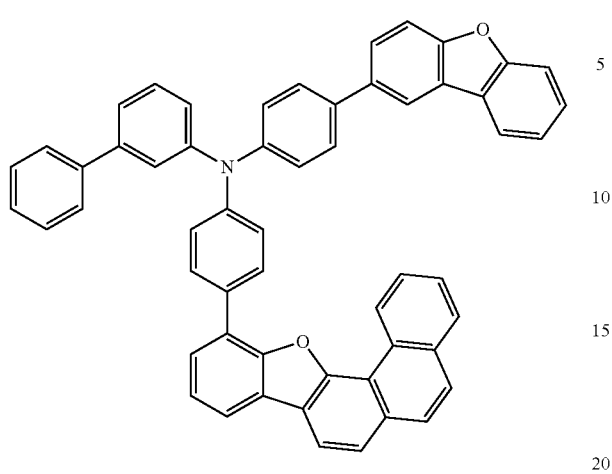
[CF B-54]
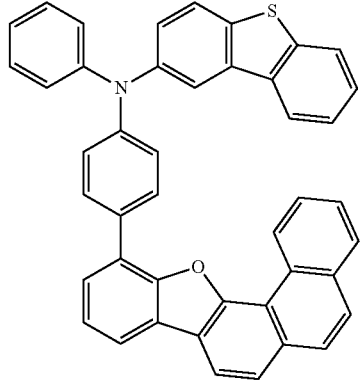
[CF B-52]
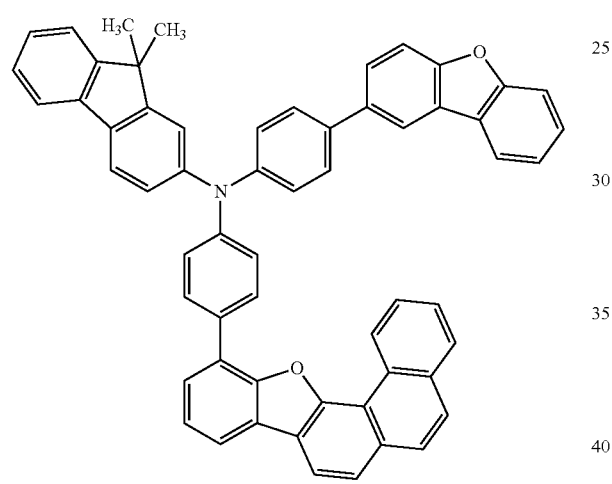
[CF B-55]
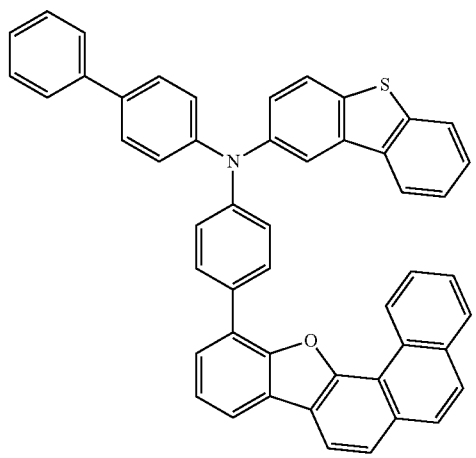
[CF B-53]
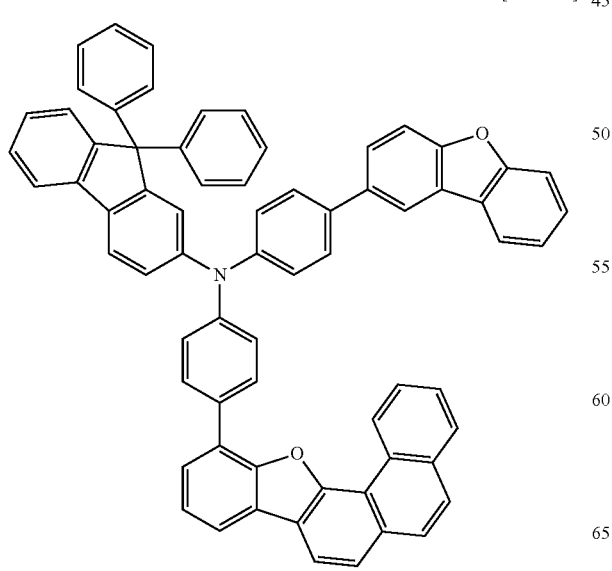
[CF B-56]
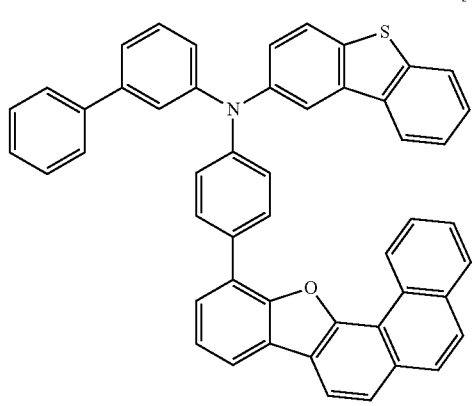

[CF B-57]
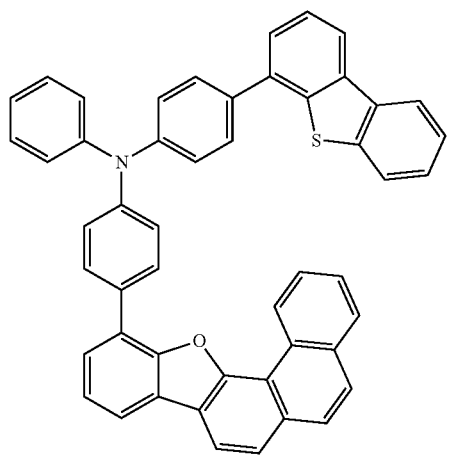
[CF B-60]
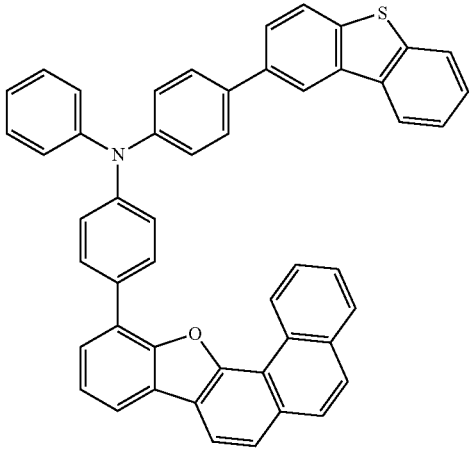
[CF B-58]
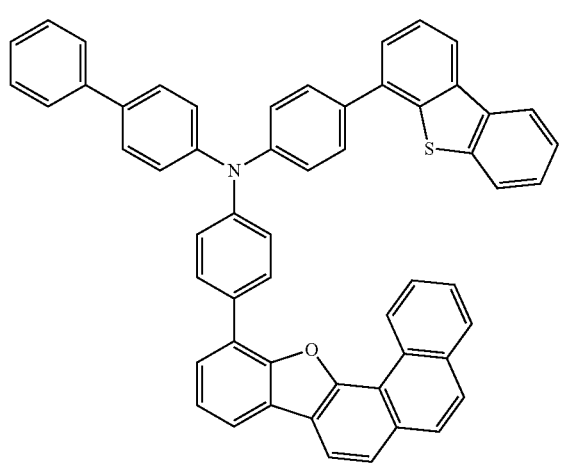
[CF B-61]
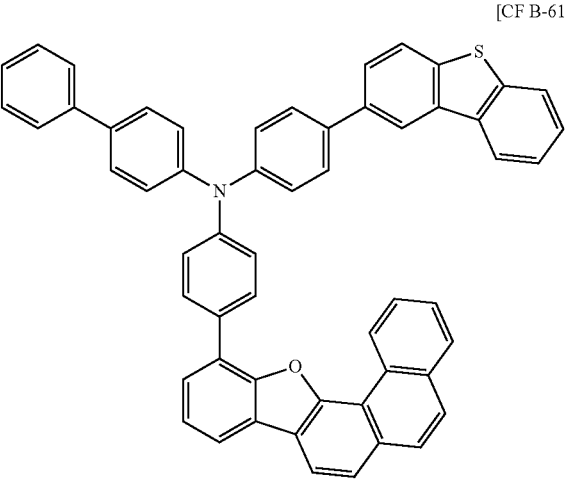
[CF B-59]
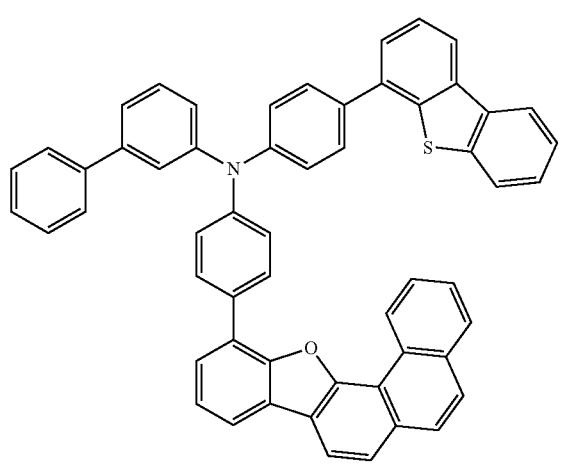
[CF B-62]
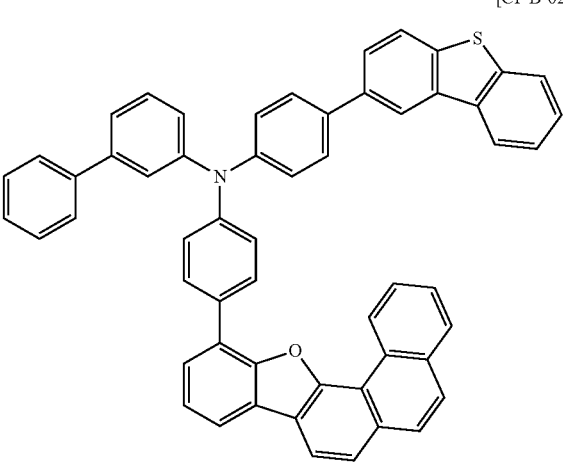

[CF B-63]
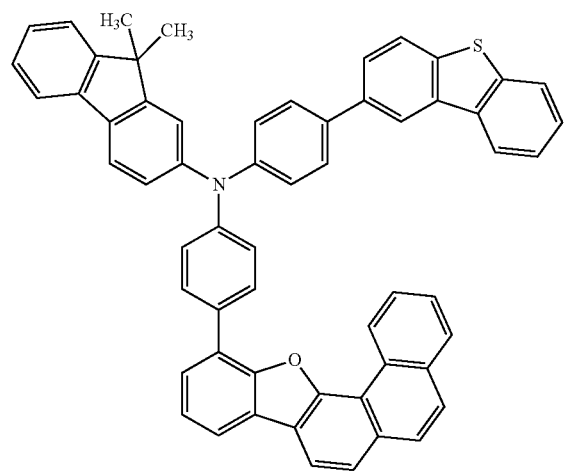
[CF B-66]
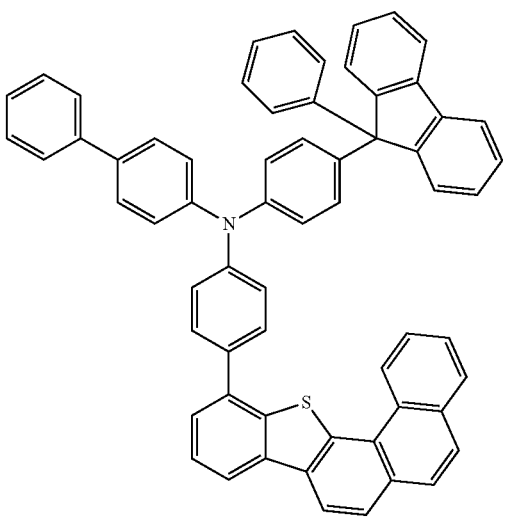
[CF B-64]
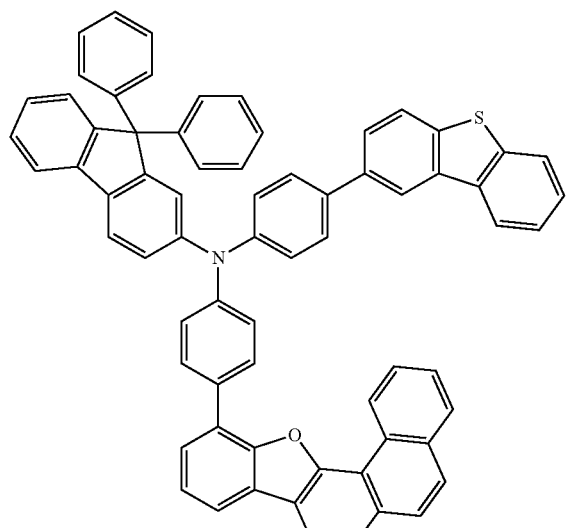
[CF B-67]
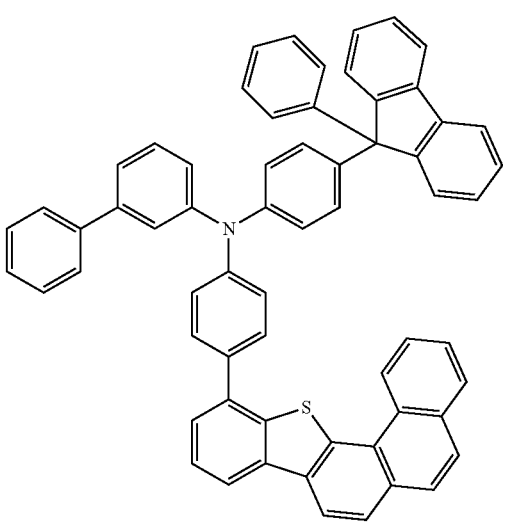
[CF B-65]
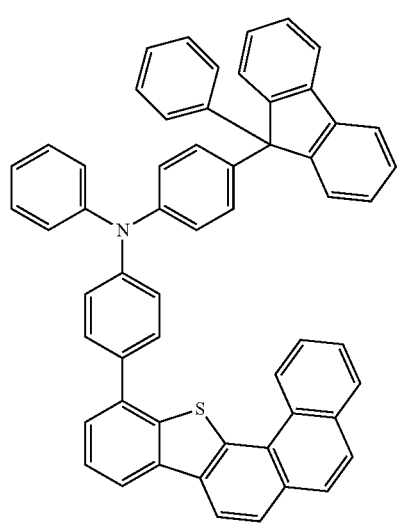
[CF B-68]

[CF B-69]
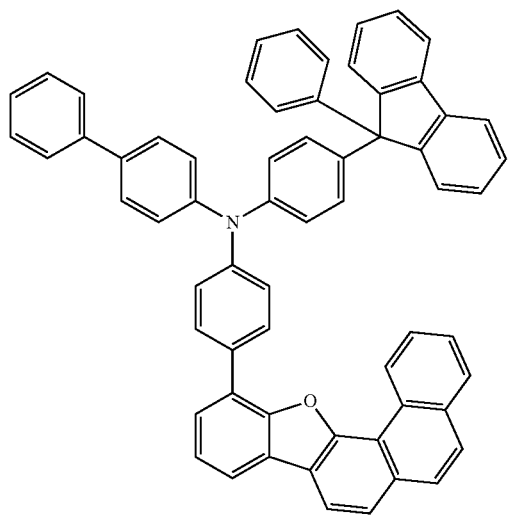
[CF B-70]
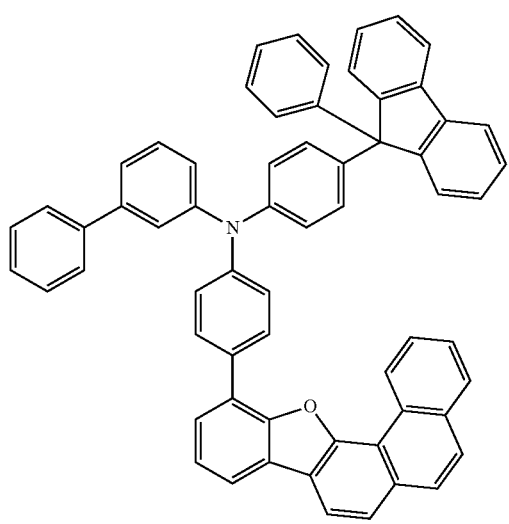
[CF B-71]
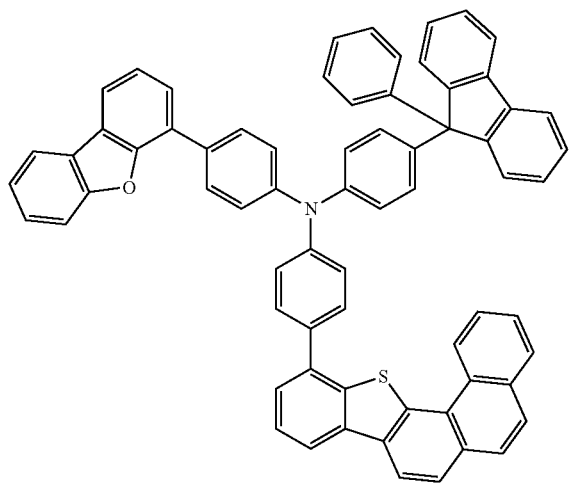
[CF B-72]
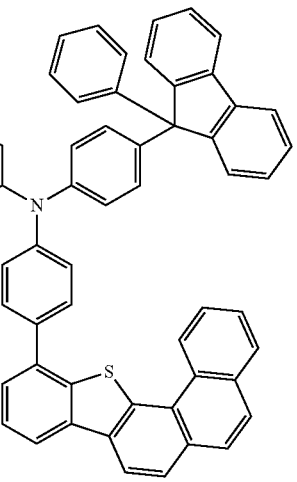
[CF B-73]
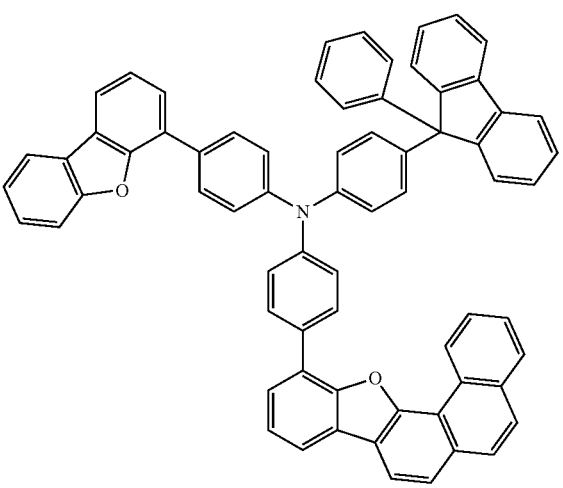
[CF B-74]
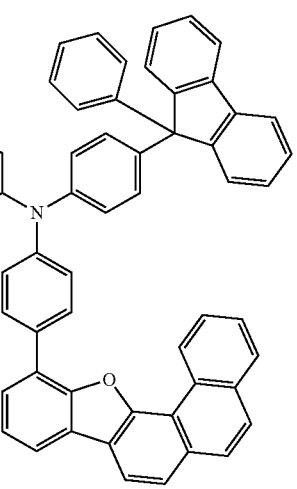

-continued
[CF B-75]
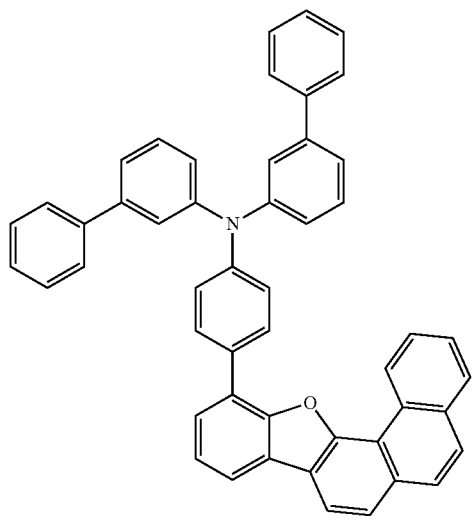
[CF B-76]
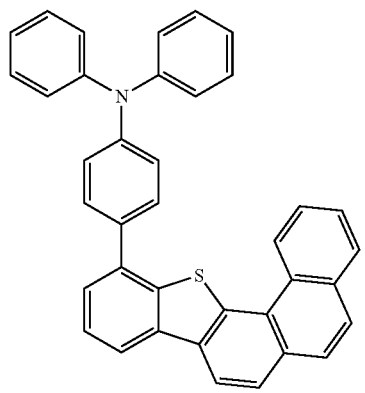
[CF B-77]
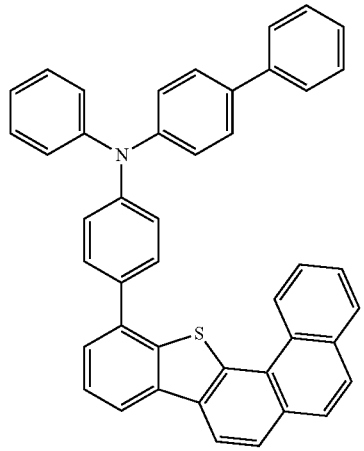
[CF B-78]
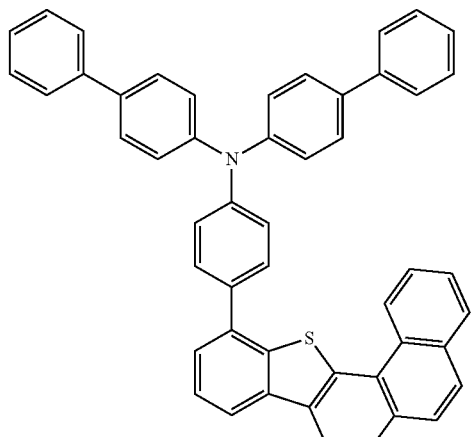
[CF B-79]
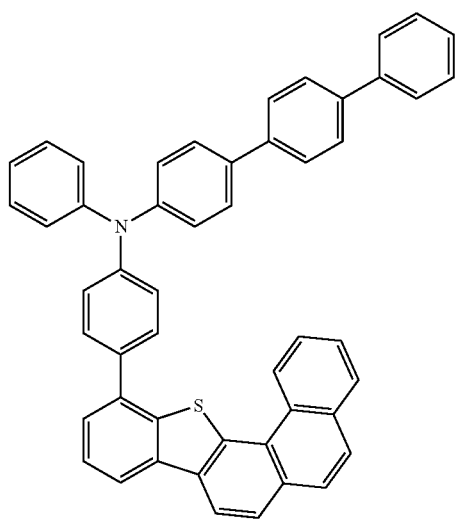
[CF B-80]
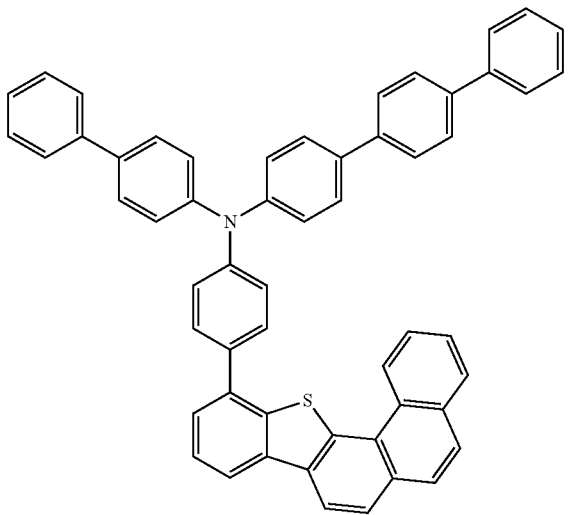

[CF B-81]
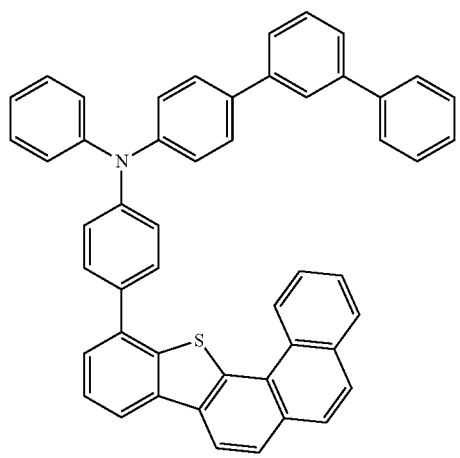
[CF B-84]
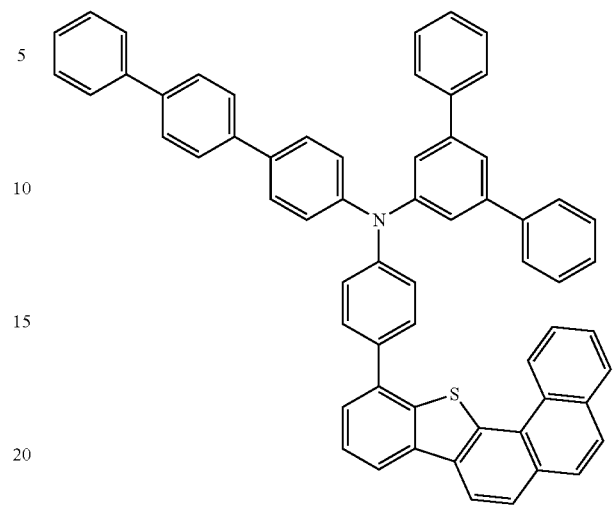
[CF B-82]
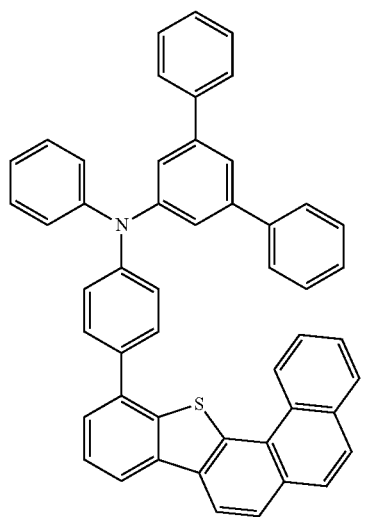
[CF B-85]
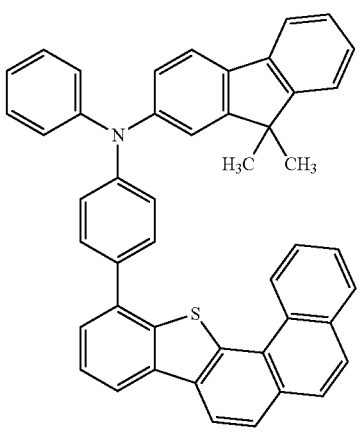
[CF B-83]
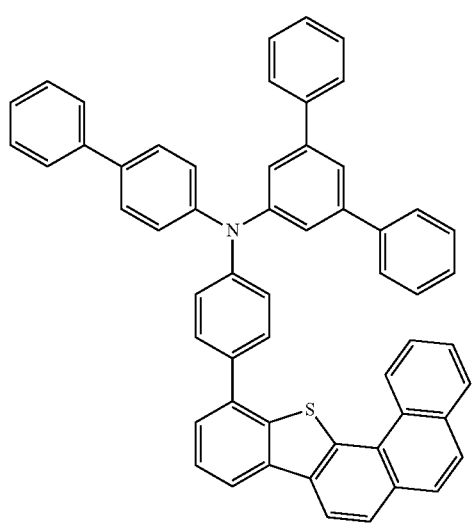
[CF B-86]
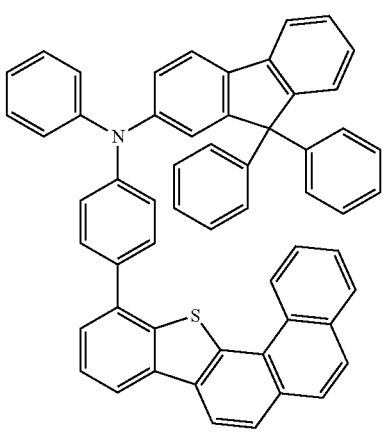

[CF B-87]
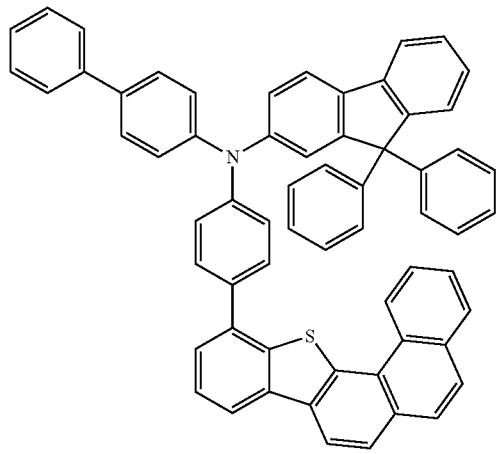
[CF B-90]
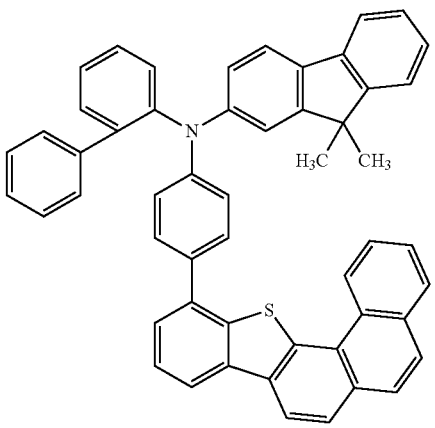
[CF B-88]
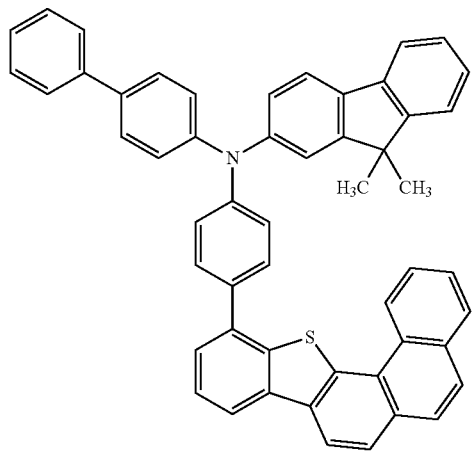
[CF B-91]
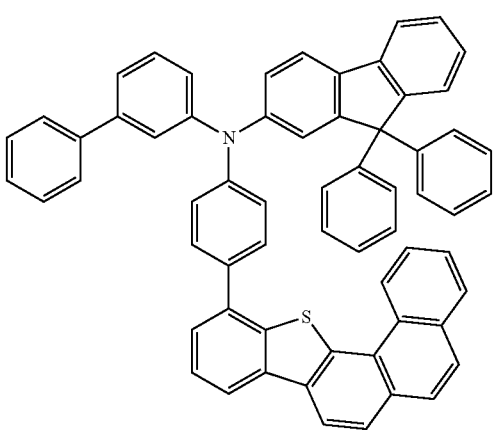
[CF B-89]
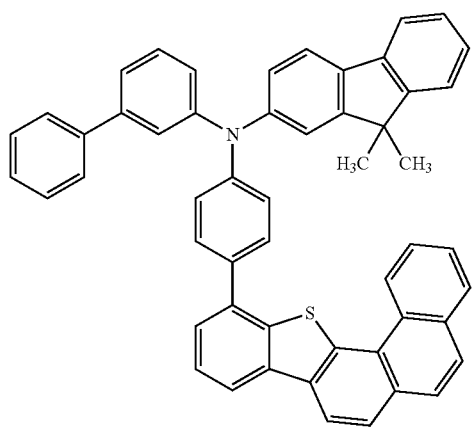
[CF B-92]
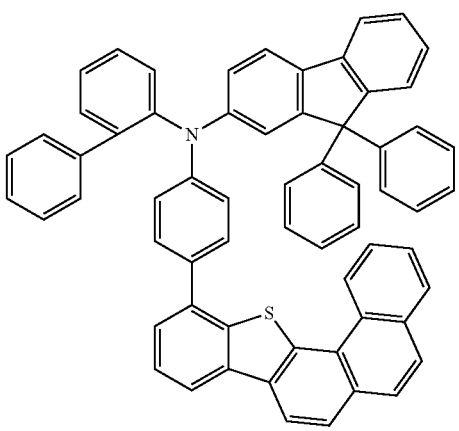

[CF B-93]
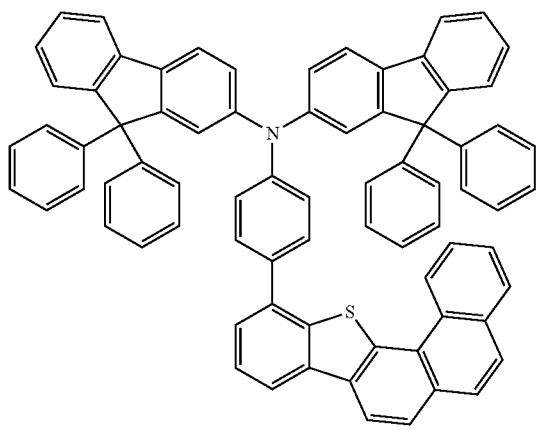
[CF C-3]
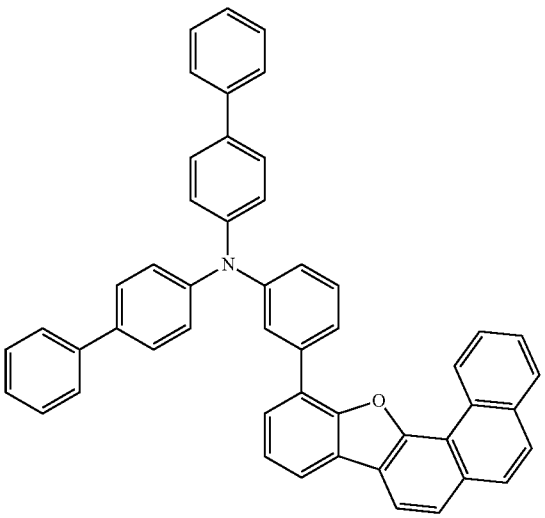
[CF C-1]
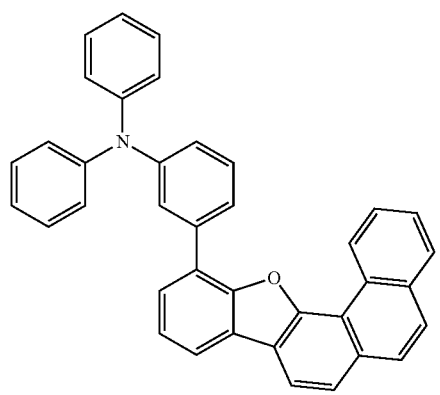
[CF C-2]
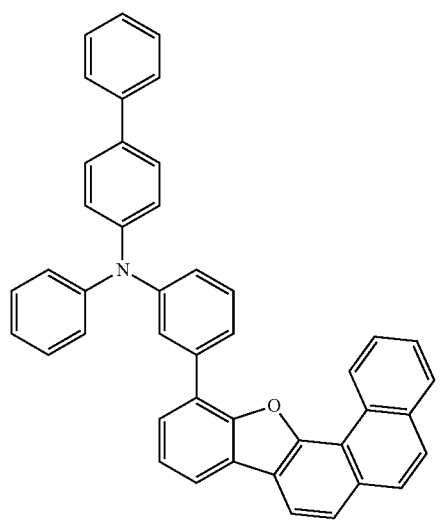
[CF C-4]
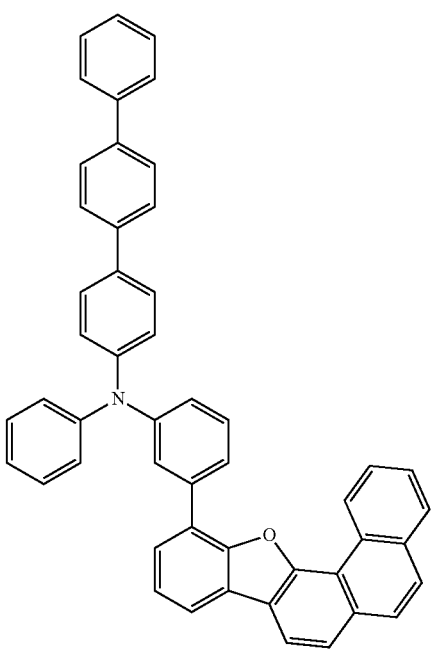

[CF C-5]
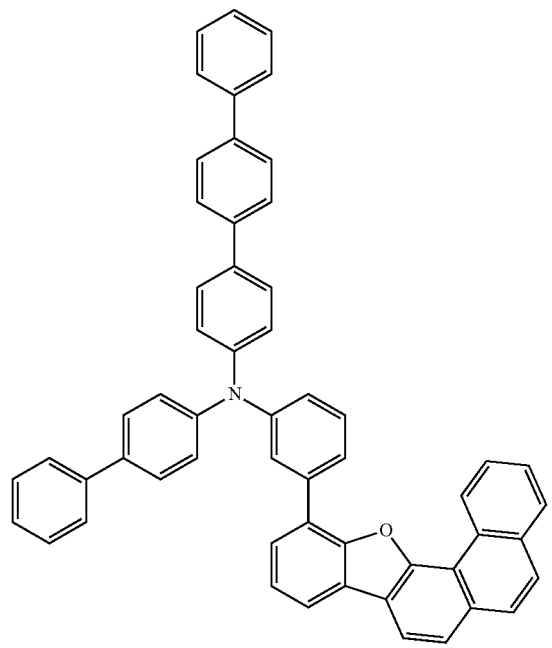
[CF C-6]
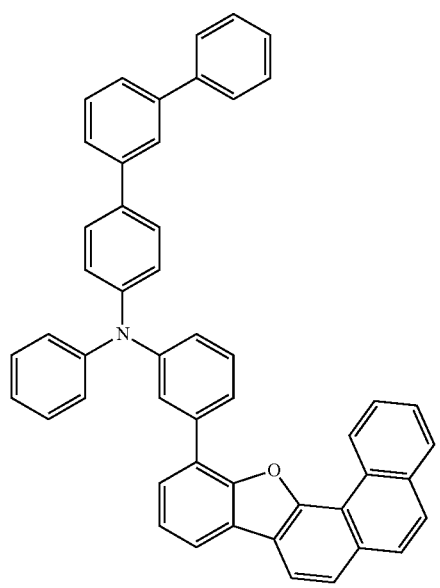
[CF C-7]
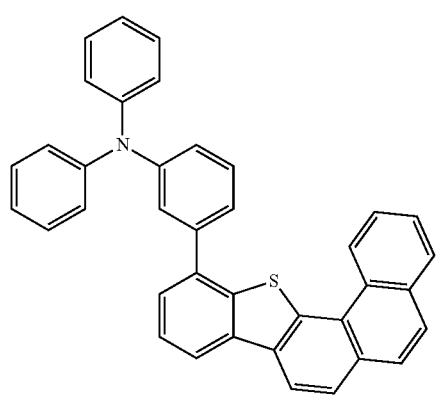
[CF C-8]
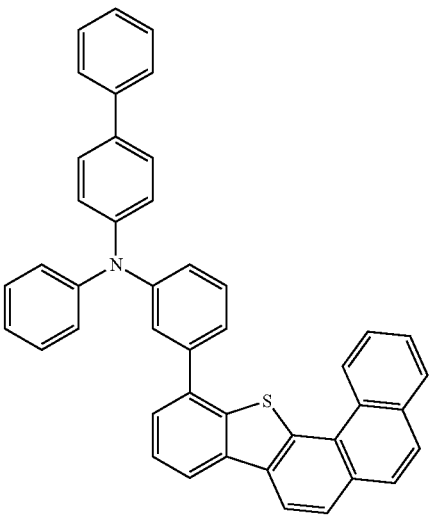
[CF C-9]
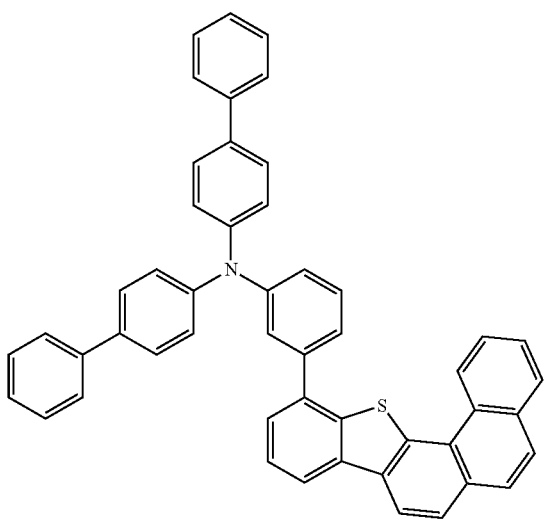

[CF C-10]
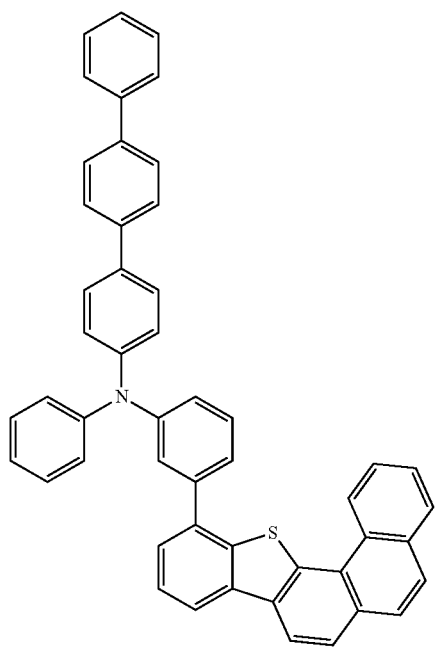
[CF C-12]
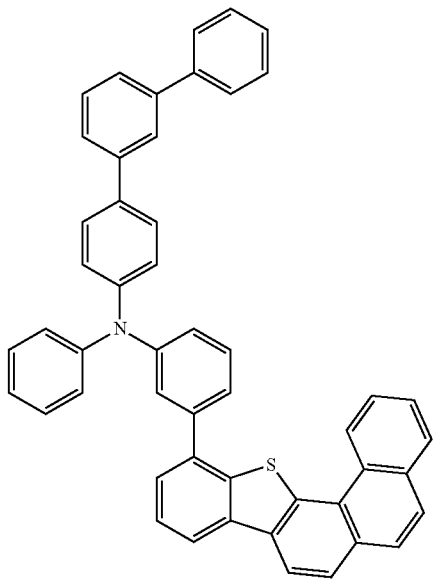
[CF C-11]
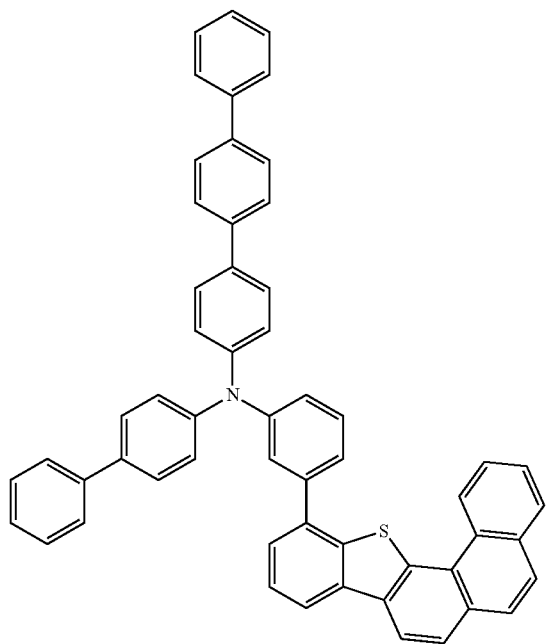
[CF D-1]
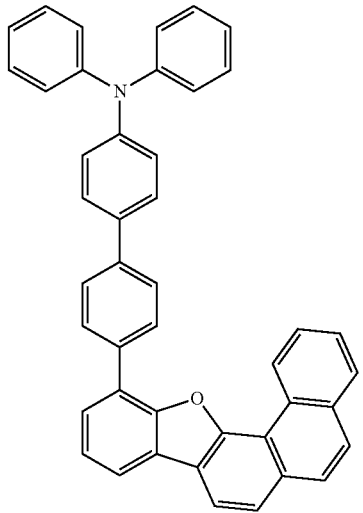

[CF D-2]
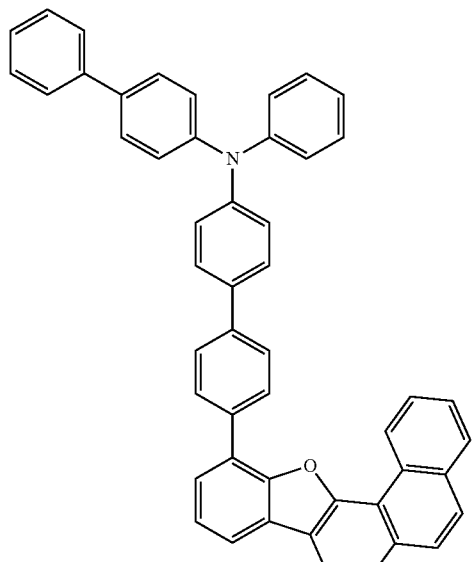
[CF D-4]
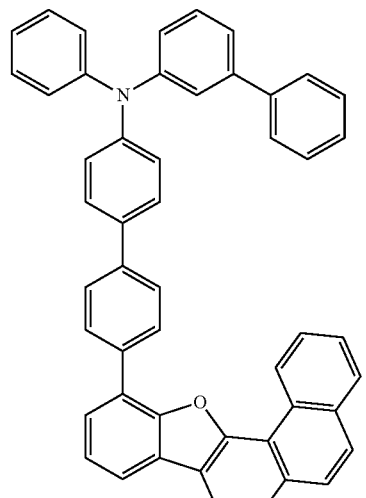
[CF D-5]
[CF D-3]
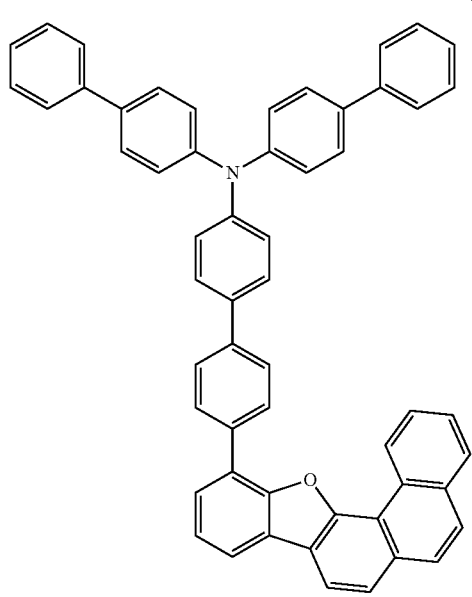
[CF D-6]
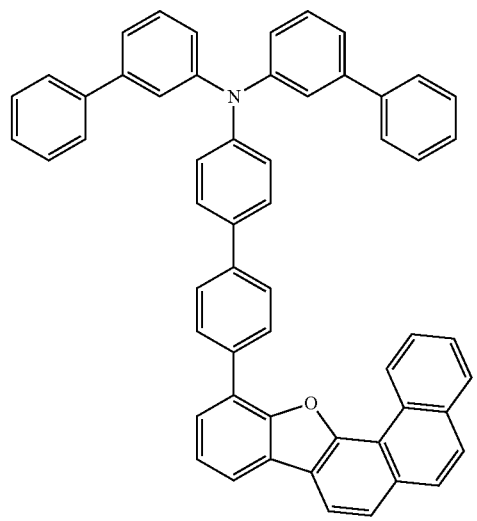

[CF D-7]
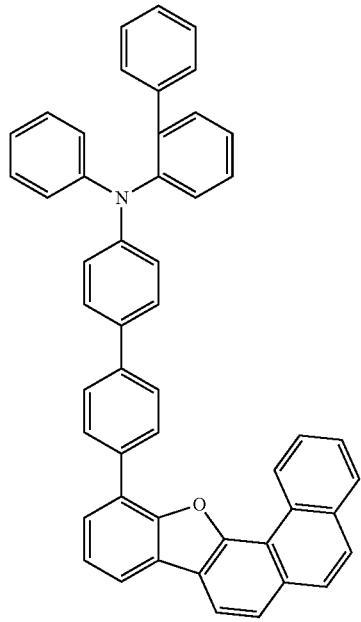
[CF D-9]
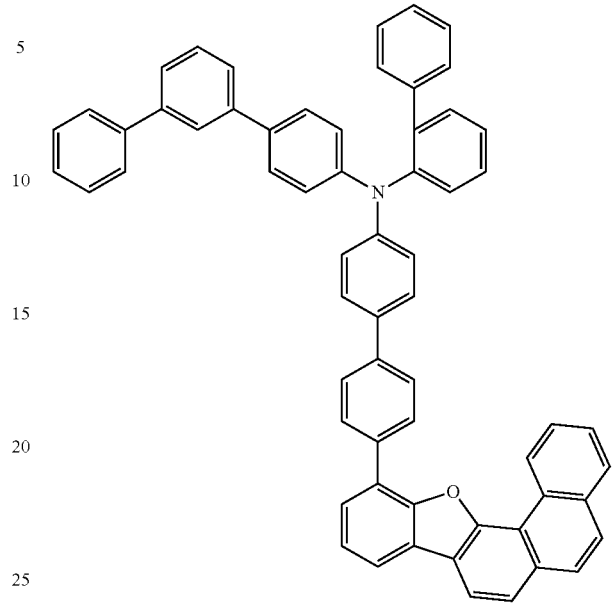
[CF E-1]
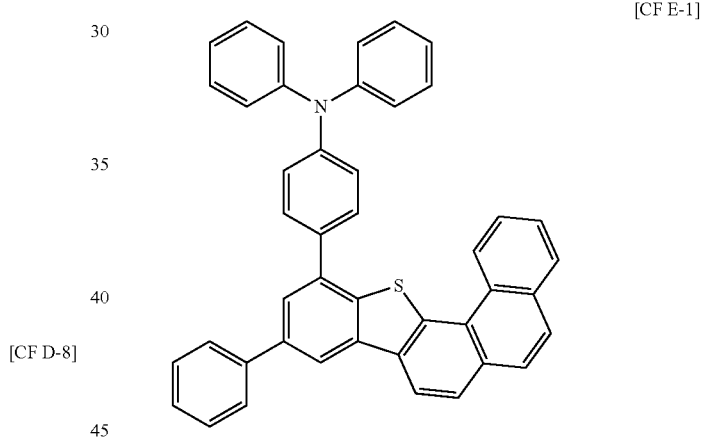
[CF D-8]
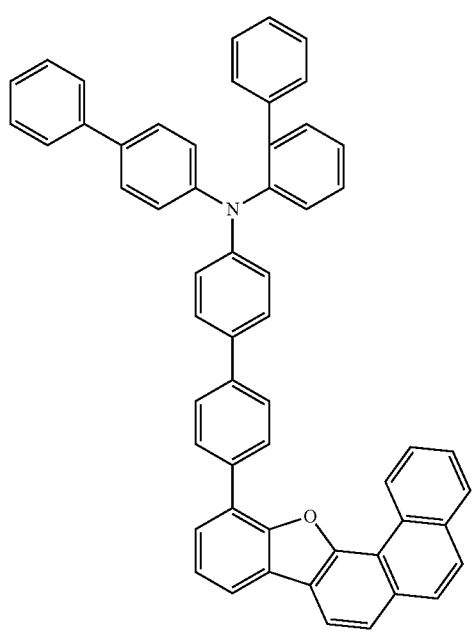
[CF E-2]
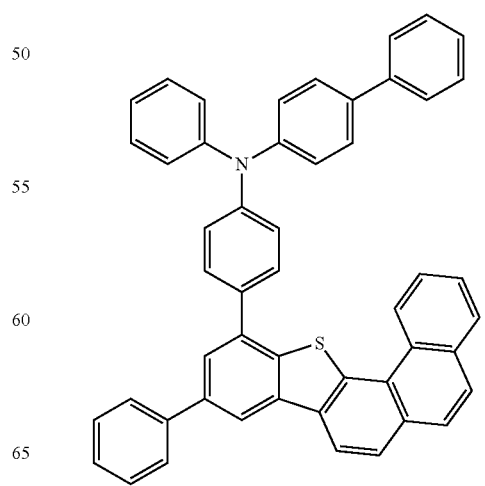

-continued
[CF E-3]
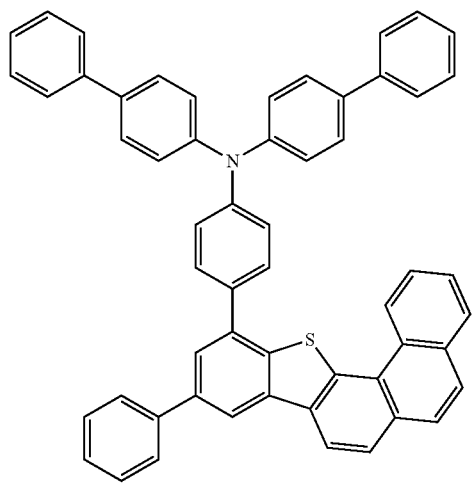
[CF E-4]
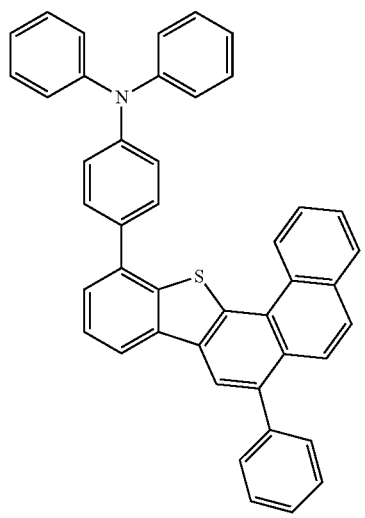
[CF E-5]
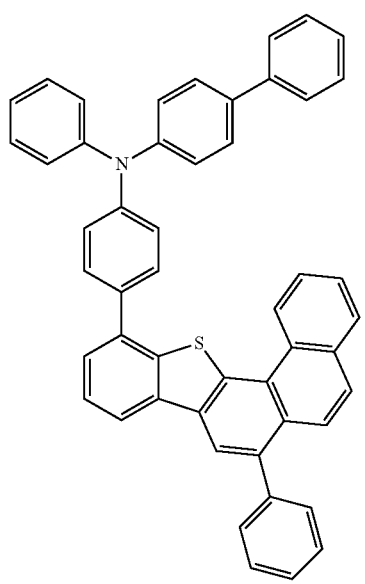
[CF E-6]
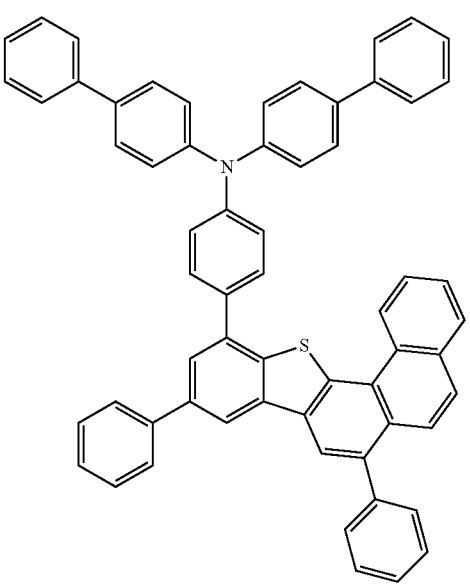
[CF E-7]
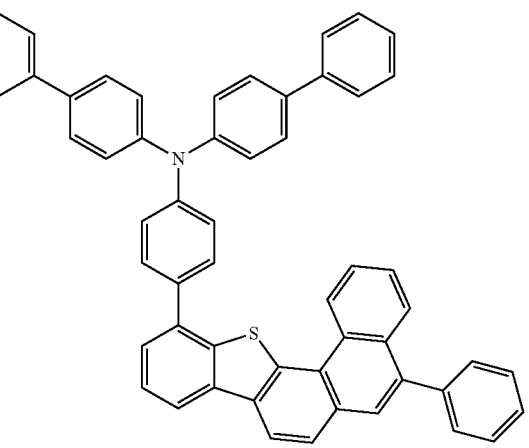
[CF E-8]
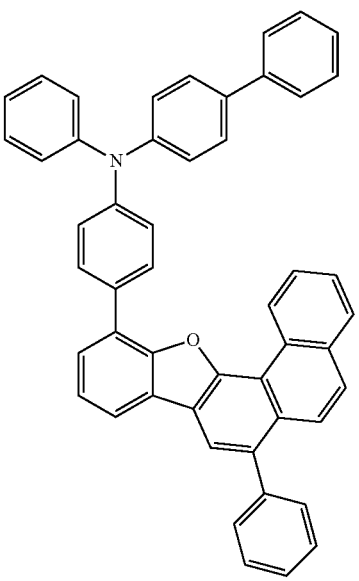

-continued

[CF E-9]

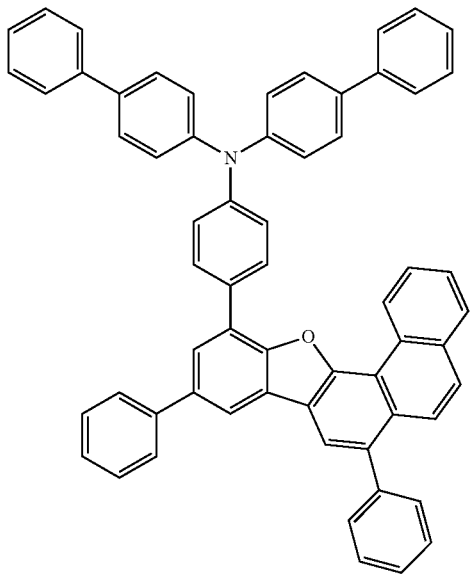

The organic compound may be applied to an organic optoelectric device.

The organic compound may be applied to an organic optoelectric device alone or along with other organic compounds. The organic compound may be applied with other organic compounds in a form of a composition.

Hereinafter, an organic optoelectric device including the organic compound is described.

The organic optoelectric device may be any device to convert electrical energy into photoenergy and vice versa without particular limitation, and may be, for example an organic photoelectric diode, an organic light emitting diode, an organic solar cell, and an organic photo conductor drum.

The organic optoelectric device may include an anode and a cathode facing each other, at least one organic layer between the anode and the cathode, and the organic layer includes the organic compound.

Herein, an organic light emitting diode as one example of an organic optoelectric device is described referring to drawings.

Figure 2:
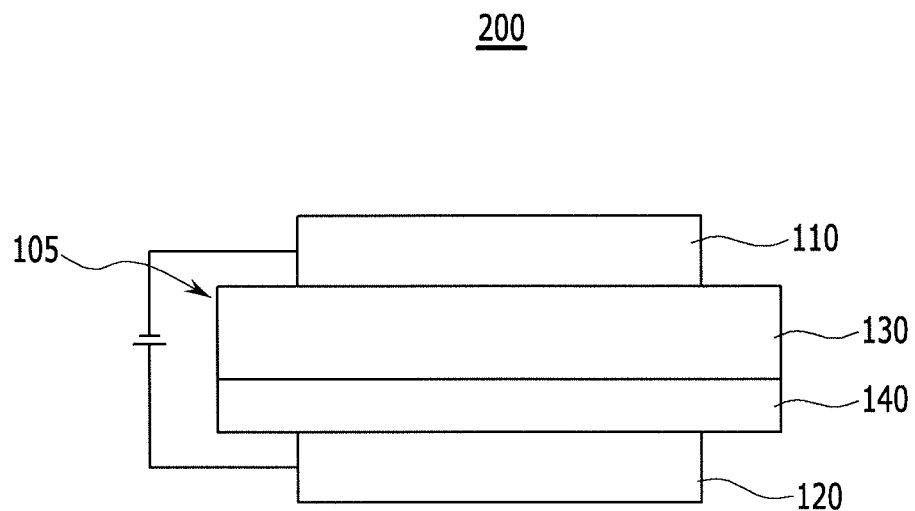
Figure 3:
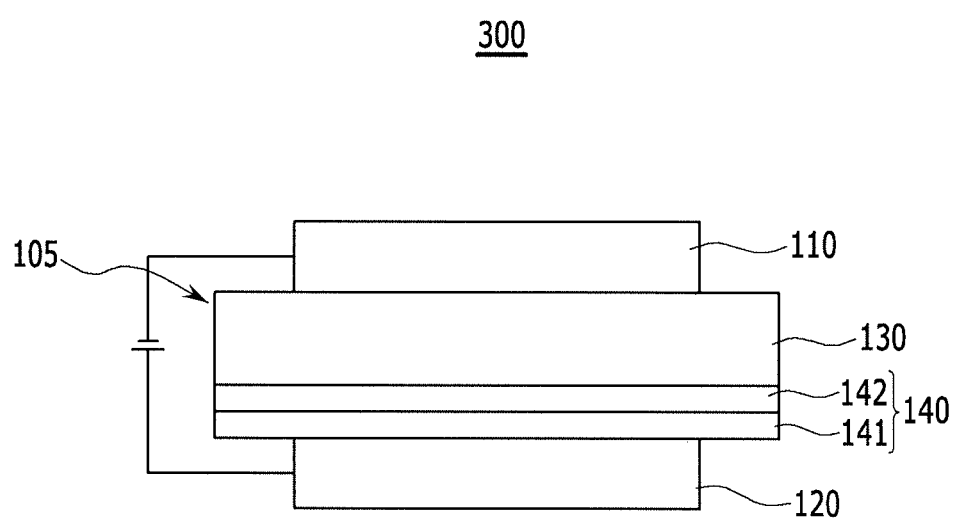

FIGS. 1 to 3 are cross-sectional views showing organic light emitting diodes according to each embodiment.

Referring to FIG. 1, an organic light emitting diode 100 according to an embodiment includes an anode 120 and a cathode 110 and an organic layer 105 between the anode 120 and the cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes the organic compound.

Referring to FIG. 2, an organic light emitting diode 200 according to an embodiment includes an anode 120 and a cathode 110 facing each other, and an organic layer 105 between the anode 120 and the cathode 110, and the organic layer 105 includes an emission layer 130 and a hole transport layer 140.

The hole transport layer 140 is disposed between the anode 120 and the emission layer 130, and includes the organic compound.

Referring to FIG. 3, an organic light emitting diode 300 according to an embodiment includes an anode 120 and a cathode 110 facing each other, and an organic layer 105 between the anode 120 and the cathode 110.

The organic layer 105 includes an emission layer 130 and a hole transport layer 140, and the hole transport layer 140 includes a first hole transport layer 141 adjacent to the anode 120 and a second hole transport layer 142 adjacent to the emission layer 130.

The organic compound may be included in the second hole transport layer 142 adjacent to the emission layer 130.

The first hole transport layer 141 may include, for example an organic compound represented by Chemical Formula 3.

[Chemical Formula 3]

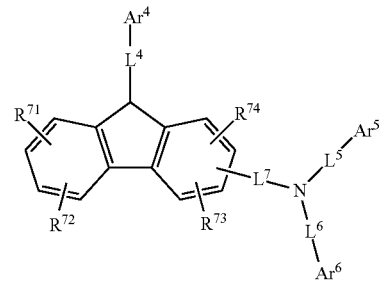

In Chemical Formula 3, $R^{71}$ to $R^{74}$ are independently hydrogen, deuterium, a substituted or unsubstituted C1 to C10 alkyl group, a substituted or unsubstituted C6 to C30 aryl group, a substituted or unsubstituted C2 to C30 heterocyclic group, or a combination thereof, $R^{71}$ and $R^{72}$ are independently present or form a fused ring, $R^{73}$ and $R^{74}$ are independently present or form a fused ring, $Ar^4$ to $Ar^6$ are independently a substituted or unsubstituted C6 to C30 aryl group or a substituted or unsubstituted C2 to C30 heterocyclic group, and $L^4$ to $L^7$ are independently a single bond, a substituted or unsubstituted C2 to C10 alkylene group, a substituted or unsubstituted C2 to C10 alkenylene group, a substituted or unsubstituted C2 to C10 alkynylene group, a substituted or unsubstituted C6 to C30 arylene group, a substituted or unsubstituted C2 to C30 heterocyclic group or a combination thereof.

For example, Ar$^4$ of Chemical Formula 3 may be a substituted or unsubstituted phenyl group, or a substituted or unsubstituted biphenyl group, and Ar$^5$ and Ar$^6$ of Chemical Formula 3 may independently be a substituted or unsubstituted phenyl group, a substituted or unsubstituted biphenyl group, a substituted or unsubstituted fluorene group, a substituted or unsubstituted bisfluorene group, a substituted or unsubstituted triphenylene group, a substituted or unsubstituted anthracene group, a substituted or unsubstituted terphenyl group, a substituted or unsubstituted dibenzofuran group, or a substituted or unsubstituted dibenzothiophenyl group.

The compound represented by Chemical Formula 3 may be, for example one of compounds represented by Chemical Formula J-1 to Chemical Formula J-144, but is not limited thereto.

[J-1]

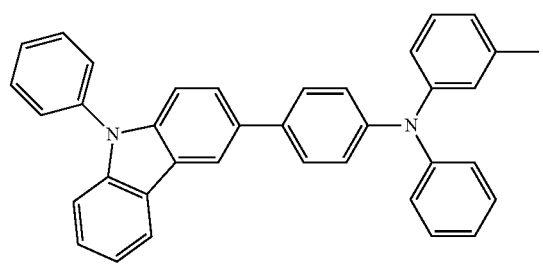

[J-2]

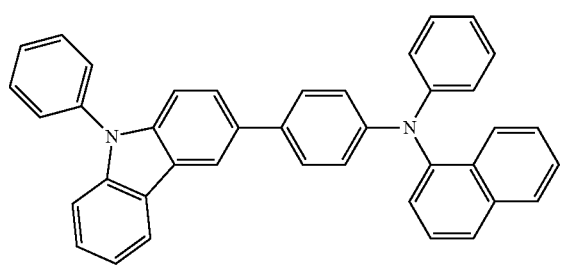

[J-3]

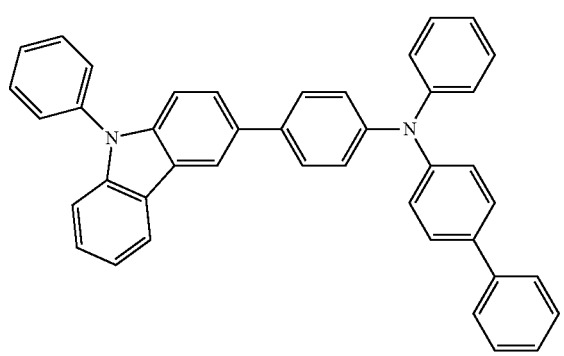

[J-4]

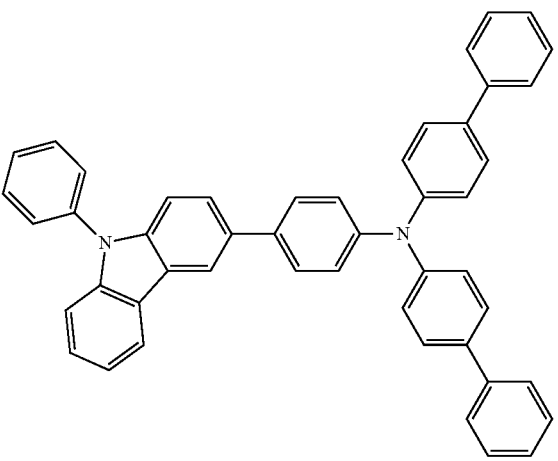

[J-5]

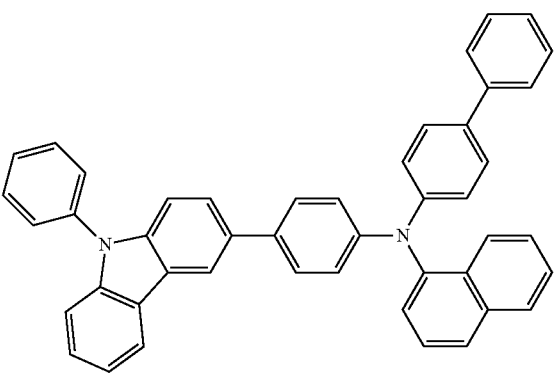

[J-6]

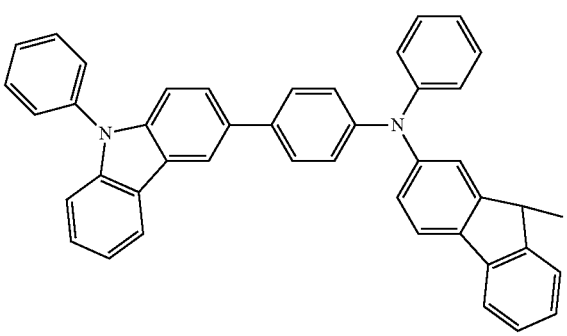

[J-7]
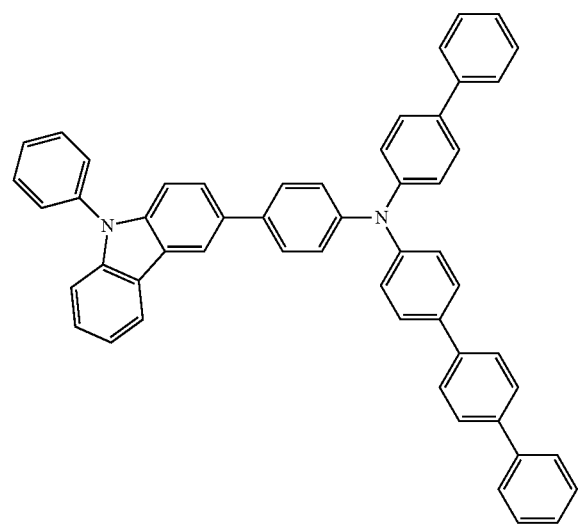
[J-8]
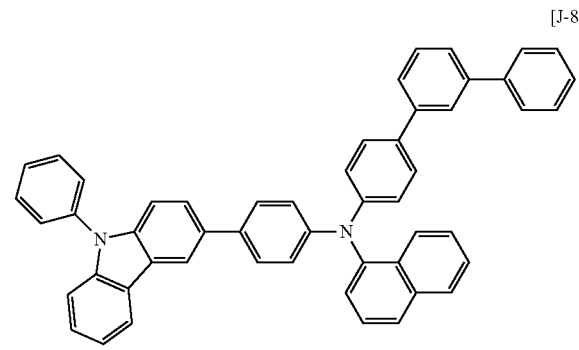
[J-9]
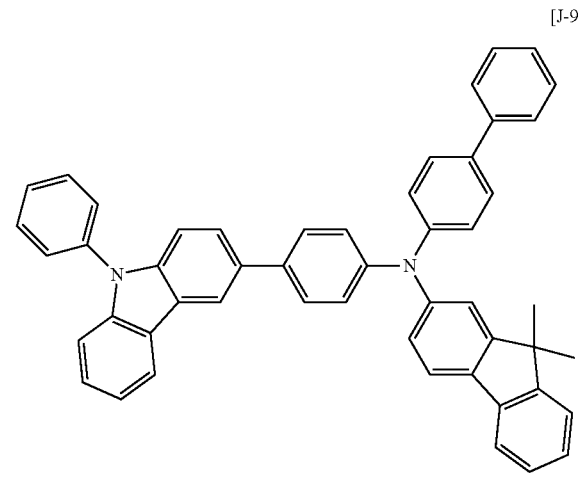
[J-10]
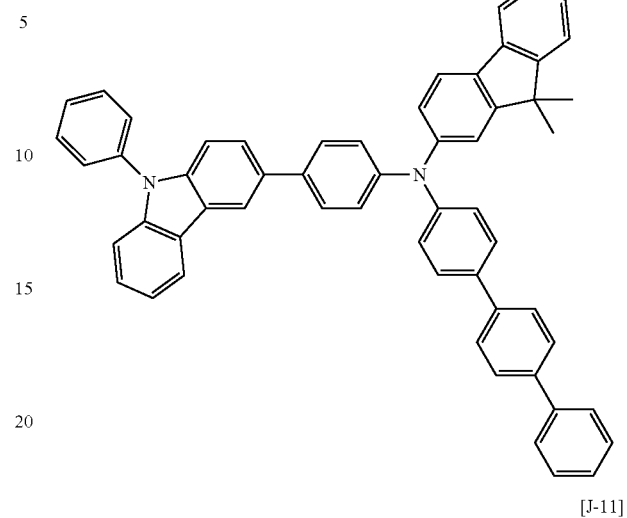
[J-11]
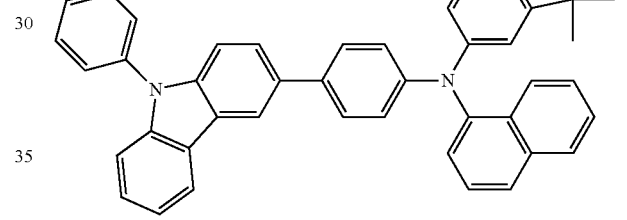
[J-12]
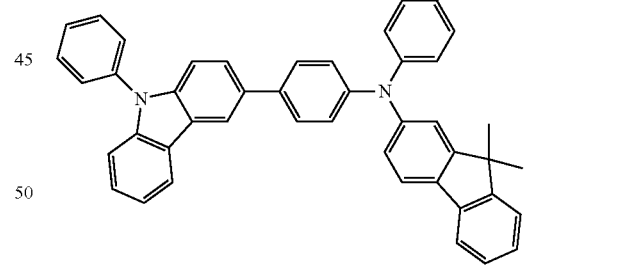
[J-13]
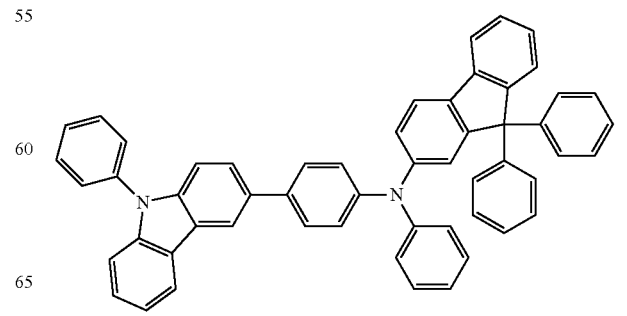

[J-14]
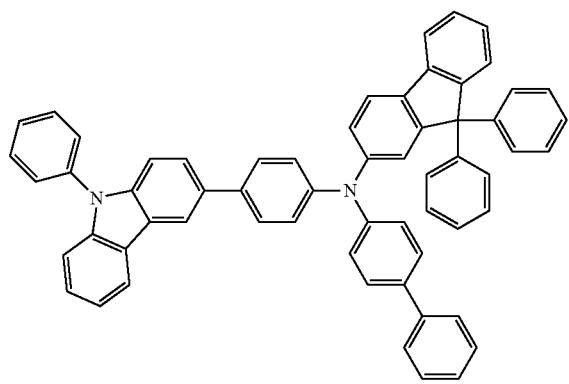
[J-15]
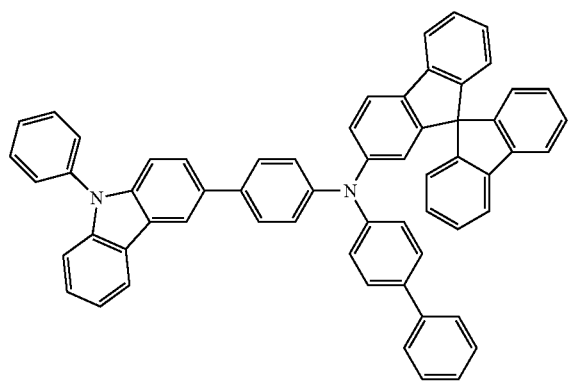
[J-16]
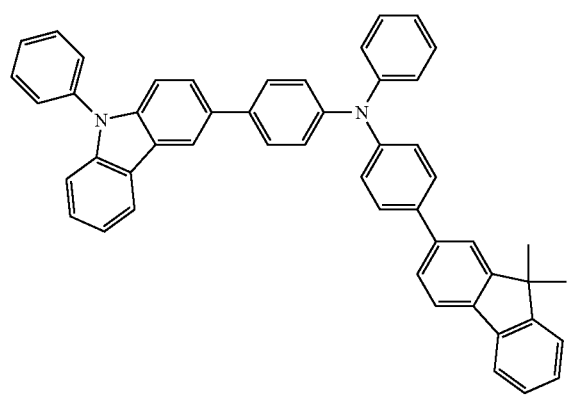
[J-17]
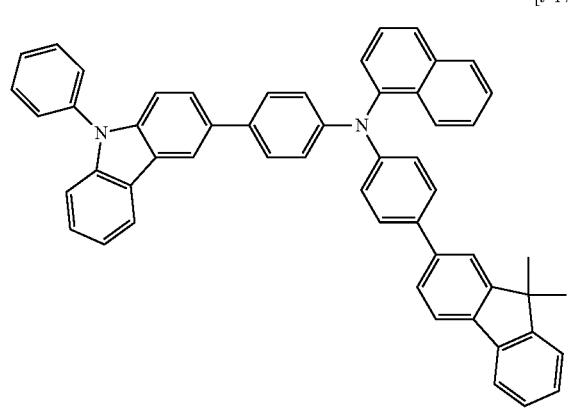
[J-18]
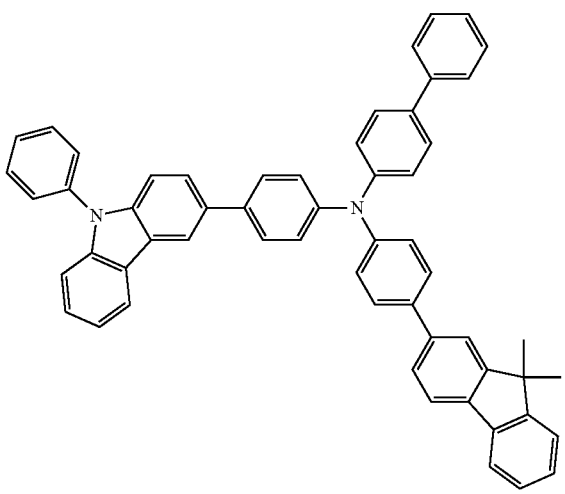
[J-19]
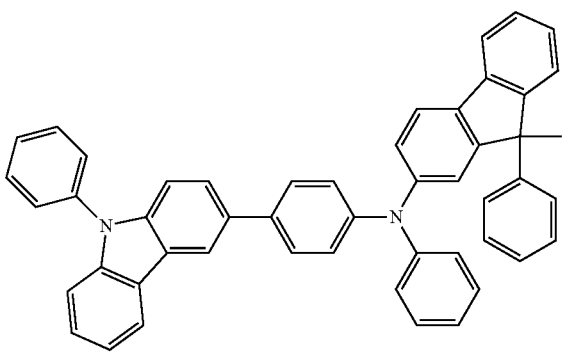
[J-20]
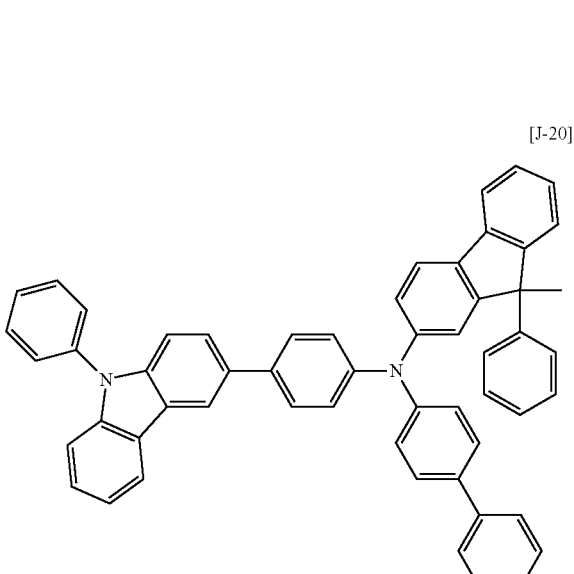

[J-21]
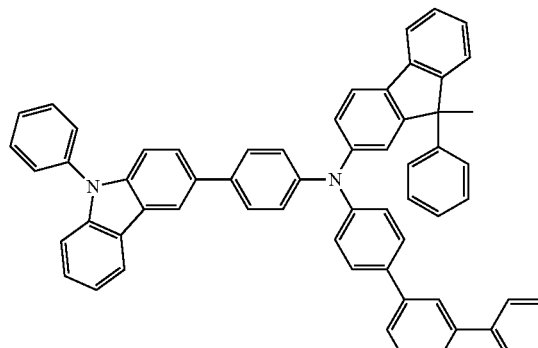
[J-22]
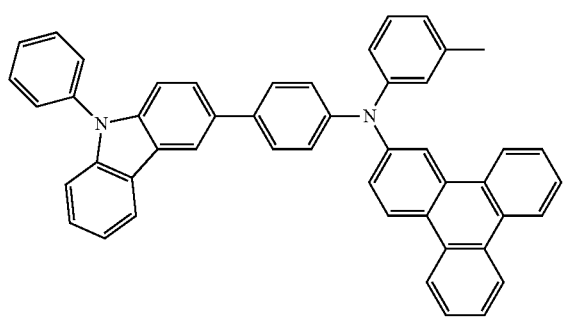
[J-23]
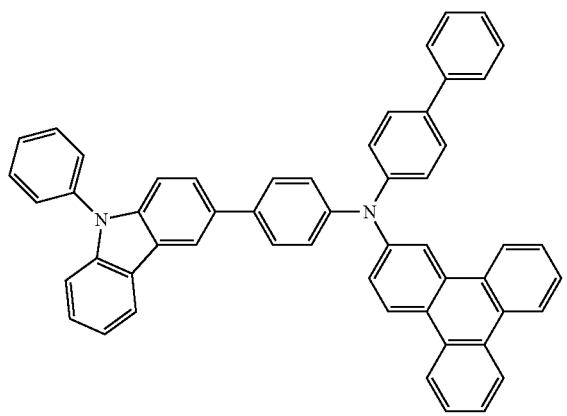
[J-24]
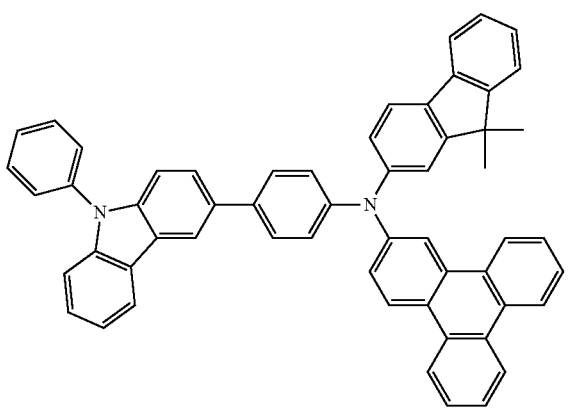
[J-25]
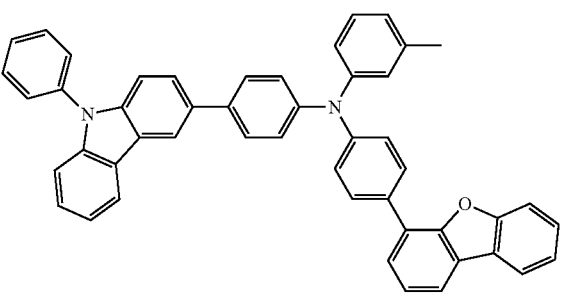
[J-26]
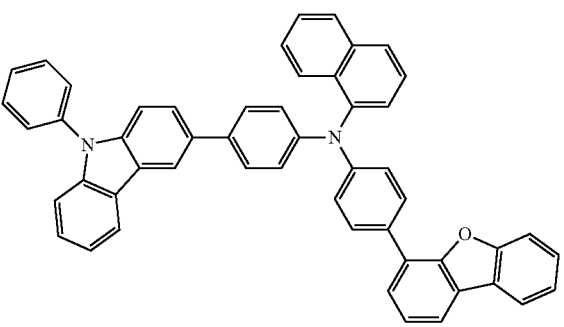
[J-27]
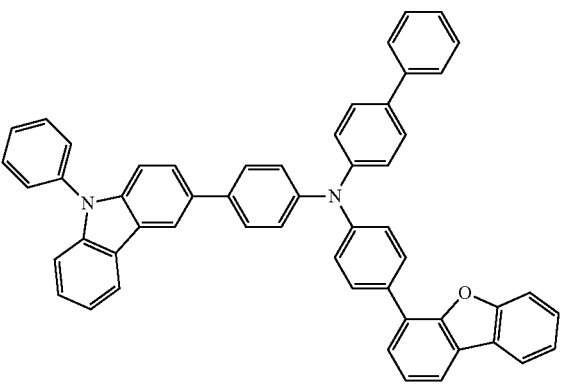
[J-28]
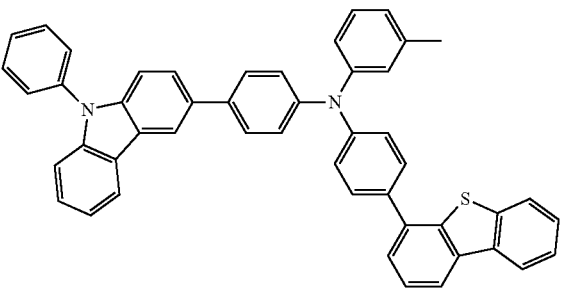

[J-29]
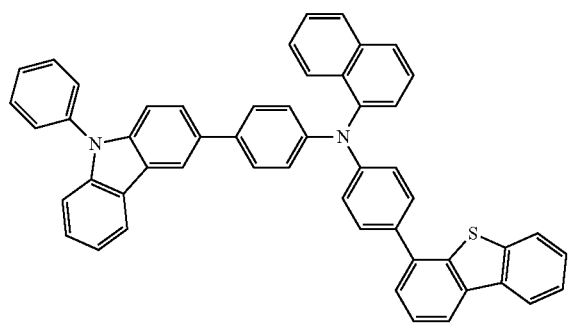
[J-30]
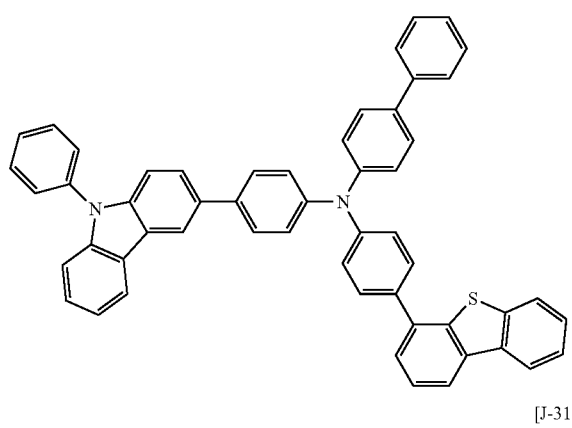
[J-31]
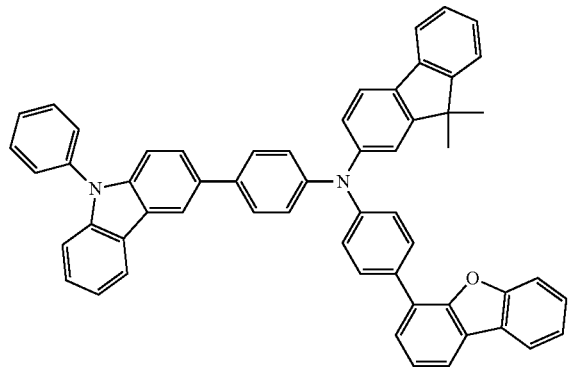
[J-32]
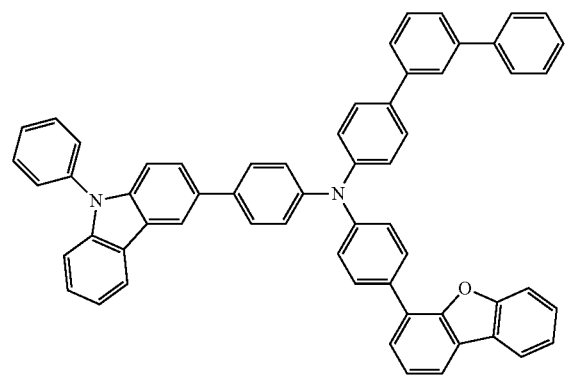
[J-33]
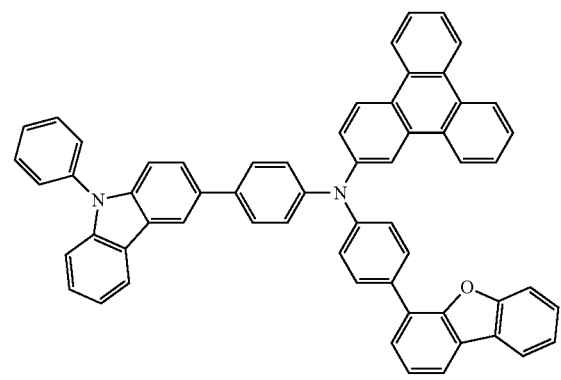
[J-34]
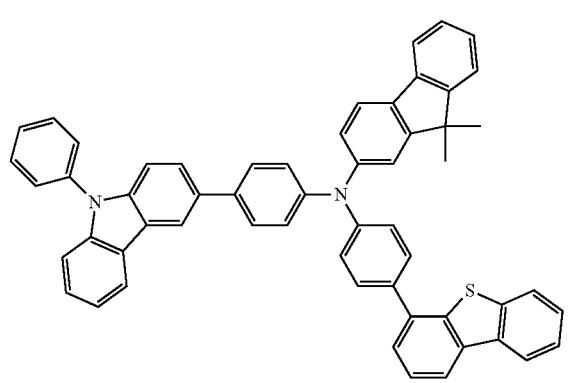
[J-35]
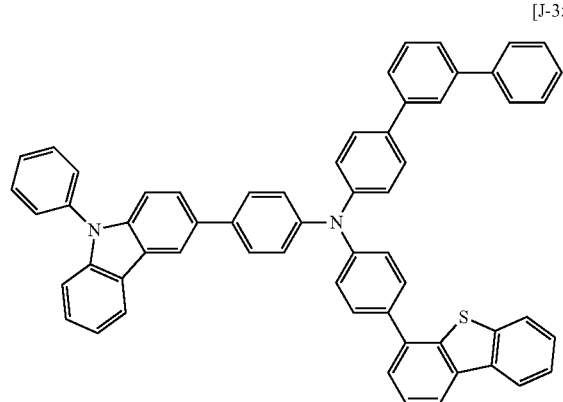
[J-36]

[J-37]
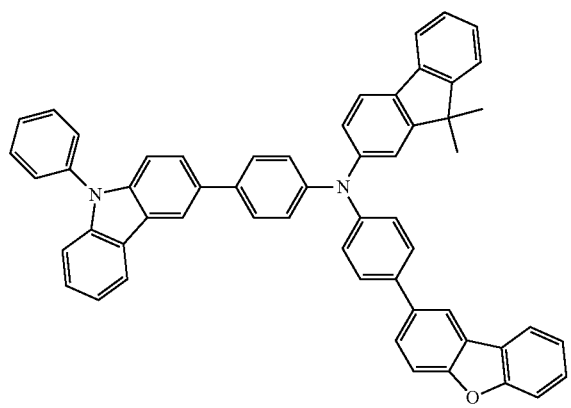
[J-38]
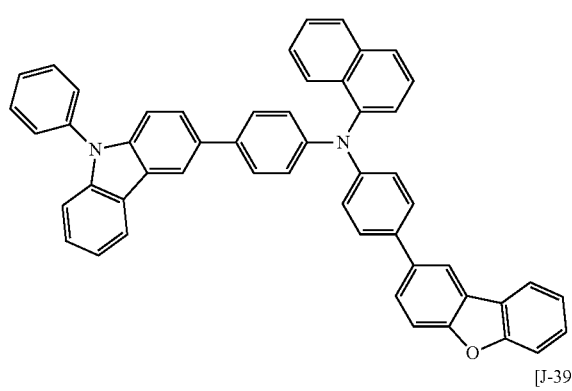
[J-39]
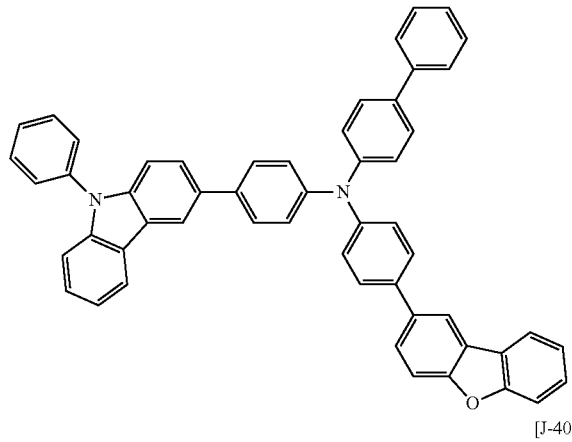
[J-40]
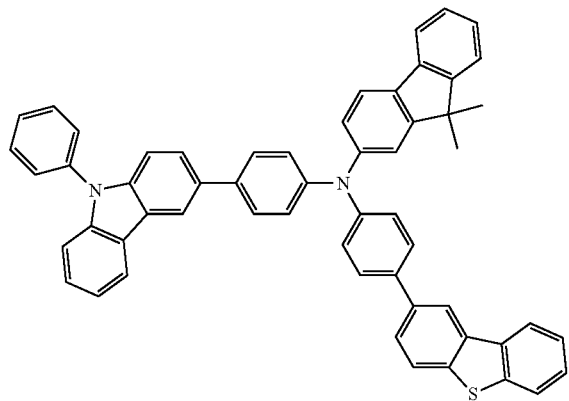
[J-41]
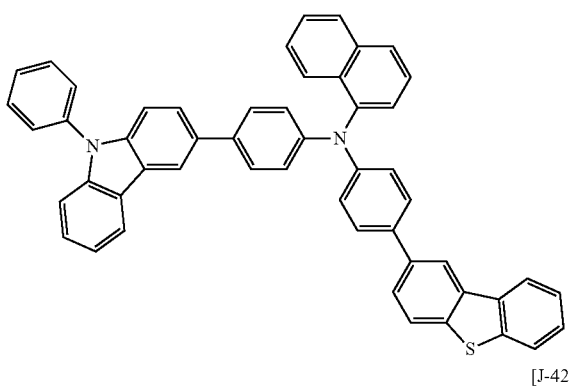
[J-42]
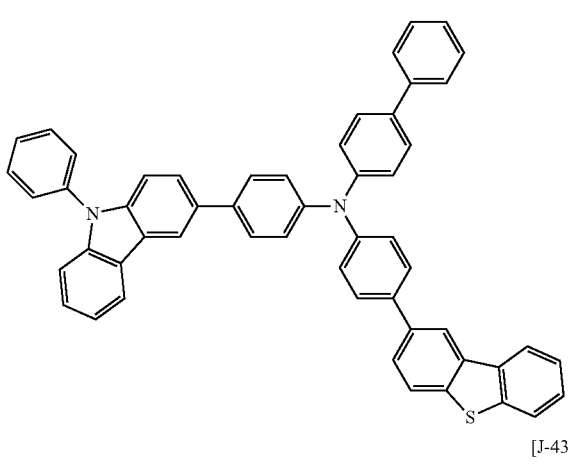
[J-43]
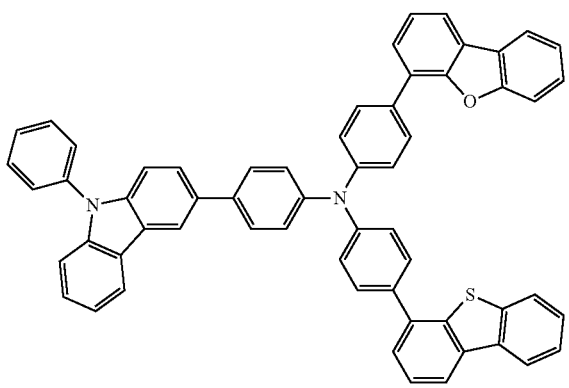
[J-44]
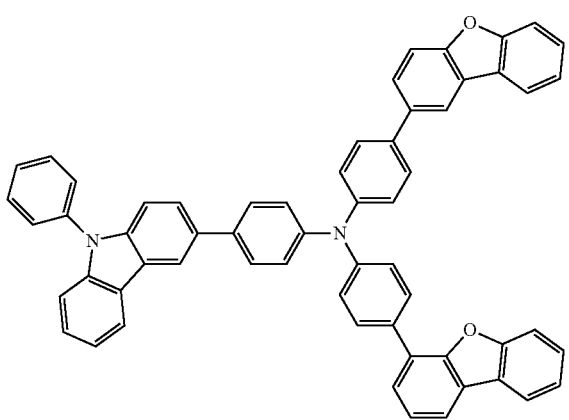

[J-45]
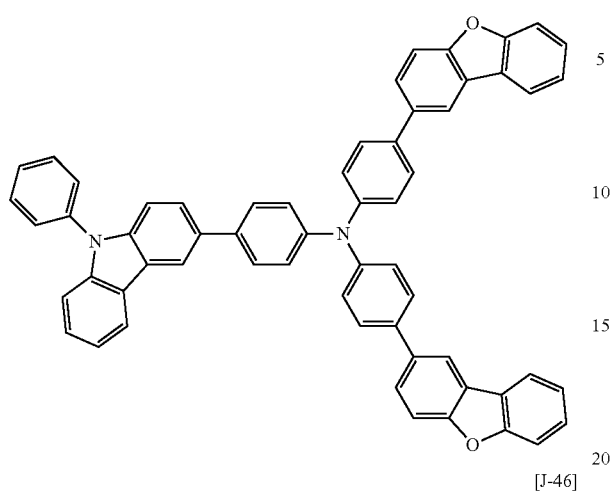
[J-46]
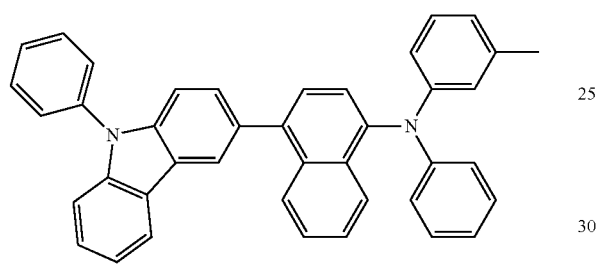
[J-47]
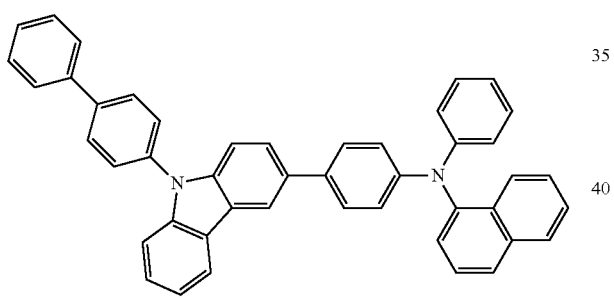
[J-48]
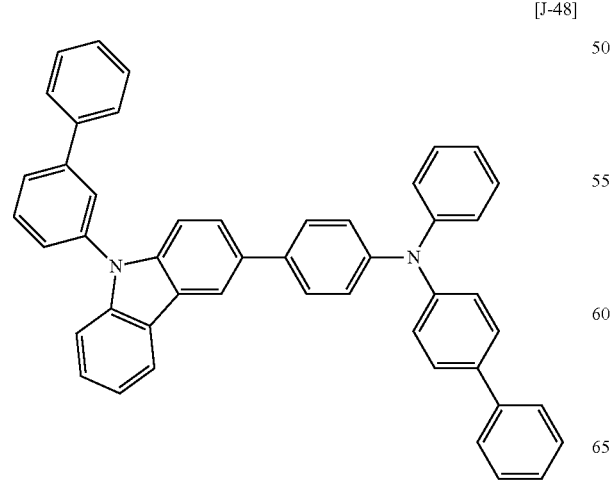
[J-49]
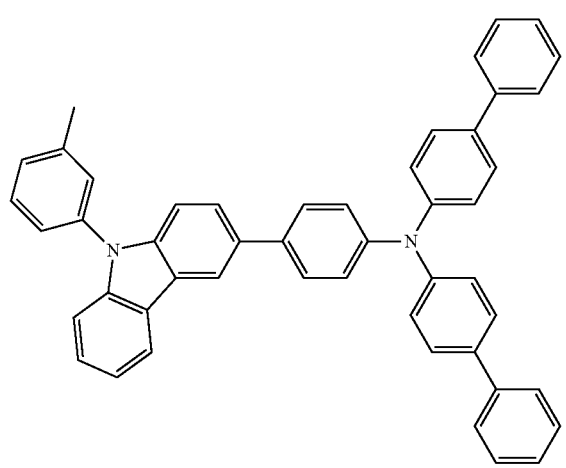
[J-50]
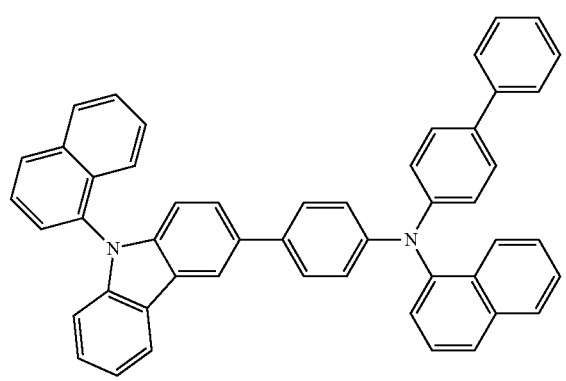
[J-51]
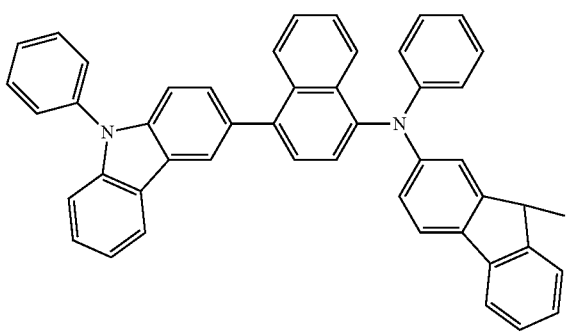

[J-52]
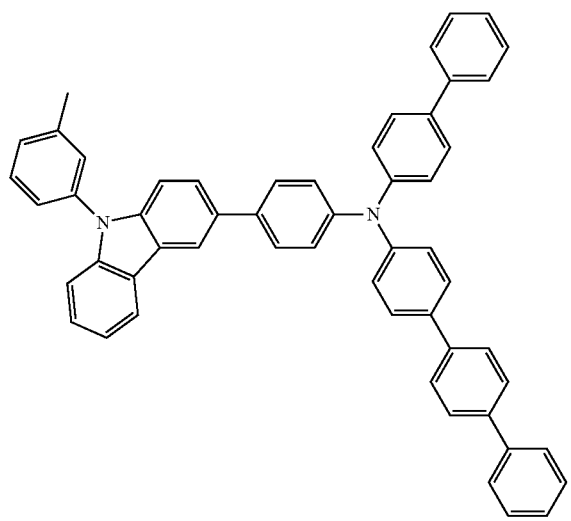
[J-55]
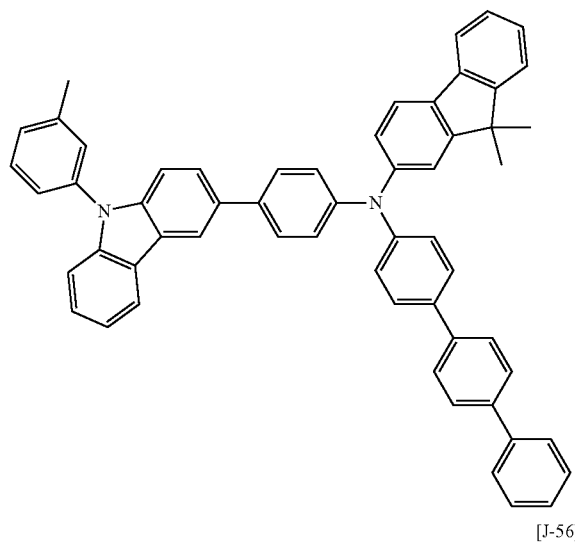
[J-53]
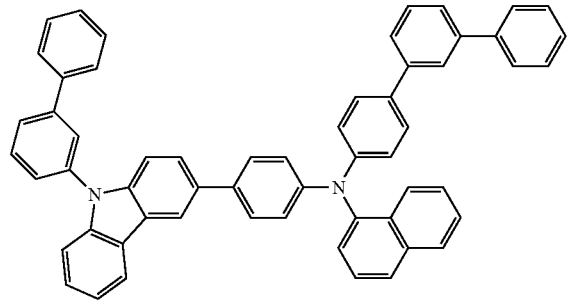
[J-56]
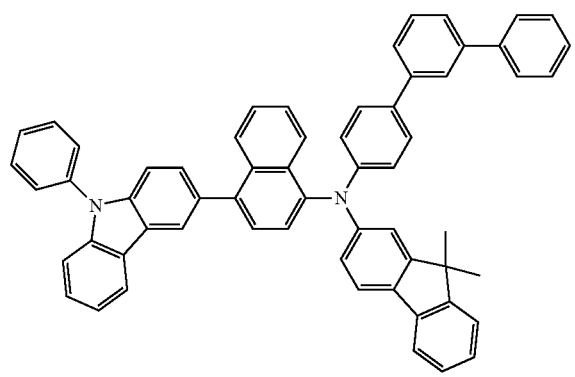
[J-54]
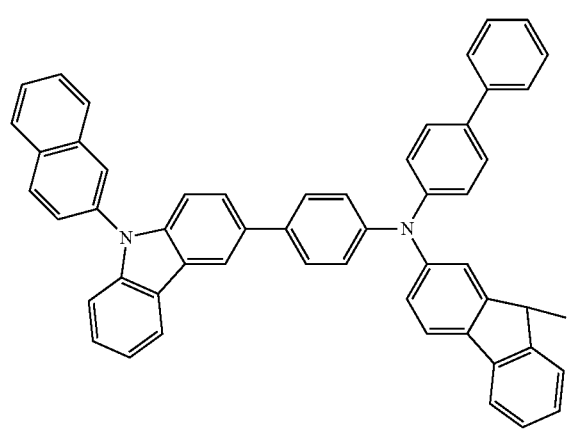
[J-57]
[J-58]

[J-59]
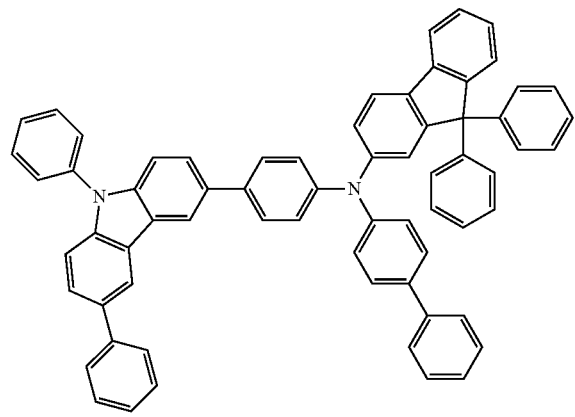
[J-62]
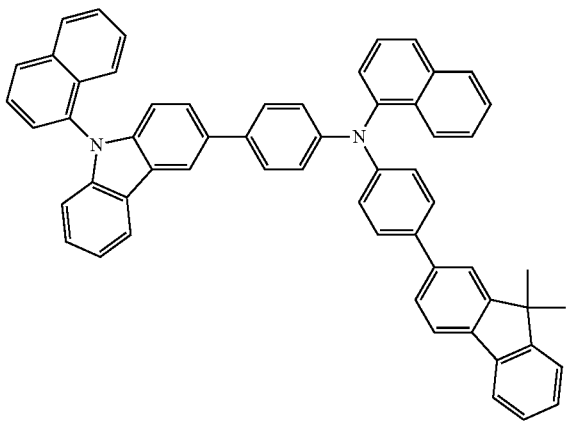
[J-60]
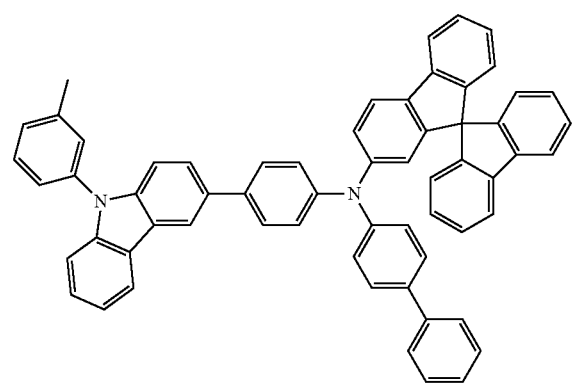
[J-63]
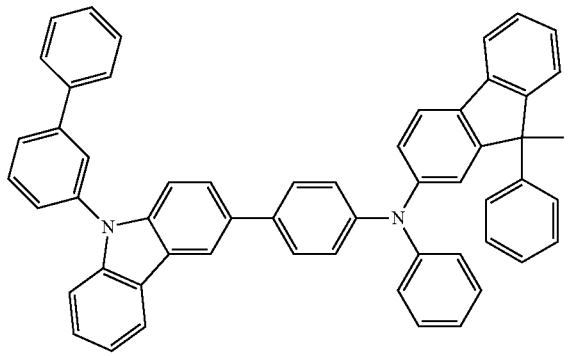
[J-61]
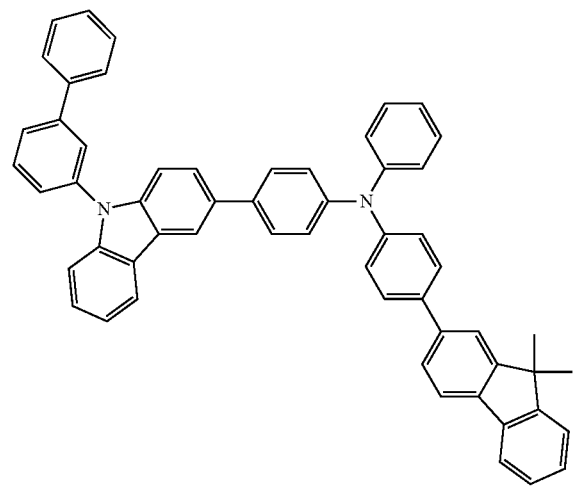
[J-64]

[J-65]
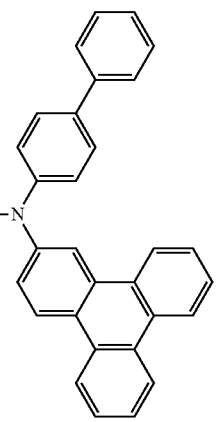
[J-66]
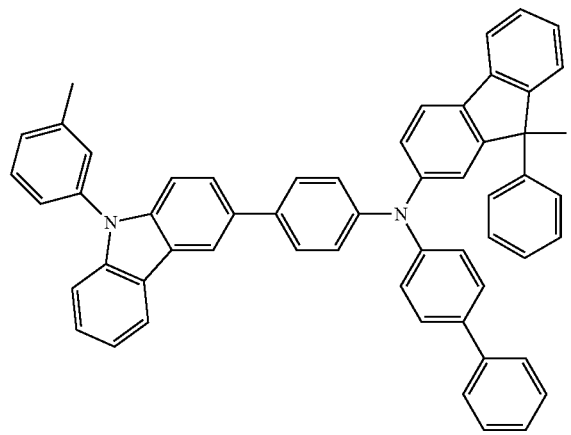
[J-67]
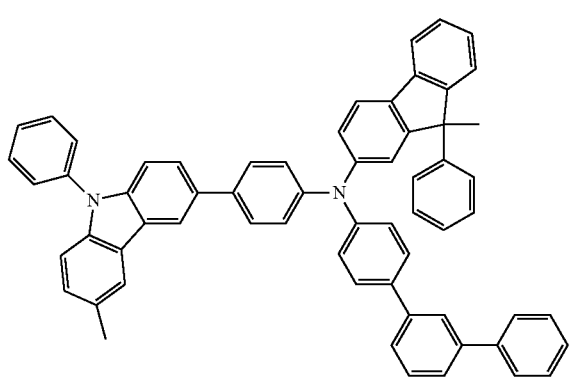
[J-68]
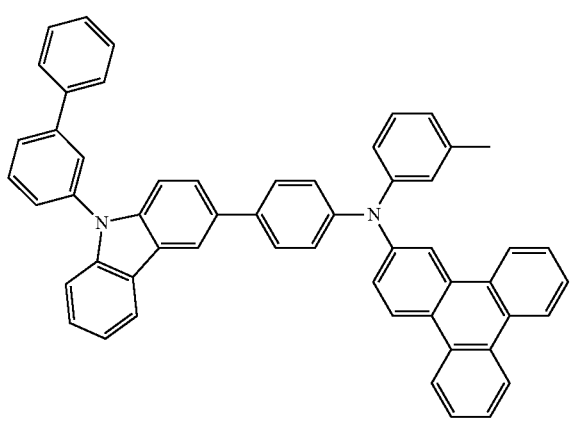
[J-69]
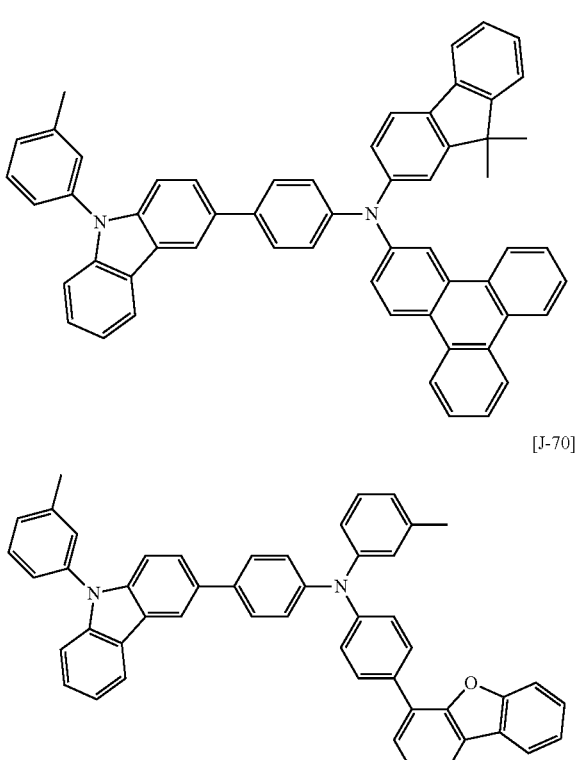
[J-70]
[J-71]
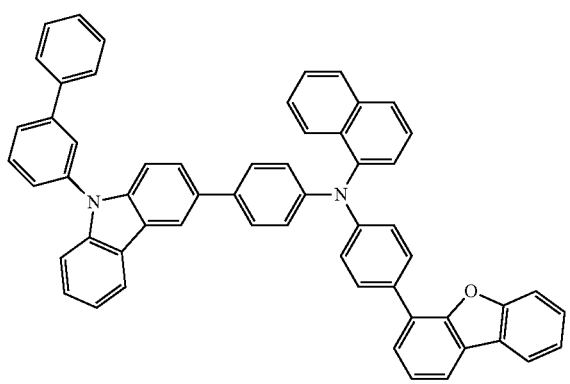

[J-72]
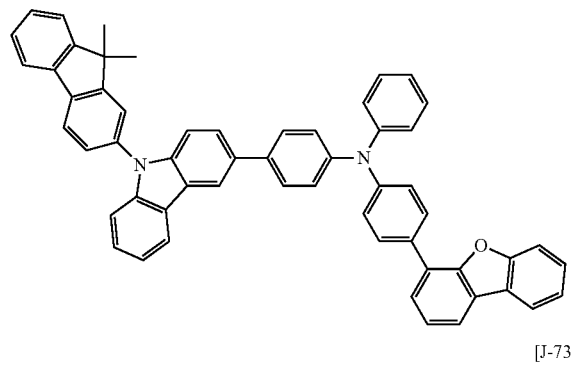
[J-76]
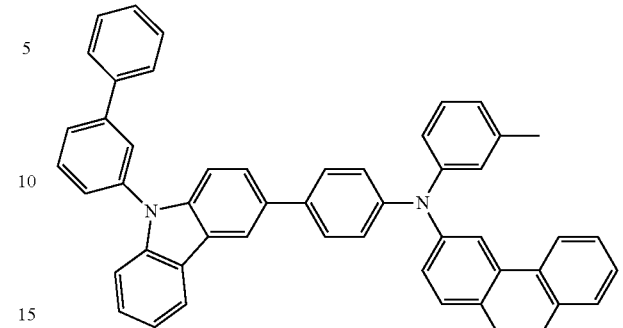
[J-73]
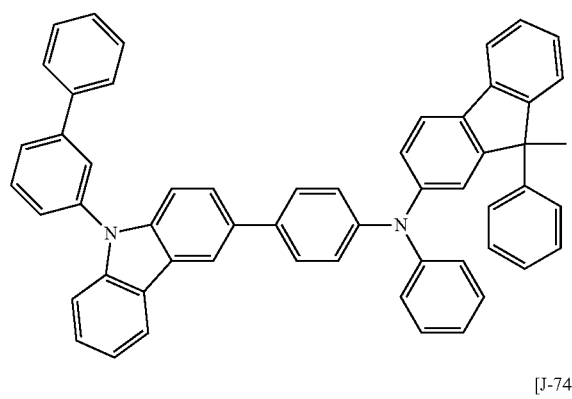
[J-77]
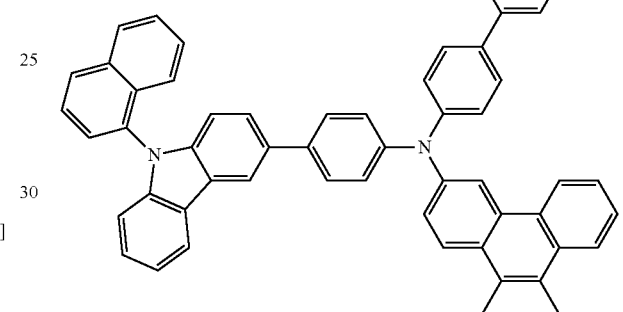
[J-74]
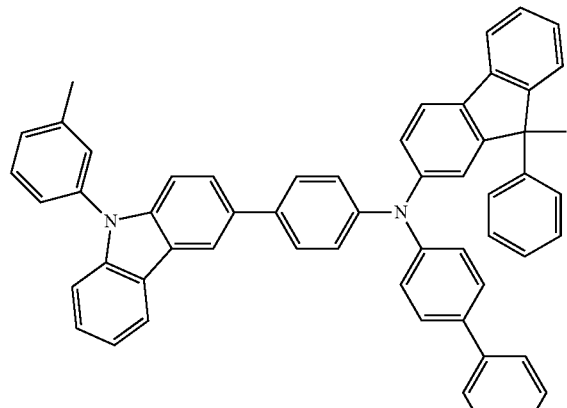
[J-78]
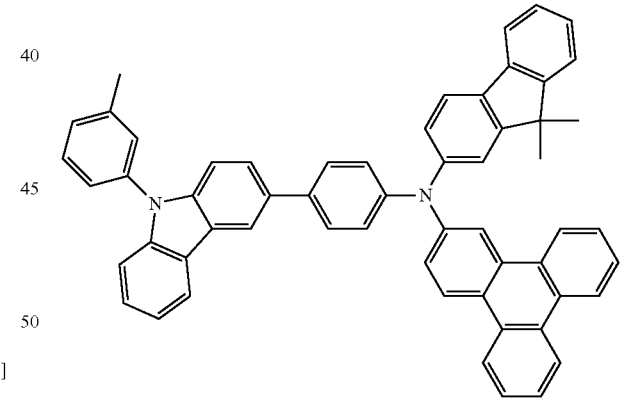
[J-75]
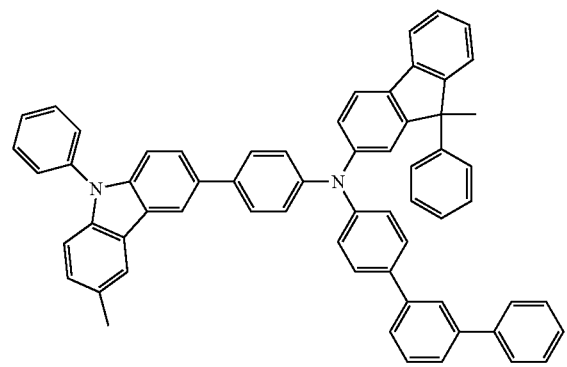
[J-79]
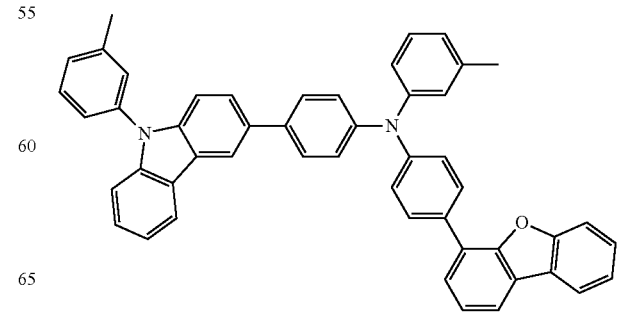

[J-80]
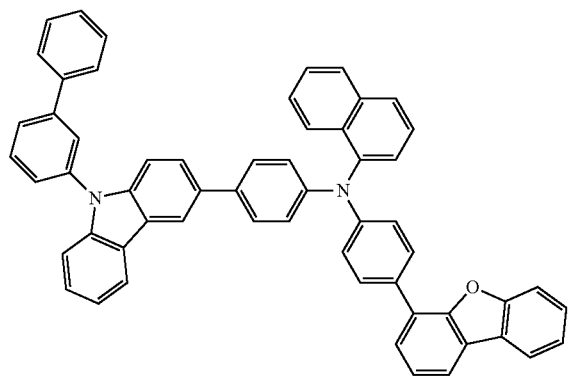
[J-81]
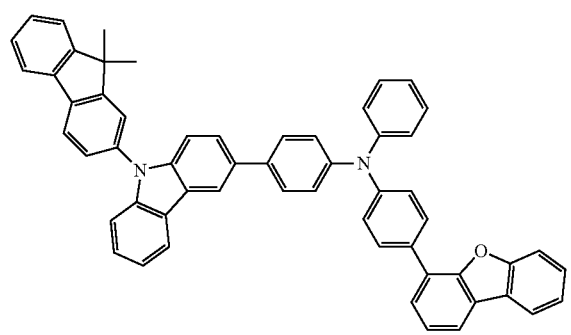
[J-82]
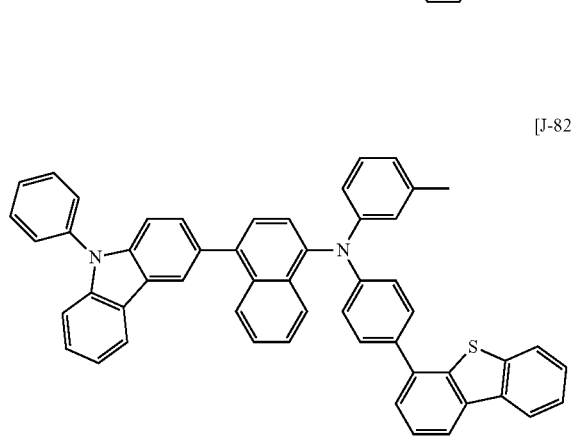
[J-83]
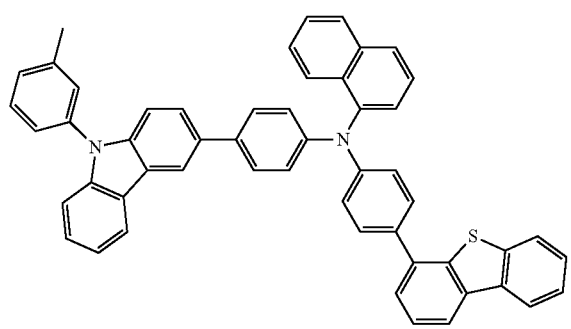
[J-84]
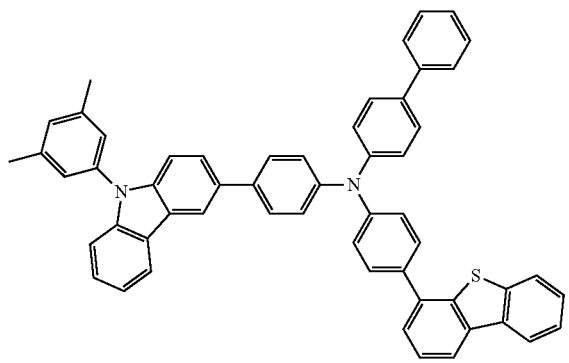
[J-85]
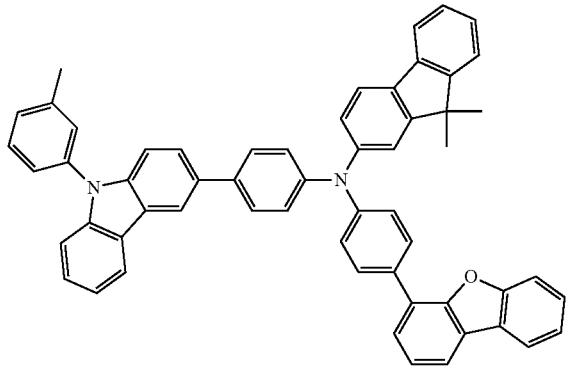
[J-86]
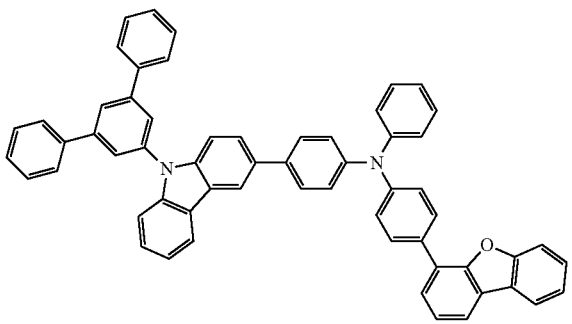
[J-87]
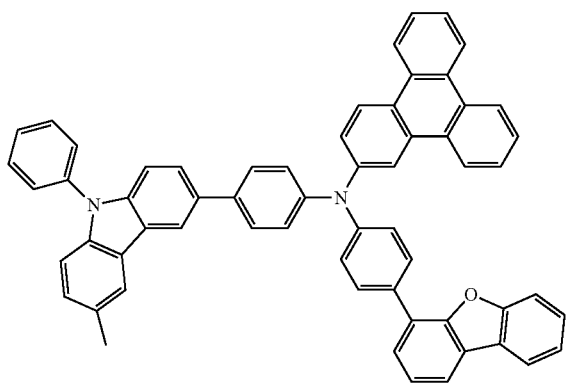

[J-88]
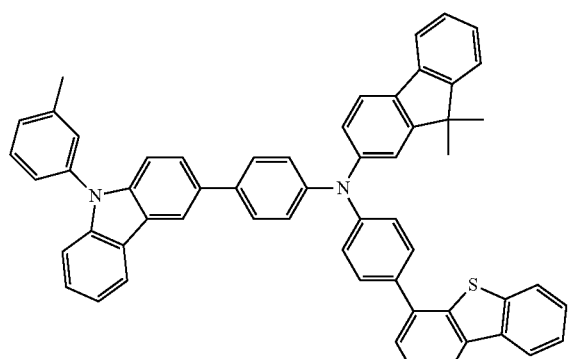
[J-92]
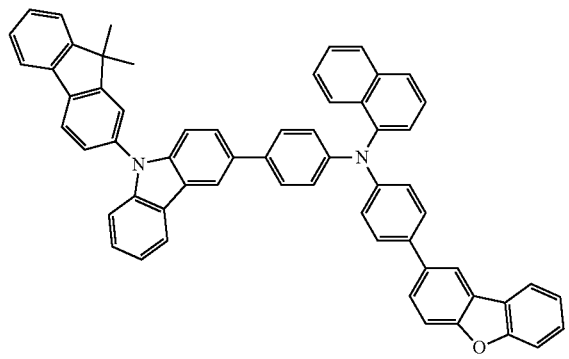
[J-89]
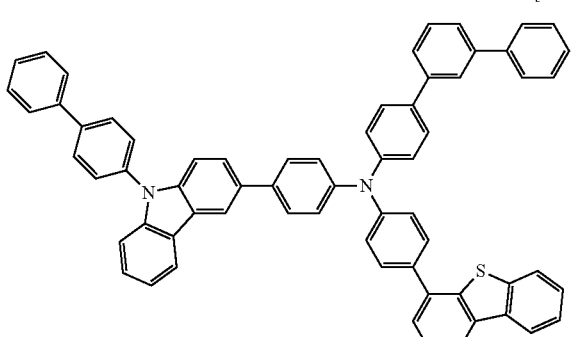
[J-93]
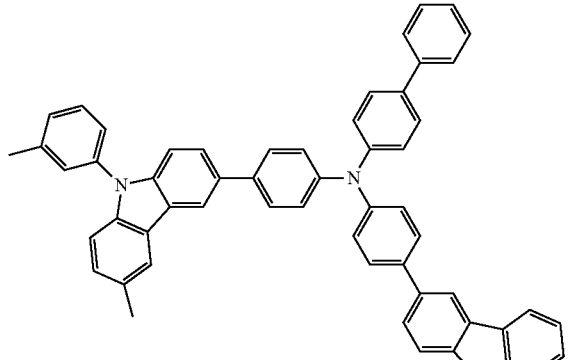
[J-90]
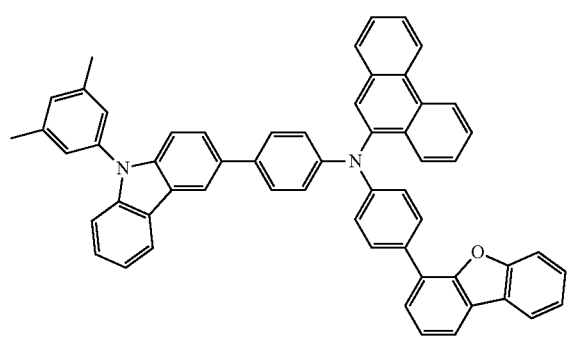
[J-94]
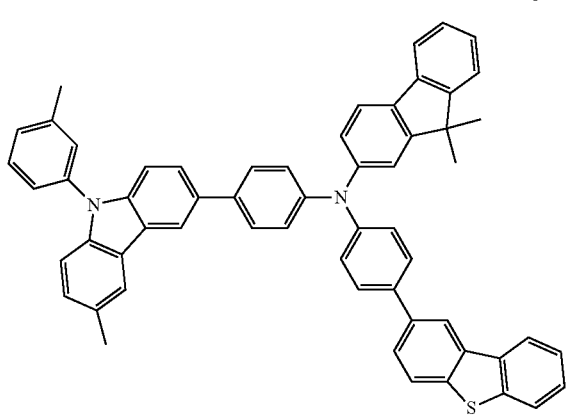
[J-91]
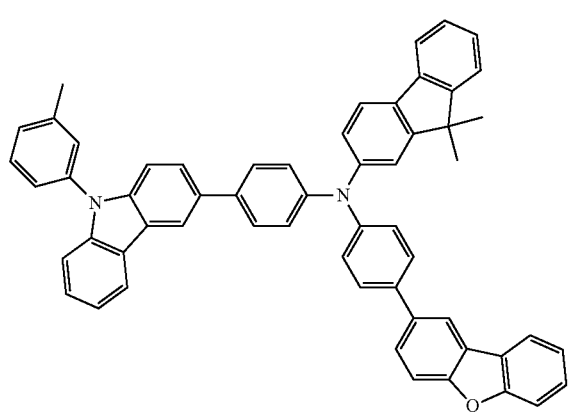
[J-95]
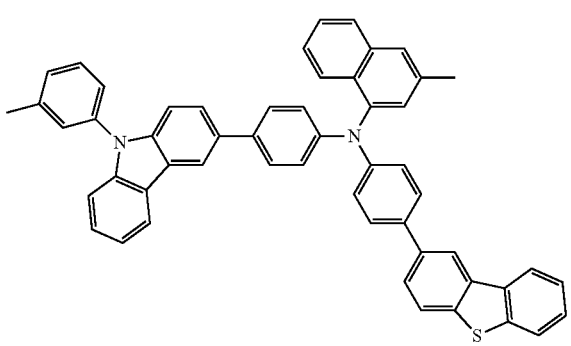

[J-96]
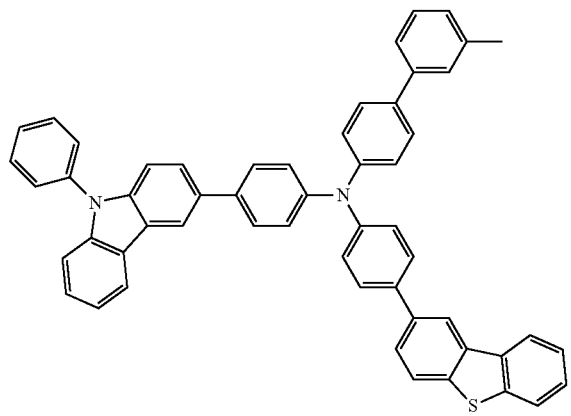
[J-97]
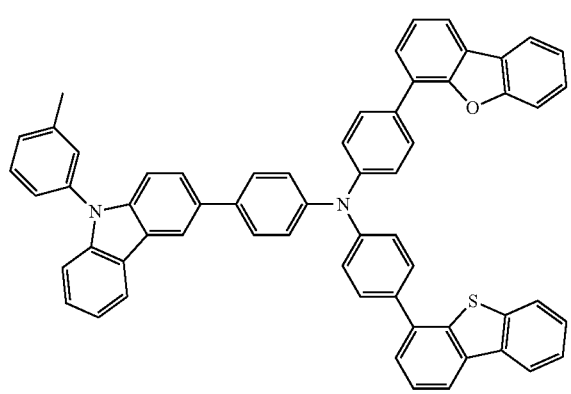
[J-98]
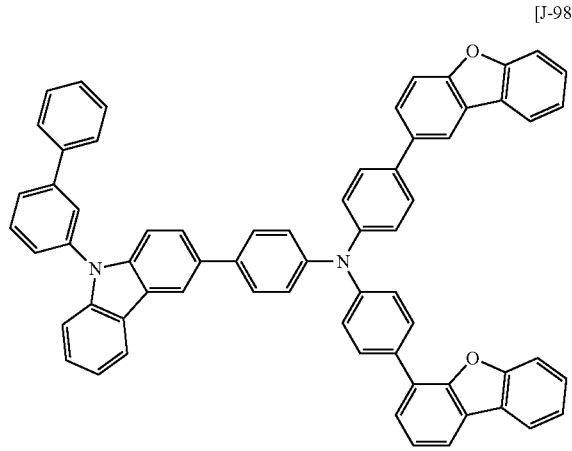
[J-99]
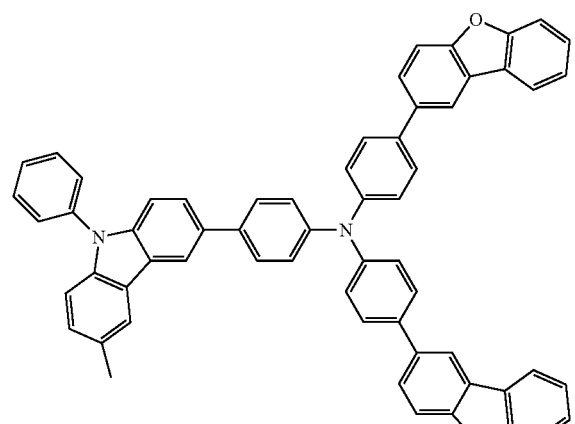
[J-100]
[J-101]
[J-102]
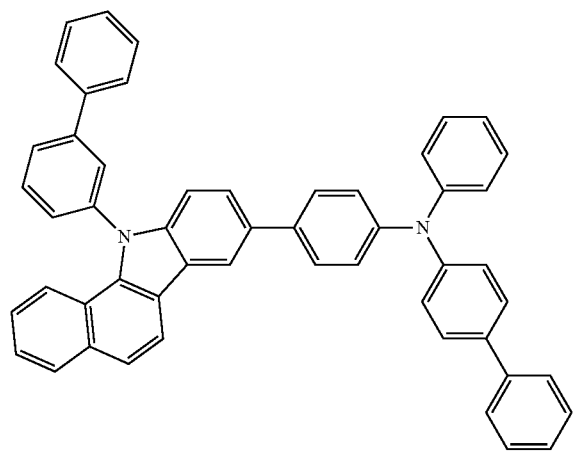

[J-103]
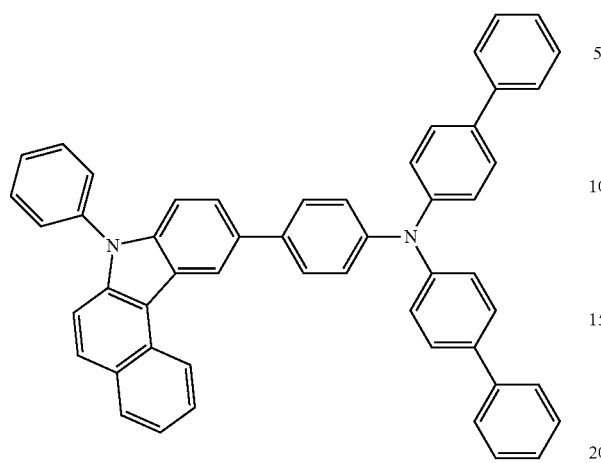
[J-106]
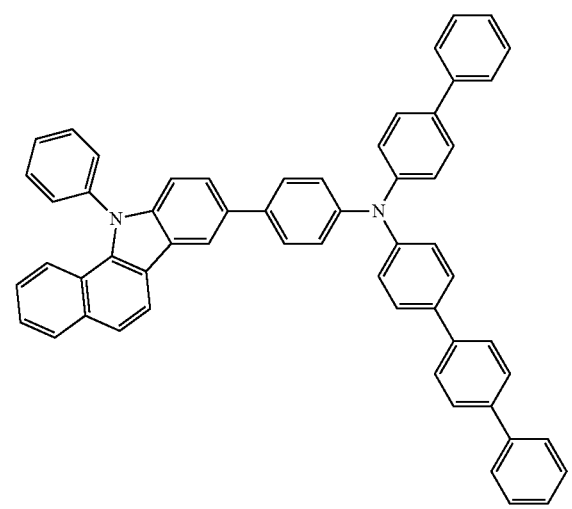
[J-104]
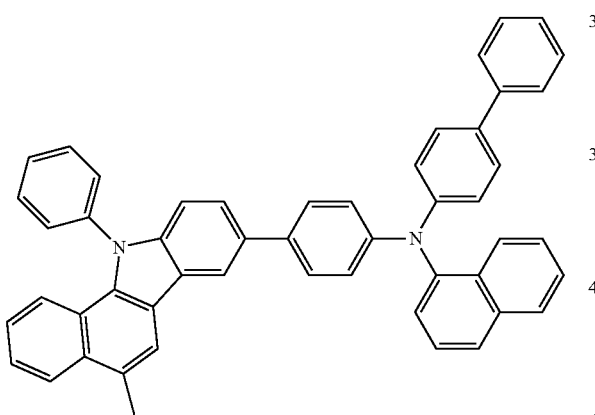
[J-107]
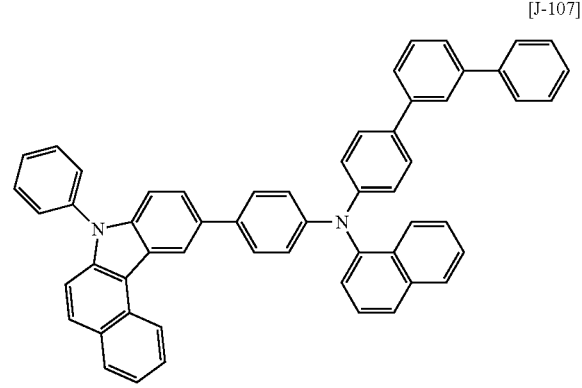
[J-105]
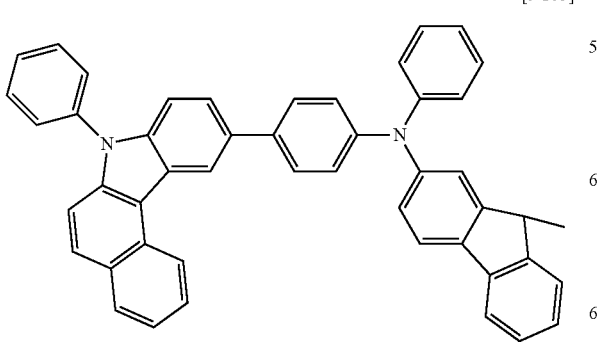
[J-108]
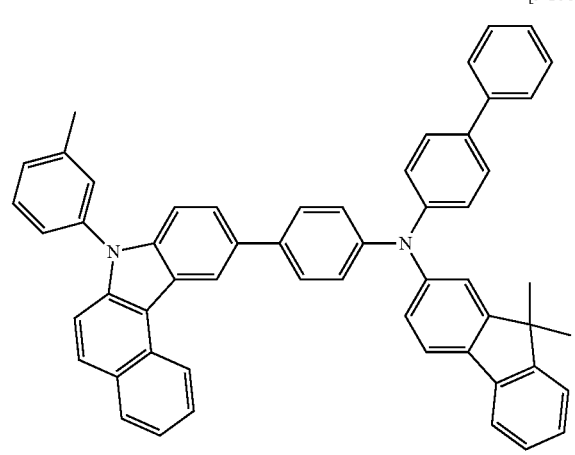

[J-109]
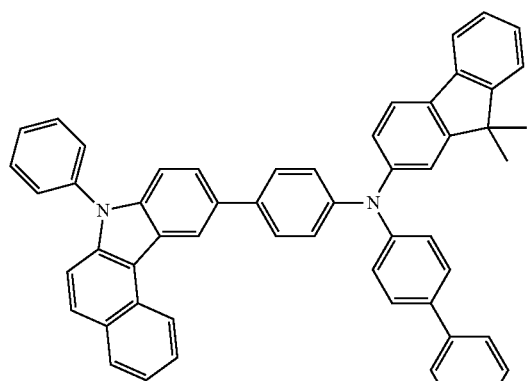
[J-110]
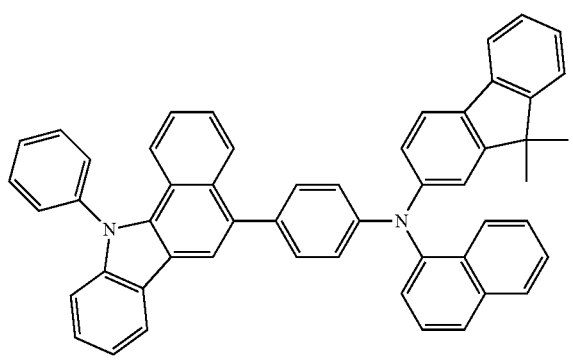
[J-111]
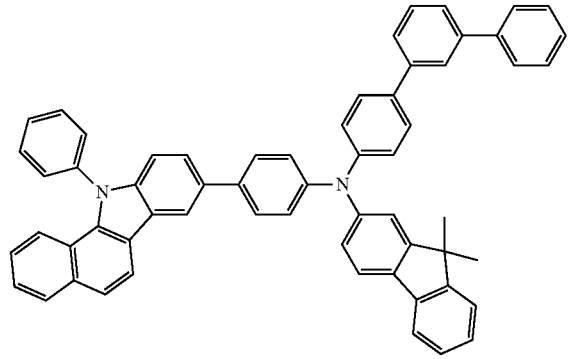
[J-112]
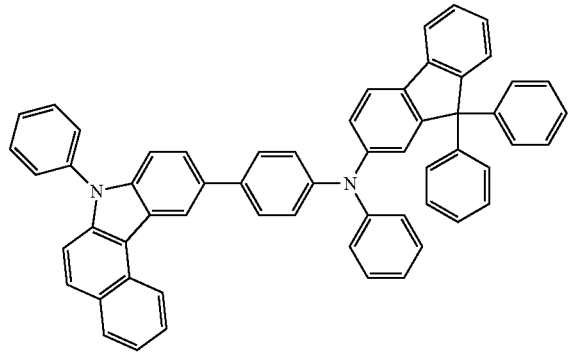
[J-113]
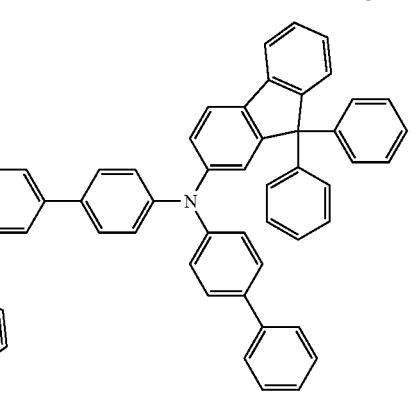
[J-114]
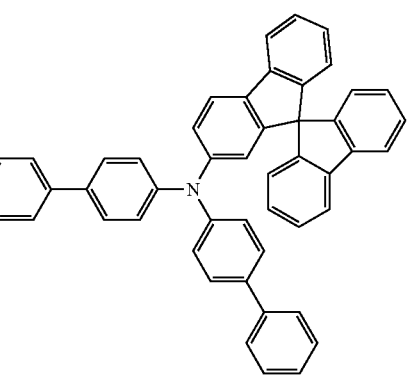
[J-115]
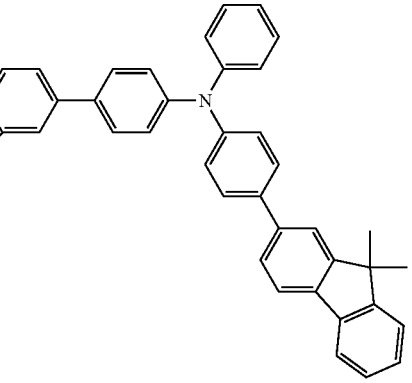
[J-116]
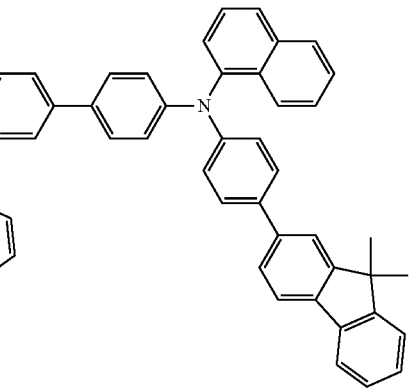

-continued
[J-117]
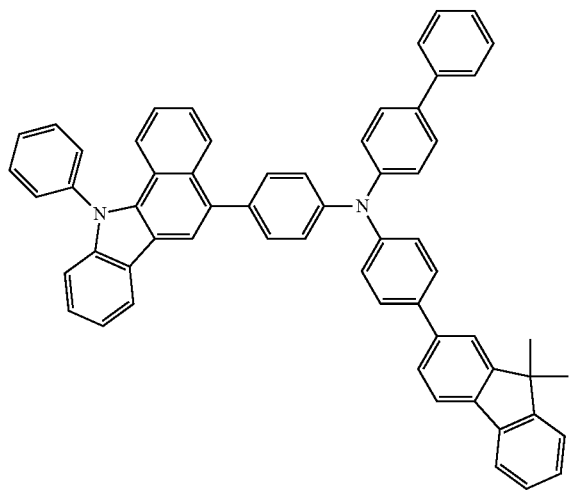
[J-118]
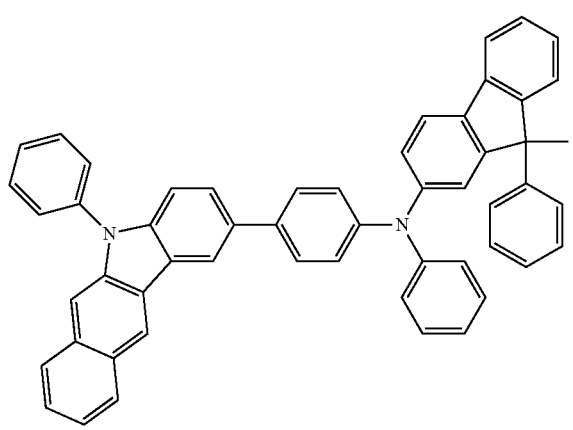
[J-119]
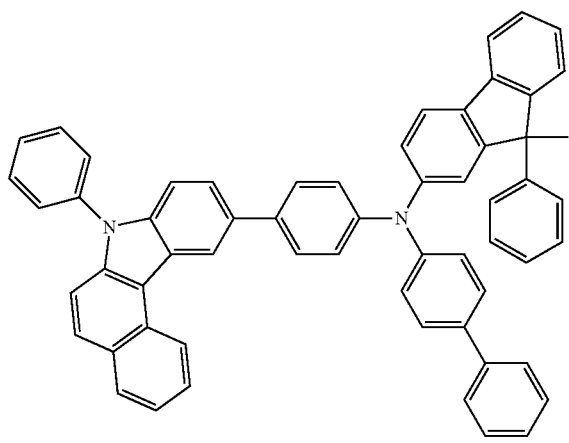
-continued
[J-120]
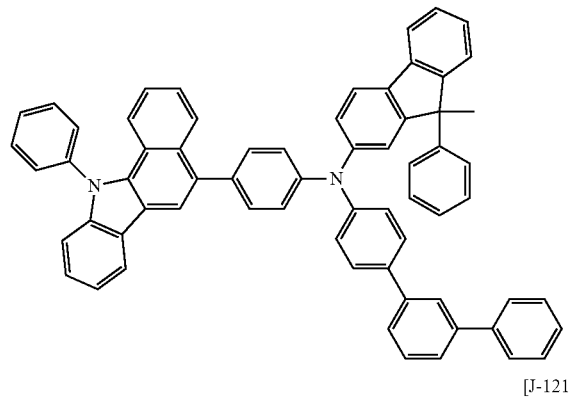
[J-121]
[J-122]
[J-123]

-continued
[J-124]
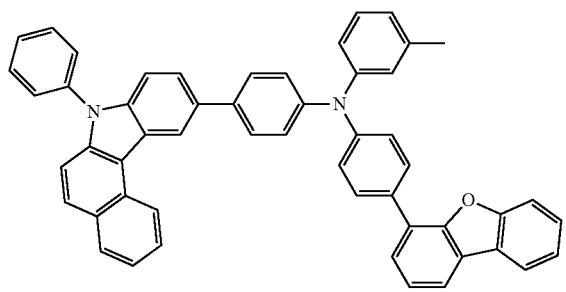
[J-125]
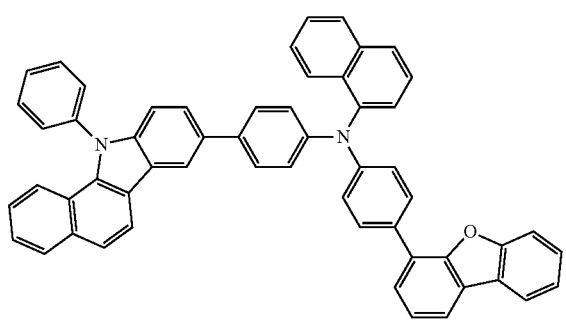
[J-126]
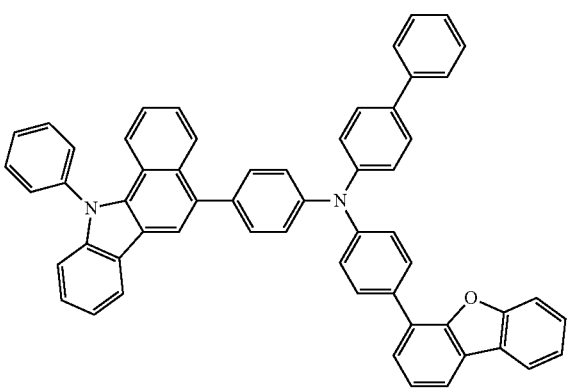
[J-127]
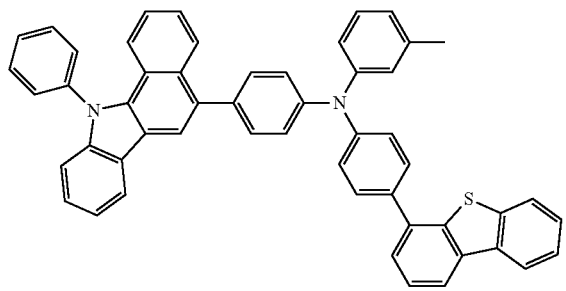
-continued
[J-128]
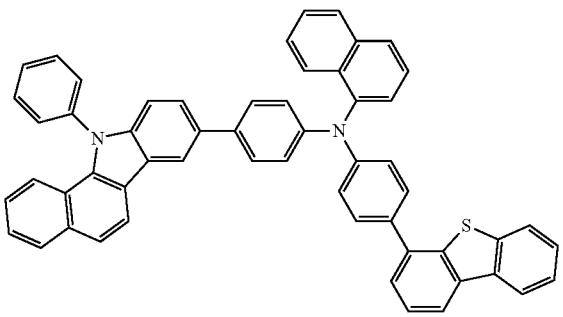
[J-129]
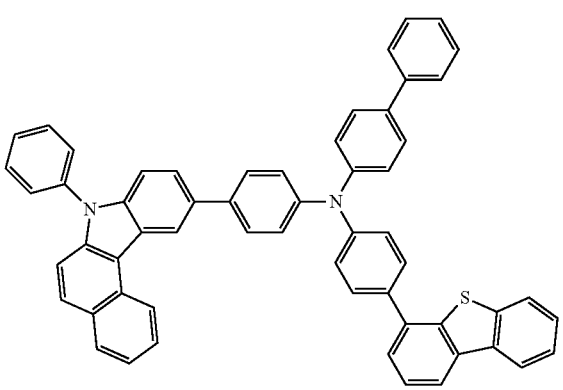
[J-130]
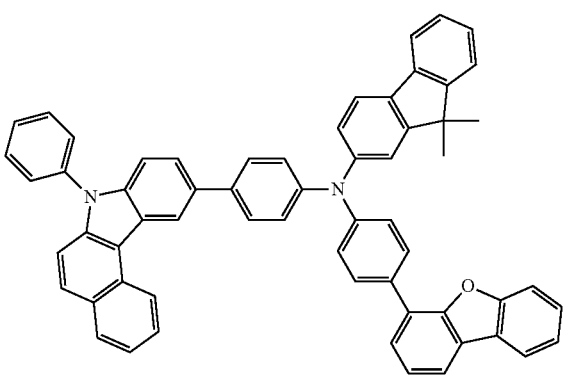
[J-131]
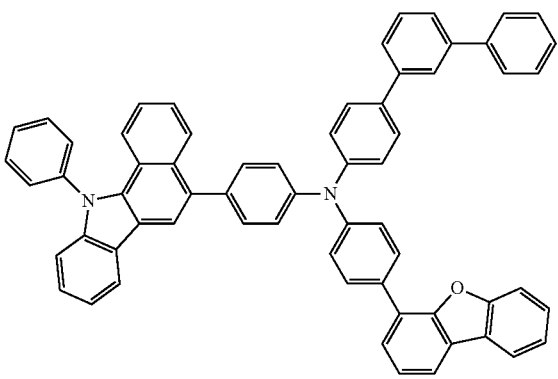

[J-132]
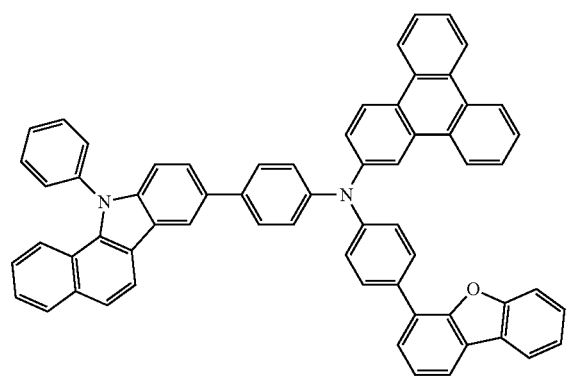
[J-133]
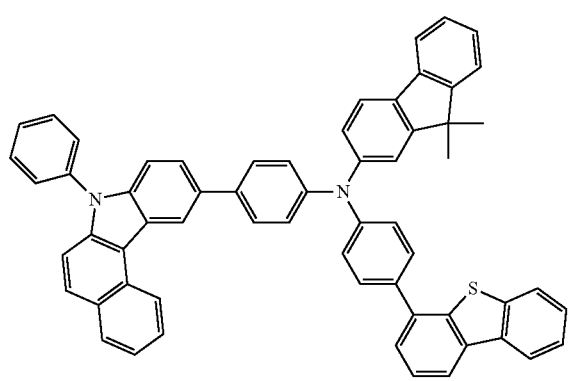
[J-134]
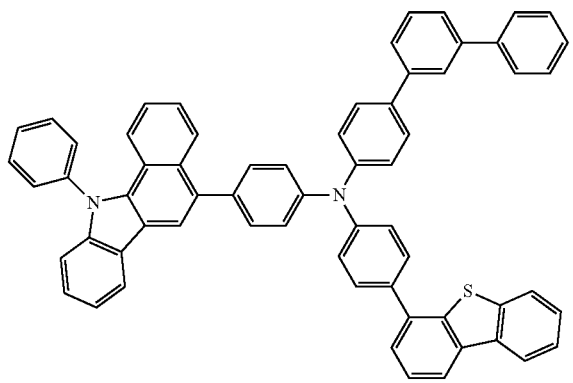
[J-135]
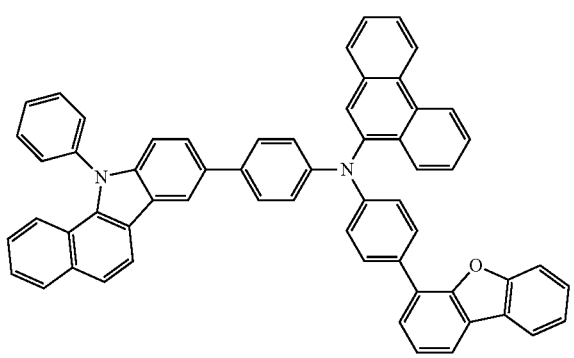
[J-136]
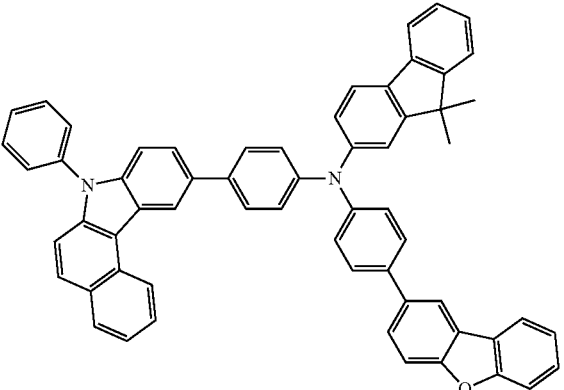
[J-137]
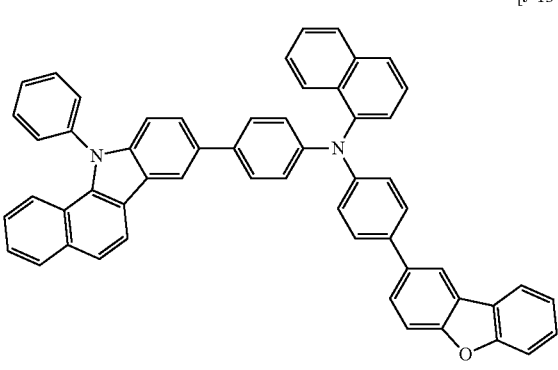
[J-138]
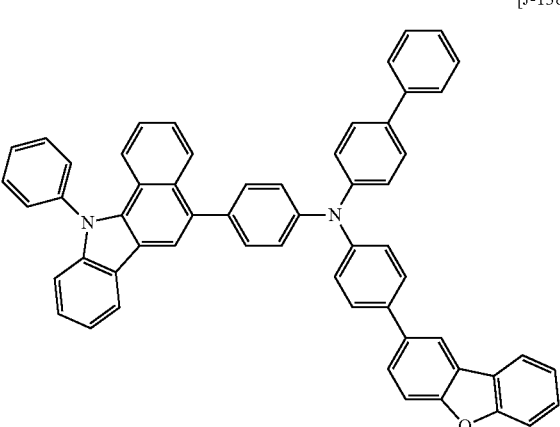
[J-139]
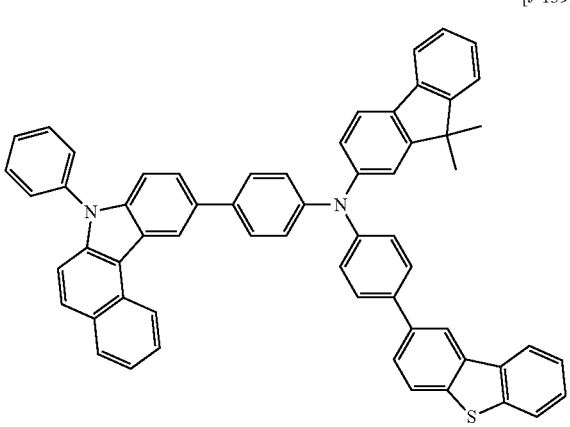

-continued

[J-140]
[J-141]
[J-142]
[J-143]
[J-144]

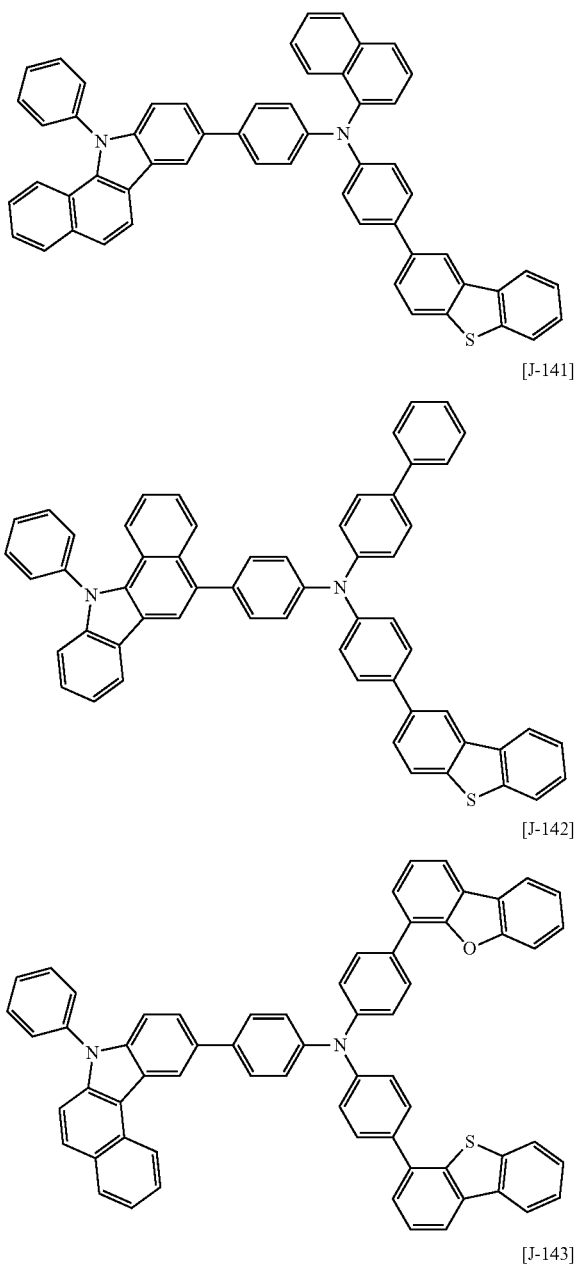
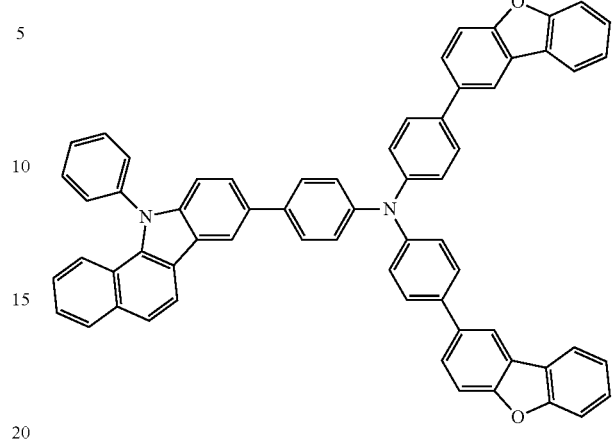

In FIGS. 1 to 3, the organic layer 105 may further include a hole injection layer, an electron blocking layer, an electron transport layer, an electron injection layer, and/or a hole blocking layer in addition to the emission layer 130 and the hole transport layer 140.

The organic light emitting diodes 100, 200, and 300 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to a display device, for example an organic light emitting diode (OLED) display.

Hereinafter, the embodiments are illustrated in more detail with reference to examples. These examples, however, are not in any sense to be interpreted as limiting the scope of the invention.

Hereinafter, starting materials and reactants used in Examples and Synthesis

Examples were purchased from Sigma-Aldrich Co. Ltd. or TCI Inc. as far as there in no particular comment.

SYNTHESIS OF INTERMEDIATE

Synthesis Example 1: Synthesis of Intermediate A

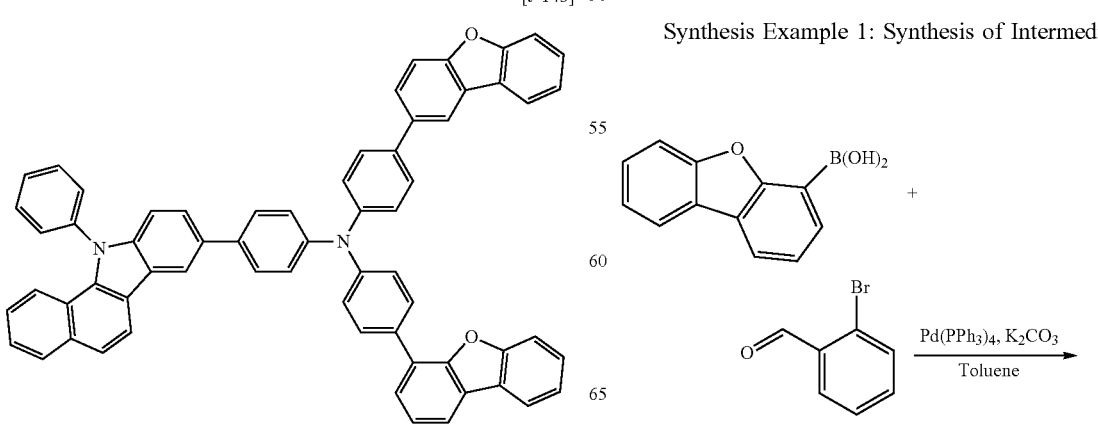

-continued

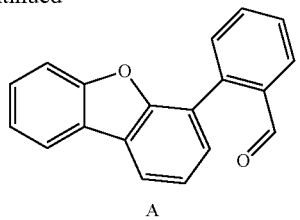

A 37.81 g (178.36 mmol) of 4-dibenzofuranboronic acid, 30 g (162.14 mmol) of 2-bromobenzaldehyde, 5.62 g (4.86 mmol) of tetrakis(triphenylphosphine)palladium (0), and 44.82 g (324.29 mmol) of potassium carbonate were suspended in 500 ml of toluene and 250 ml of distilled water round-bottomed flask and then, refluxed and stirred for 12 hours. After completing the reaction, the resultant was cooled down to room temperature and then, extracted. Subsequently, an organic layer therein was silica gel-filtered and concentrated, methyl alcohol was added thereto to produce a solid, and the solid was filtered and washed to obtain Intermediate A (39.87 g, 82%).

LC-Mass (Theoretical value: 272.30 g/mol, Measured value: M+=272 g/mol)

Synthesis Example 2: Synthesis of Intermediate B

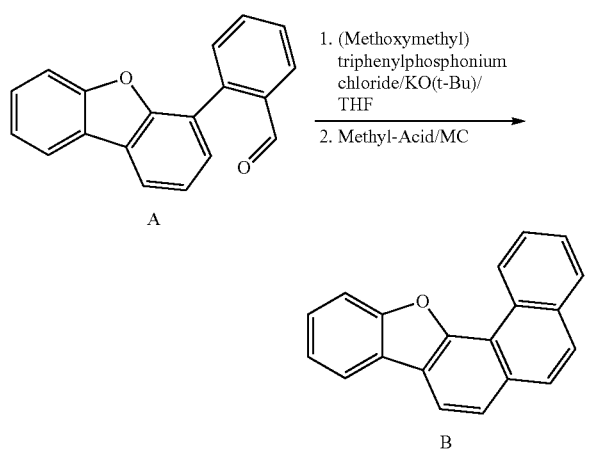

39.87 g (146.42 mmol) of the Intermediate A according to Synthesis Example 1 and 55.21 g (161.06 mmol) of (methoxymethyl)triphenyl phosphonium chloride were suspended in 500 ml of tetrahydrofuran in a round-bottomed flask and then, maintained at 0° C. Subsequently, 19.72 g (175.70 mmol) of potassium t-butoxide was slowly added thereto at 0° C., and the obtained mixture was stirred at room temperature for 12 hours. After completing the reaction, 600 ml of distilled water was added for an extraction, the extracted solution was concentrated, suspended in 500 ml of methylenechloride, dried with magnesium sulfate, filtered with silica gel, and concentrated again. The concentrated reaction solution was dissolved in 200 ml of methylenechloride, 15 g of methanesulfonic acid was slowly added thereto, and the mixture was stirred at room temperature for 12 hours. After completing the reaction, a solid produced therein was filtered, washed with 200 ml of distilled water and 200 ml of methanol, and dried to obtain Intermediate B (24.34 g, 62%).

LC-Mass (Theoretical value: 272.30 g/mol, Measured value: M+=272 g/mol)

Synthesis Example 3: Synthesis of Intermediate C

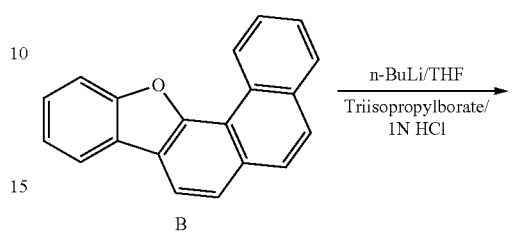

B

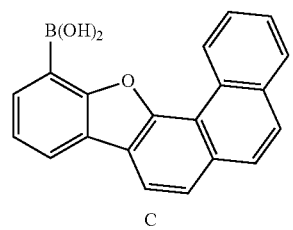

C 24.34 g (90.72 mmol) of the Intermediate B according to Synthesis Example 2 was dissolved in 250 ml of THF in a round-bottomed flask and cooled down to −78° C. 43.5 ml (108.86 mmol) of n-BuLi (2.5M in Hex) was added thereto in a dropwise fashion, and the obtained mixture was stirred at room temperature for 16 hours. After cooled down to −78° C., 25 ml (108.86 mmol) of triisopropylborate was added thereto, and the mixture was stirred at room temperature for 12 hours. When the reaction was complete, 1N HCl was added thereto, the mixture was stirred for one hour, and a solid produced therein was filtered and washed with distilled water and acetone to obtain Intermediate C (22 g, 78%).

LC-Mass (Theoretical value: 312.13 g/mol, Measured value: M+=312 g/mol)

Synthesis Example 4: Synthesis of Intermediate D

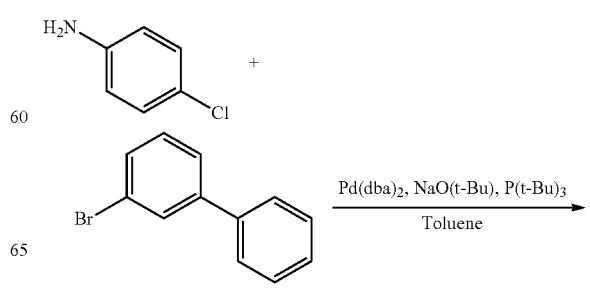

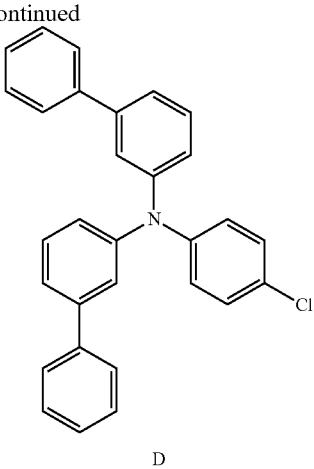

D 15 g (117.58 mmol) of 4-chloroaniline, 65.78 g (282.20 mmol) of 3-bromobiphenyl, 3.38 g (5.88 mmol) of Pd(dba)₂, 2.38 g (11.76 mmol) of P(t-Bu)₃, and 33.9 g of NaO(t-Bu) were suspended in 500 ml of toluene in a round-bottomed flask and then, refluxed and stirred for 12 hours. When the reaction was complete, distilled water was added thereto, the mixture was stirred and extracted for 30 minutes, and only organic layer therein was silica gel-columned (hexane/dichloromethane=9:1 (v/v)) to obtain Intermediate D (31 g, 61%).

LC-Mass (Theoretical value: 431.96 g/mol, Measured value: M+=431 g/mol)

Synthesis Example 5: Synthesis of Intermediate E

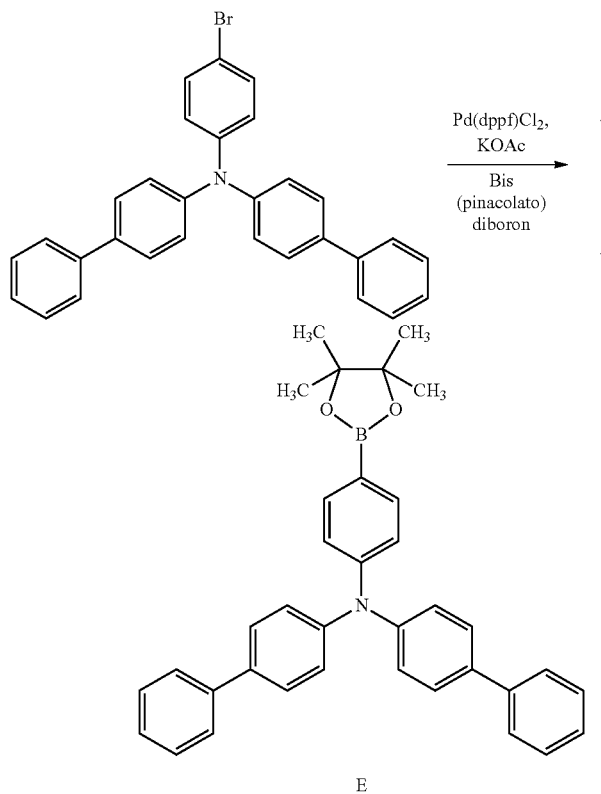

E 20 g (476.41 mmol) of N-(4-bromophenyl)-N,N-bis(1,1'-biphenyl-4-yl)amine, 1.03 g (1.26 mmol) of Pd(dppf)Cl₂, 12.8 g (50.38 mmol) of bis(pinacolato)diboron, and 12.36 g (125.94 mmol) of potassium acetate were suspended in 210 ml of toluene in a round-bottomed flask and then, refluxed and stirred for 12 hours. When the reaction was complete, the resultant was cooled down to room temperature and filtered, and the filtered solution was silica gel-filtered and concentrated. The concentrated resultant was recrystallized with acetone to obtain Intermediate E (17 g, 77%).

Synthesis Example 6: Synthesis of Intermediate F

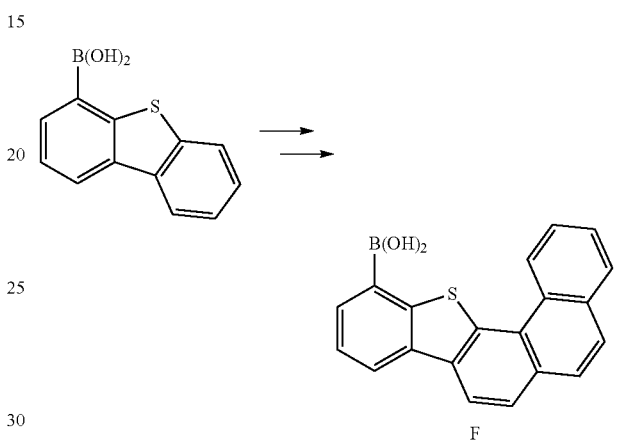

F

Intermediate F (24 g, 41%) was obtained by sequentially applying Synthesis Examples 1 to 3 except for using 40.7 g (178.36 mmol) of 4-dibenzothiopheneboronic acid instead of the 4-dibenzofuranboronic acid in Synthesis Example 1 as a starting material.

Synthesis of Organic Compound

Example 1: Synthesis of Compound Represented by Chemical Formula B-2

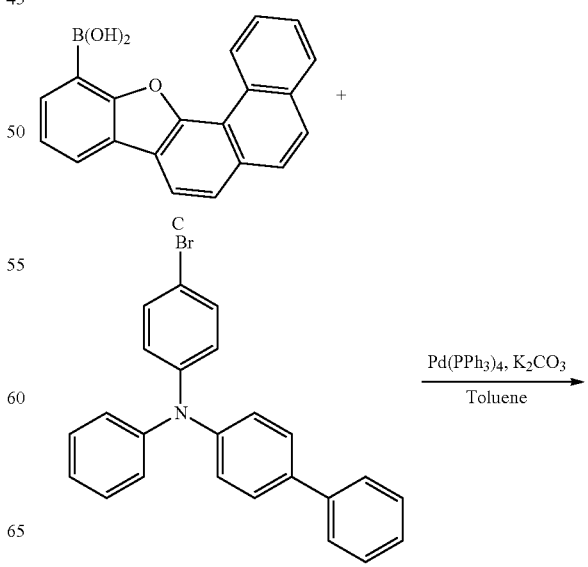

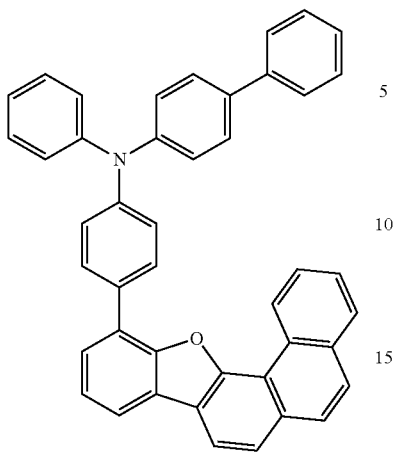

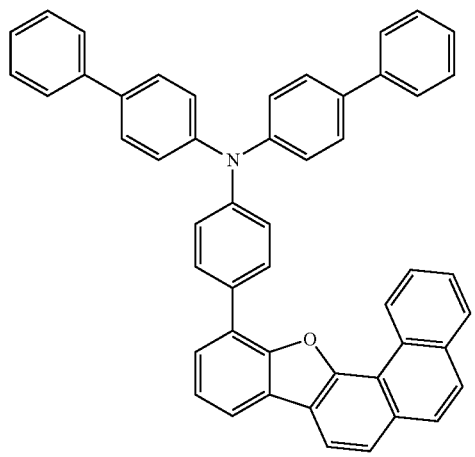

10 g (32.04 mmol) of the Intermediate C according to Synthesis Example 3, 14.11 g (35.24 mmol) of N-(4-bromophenyl)-N-phenylbiphenyl-4-amine, 1.11 g (0.93 mmol) of tetrakis(triphenylphosphine)palladium (0), and 8.86 g of potassium carbonate were suspended in 150 ml of toluene and 70 ml 70 ml of distilled water in a round-bottomed flask and then, refluxed and stirred for 12 hours. When the reaction was complete, the resultant was extracted, silica gel-filtered, and concentrated and then, recrystallized in acetone to obtain Compound B-2 (14.2 g, 75.5%).

LC-Mass (Theoretical value: 587.71 g/mol, Measured value: M+=587 g/mol)

10 g (32.04 mmol) of the Intermediate C according to Synthesis Example 3, 16.79 g (35.24 mmol) of the Intermediate E according to Synthesis Example 5, 1.11 g (0.93 mmol) of tetrakis(triphenylphosphine)palladium (0), and 8.86 g of potassium carbonate were suspended in 150 ml of toluene and 70 ml of distilled water in a round-bottomed flask and then, refluxed and stirred for 12 hours. When the reaction was complete, the resultant was extracted, silica gel-filtered, concentrated, and recrystallized in acetone to obtain Compound B-3 (15.6 g, 73.6%).

LC-Mass (Theoretical value: 663.80 g/mol, Measured value: M+=663 g/mol)

Example 2: Synthesis of Compound Represented by Chemical Formula B-3

Example 3: Synthesis of Compound Represented by Chemical Formula B-75

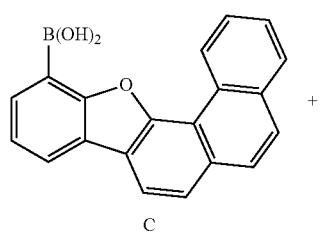

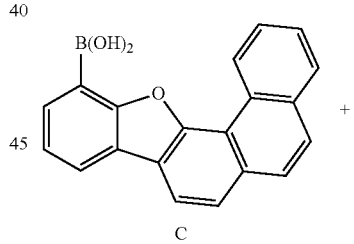

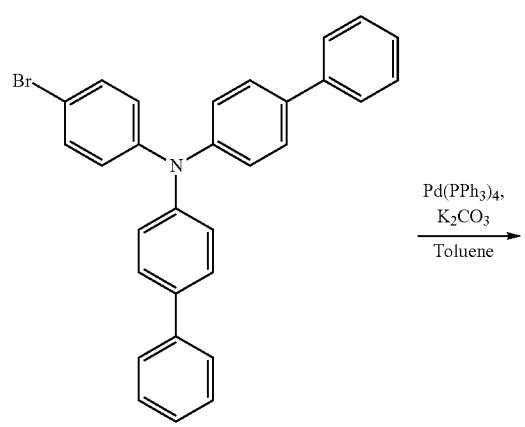

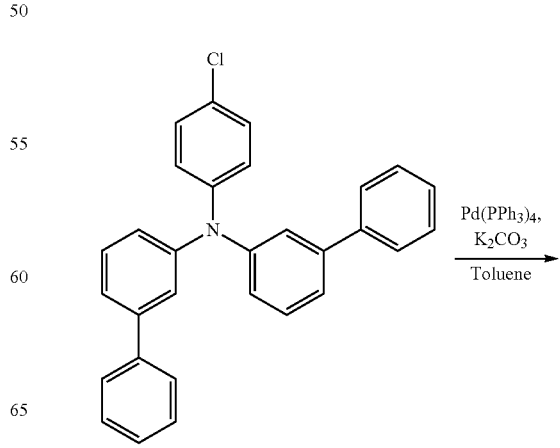

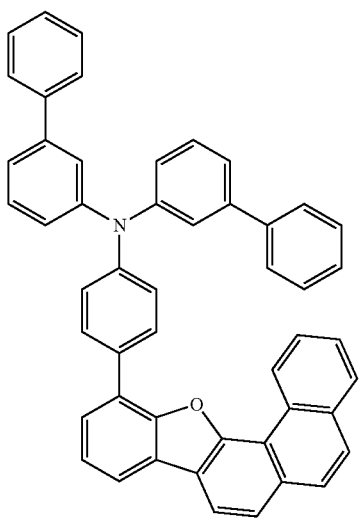

6 g (19.22 mmol) of the Intermediate C according to Synthesis Example 3, 8.30 g (19.22 mmol) of the Intermediate D according to Synthesis Example 4, 0.33 g (0.58 mmol) of Pd(dba)$_2$, 0.27 g (1.35 mmol) of P(t-Bu)3, and 12.53 g (38.45 mmol) of cesium carbonate were suspended in 100 ml of 1,4-dioxane in a round-bottomed flask and then, refluxed and stirred for 12 hours. After completing the reaction, distilled water was added thereto, and the obtained mixture was stirred for 30 minutes. Then, the resultant was extracted with methylene chloride and silica gel-columned to obtain Compound B-75 (6.3 g, 49.4%).

LC-Mass (Theoretical value: 663.80 g/mol, Measured value: M+=663 g/mol)

Example 4: Synthesis of Compound Represented by Chemical Formula B-77

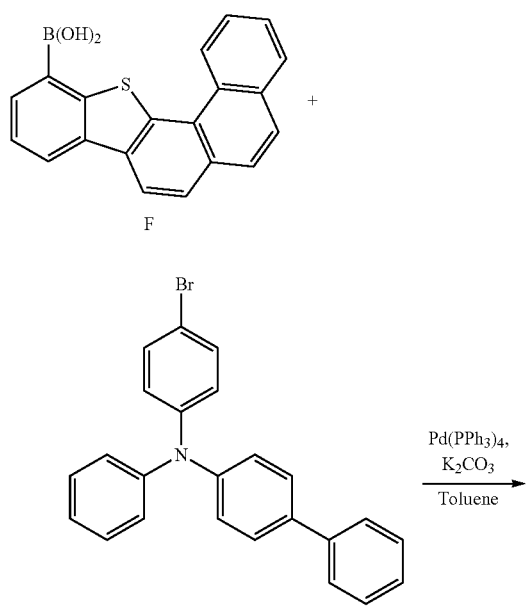

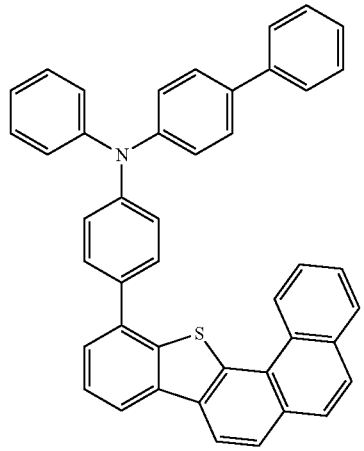

Compound B-77 (12.7 g, 69%) was obtained according to the same method as Example 1 except for using 10 g (30.47 mmol) of the Intermediate F according to Synthesis Example 6 instead of 10 g of the Intermediate C according to Synthesis Example 3 in a round-bottomed flask.

LC-Mass (Theoretical value: 603.77 g/mol, Measured value: M+=603 g/mol)

Manufacture of Organic Light Emitting Diode

Device Example 1

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 5 minutes, and moved to a vacuum depositor. This obtained ITO transparent electrode was used as an anode, a 600 Å-thick hole injection layer was formed on the ITO substrate by vacuum depositing 4,4'-bis[N-[4-{N,N-bis(3-methylphenyl)amino}-phenyl]-N-phenylamino]biphenyl (DNTPD). Subsequently, a 250 Å-thick first hole transport layer was formed by vacuum-depositing the compound represented by Chemical Formula J-9 and a 50 Å-thick second hole transport layer was formed by vacuum-depositing the compound (Chemical Formula B-2) synthesized in Example 1. On the hole transport layer, a 250 Å-thick emission layer was formed by vacuum-depositing 9,10-di-(2-naphthyl)anthracene (ADN) as a host and 2,5,8,11-tetra(tert-butyl)perylene (TBPe) as a dopant in a doping amount of 3 wt %.

Then, Alq3 was vacuum-deposited on the emission layer upper to form a 250 Å-thick electron transport layer. LiF (10 Å) and Al (1000 Å) were sequentially vacuum-deposited on the electron transport layer to form a cathode, manufacturing an organic light emitting diode.

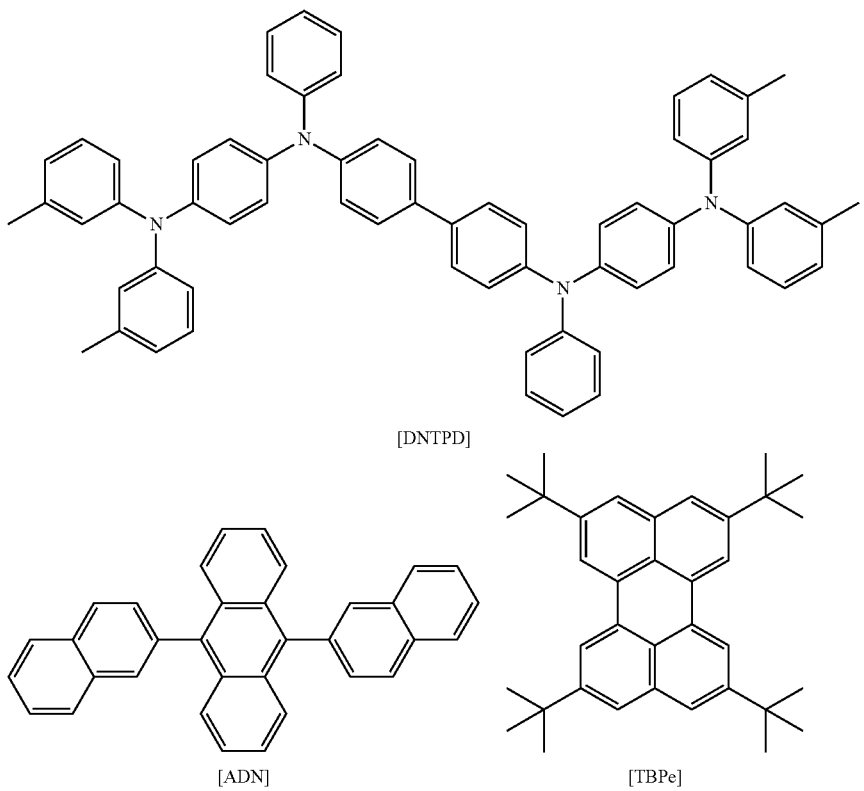

Device Example 2

An organic light emitting diode was manufactured according to the same method as Device Example 1 except for using the compound (Chemical Formula B-3) of Example 2 instead of the compound (Chemical Formula B-2) of Example 1 to form the second hole transport layer (HTL).

Device Example 3

An organic light emitting diode was manufactured according to the same method as Device Example 1 except for using the compound (Chemical Formula B-76) of Example 3 instead of the compound (Chemical Formula B-2) of Example 1 to form the second hole transport layer (HTL).

Device Example 4

An organic light emitting diode was manufactured according to the same method as Device Example 1 except for using the compound (Chemical Formula B-78) of Example 4 instead of the compound (Chemical Formula B-2) of Example 1 to form the second hole transport layer (HTL).

An organic light emitting diode was manufactured according to the same method as Device Example 1 except for forming the first hole transport layer (HTL) to be 300 Å thick without forming the second hole transport layer (HTL).

Evaluation

Current density change depending on a voltage, luminance change, and luminous efficiency of each organic light emitting diode according to Device Example 1 to Device Example 4 and Device Comparative Example 1 were measured.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Current Efficiency

Current efficiency (cd/A) at the same current density (10 mA/cm$^2$) were calculated by using the luminance, current density, and voltages (V) from the items (1) and (2).

The HOMO energy level is obtained by structurally being optimized in a B3LYP/6-31G (d, p) level using a DFT method of a Gaussian program.

TABLE 1

| Devices | Compound used in second hole transport layer | Driving voltage (V) | Color (EL color) | Efficiency (cd/A) | Half-life life-span (h) at 1000 cd/m$^2$ |
|---|---|---|---|---|---|
| Device Example 1 | B-2 | 5.9 | Blue | 6.3 | 2,000 |
| Device Example 2 | B-3 | 6.0 | Blue | 6.6 | 1,910 |

TABLE 1-continued

| Devices | Compound used in second hole transport layer | Driving voltage (V) | Color (EL color) | Efficiency (cd/A) | Half-life life-span (h) at 1000 cd/m² |
|---|---|---|---|---|---|
| Device Example 3 | B-76 | 6.0 | Blue | 6.9 | 1,940 |
| Device Example 4 | B-78 | 5.9 | Blue | 6.8 | 1,870 |
| Device Comparative Example 1 | NA | 6.4 | Blue | 5.9 | 1,380 |

Current density: 10 mA/cm²

Referring to Table 1, the organic light emitting diodes according to Device Example 1 to Device Example 4 showed a lower driving voltage, and improved efficiency and life-span characteristics compared with the organic light emitting diode according to Device Comparative Example 1.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200, 300: organic light emitting diode
105: organic layer
110: cathode
120: anode
130: emission layer
140: hole transport layer
141: first hole transport layer
142: second hole transport layer

What is claimed is:

1. An organic optoelectric device, comprising:
an anode and a cathode facing each other, and
at least one organic layer between the anode and the cathode, wherein:
the at least one organic layer includes:
an emission layer, and
a hole transport layer between the anode and the emission layer, the hole transport layer includes:
a first hole transport layer adjacent to the anode, and
a second hole transport layer adjacent to the emission layer, the second hole transport layer includes an organic compound represented by Chemical Formula 1:

[Chemical Formula 1]

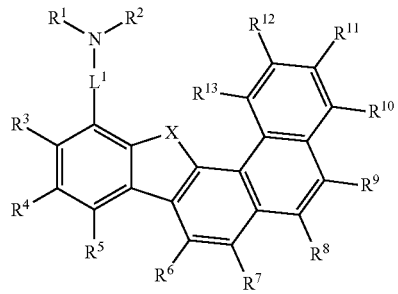

wherein, in Chemical Formula 1,

X is O or S, $L^1$ is a single bond, a substituted or unsubstituted C6 to C30 arylene group, or a substituted or unsubstituted C2 to C30 heterocyclic group, $R^1$ and $R^2$ are independently a substituted or unsubstituted C1 to C20 alkyl group, a substituted or unsubstituted C6 to C30 aryl group, a substituted or unsubstituted C6 to C30 heterocyclic group, a substituted or unsubstituted C3 to C40 silyl group, or a combination thereof, wherein,

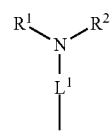

is not

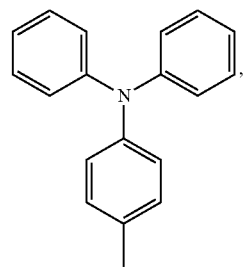 [SMILES: Cc1ccc(N(c2ccccc2)c2ccccc2)cc1]

and $R^3$ to $R^{13}$ are independently hydrogen, deuterium, a halogen, a cyano group, a hydroxyl group, an amino group, a substituted or unsubstituted C1 to C20 amine group, a nitro group, a substituted or unsubstituted C1 to C20 alkyl group, a substituted or unsubstituted C6 to C30 aryl group, a substituted or unsubstituted C1 to C20 alkoxy group, a substituted or unsubstituted C6 to C20 aryloxy group, a substituted or unsubstituted C2 to C30 heterocyclic group, a substituted or unsubstituted C3 to C40 silyl group, or a combination thereof.

2. The organic optoelectric device of claim 1, wherein the organic compound represented by Chemical Formula 1 is represented by one selected from Chemical Formula 2-1 to Chemical Formula 2-4:

[Chemical Formula 2-1]

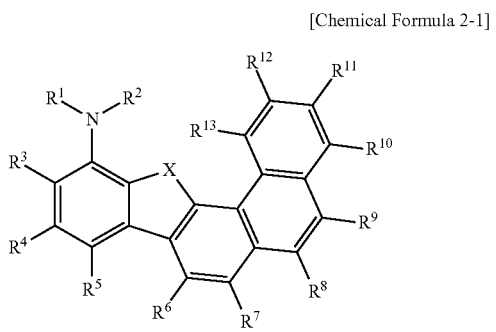

[Chemical Formula 2-2]

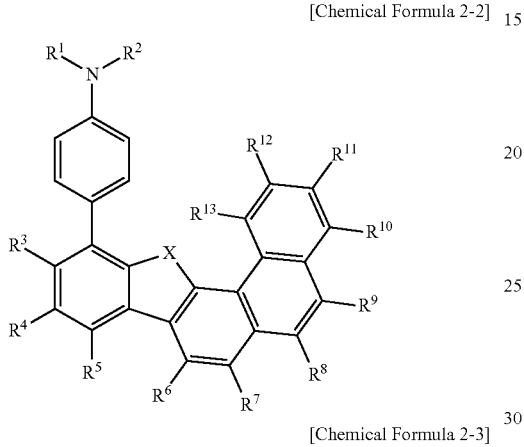

[Chemical Formula 2-3]

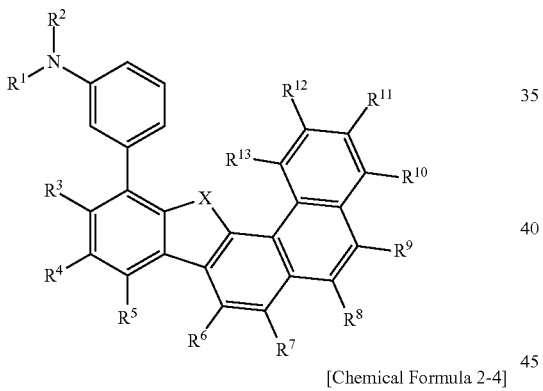

[Chemical Formula 2-4]

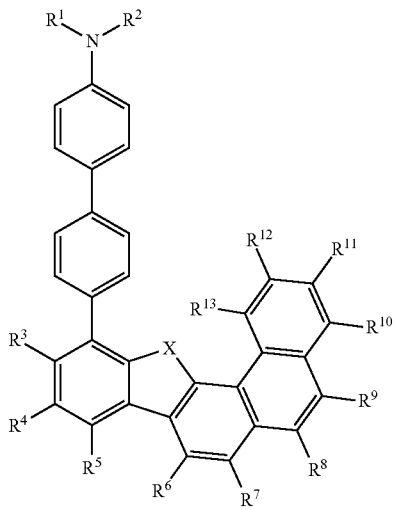

wherein, in Chemical Formula 2-1 to Chemical Formula 2-4,

X is O or S, $R^1$ and $R^2$ are independently a substituted or unsubstituted C1 to C20 alkyl group, a substituted or unsubstituted C6 to C30 aryl group, a substituted or unsubstituted C6 to C30 heterocyclic group, a substituted or unsubstituted C3 to C40 silyl group, or a combination thereof, wherein, in Chemical Formula 2-2,

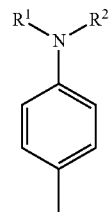

is not

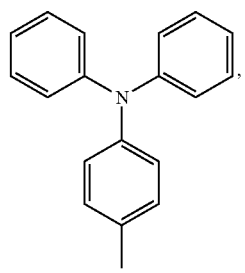 [SMILES: Cc1ccc(N(c2ccccc2)c2ccccc2)cc1]

and $R^3$ to $R^{13}$ are independently hydrogen, deuterium, a halogen, a cyano group, a hydroxyl group, an amino group, a substituted or unsubstituted C1 to C20 amine group, a nitro group, a substituted or unsubstituted C1 to C20 alkyl group, a substituted or unsubstituted C6 to C30 aryl group, a substituted or unsubstituted C1 to C20 alkoxy group, a substituted or unsubstituted C6 to C20 aryloxy group, a substituted or unsubstituted C2 to C30 heterocyclic group, a substituted or unsubstituted C3 to C40 silyl group, or a combination thereof.

3. The organic optoelectric device of claim 1, wherein the $R^1$ and $R^2$ are independently a substituted or unsubstituted C6 to C30 aryl group or a substituted or unsubstituted C6 to C12 heterocyclic group.

4. The organic optoelectric device of claim 1, wherein the $R^3$ to $R^{13}$ are independently hydrogen, deuterium, or a substituted or unsubstituted C6 to C30 aryl group.

5. The organic optoelectric device of claim 3, wherein the $R^1$ and $R^2$ are independently a substituted or unsubstituted phenyl group, a substituted or unsubstituted biphenyl group, a substituted or unsubstituted triphenylene group, a substituted or unsubstituted terphenyl group, a substituted or unsubstituted fluorene group, a substituted or unsubstituted bisfluorene group, a substituted or unsubstituted naphthyl group, a substituted or unsubstituted isochrysene group, a substituted or unsubstituted anthracene group, a substituted or unsubstituted dibenzofuran group, or a substituted or unsubstituted dibenzothiophenyl group.

6. The organic optoelectric device of claim 3, wherein the $R^1$ and $R^2$ are independently one of groups of Group 1:

[Group 1]
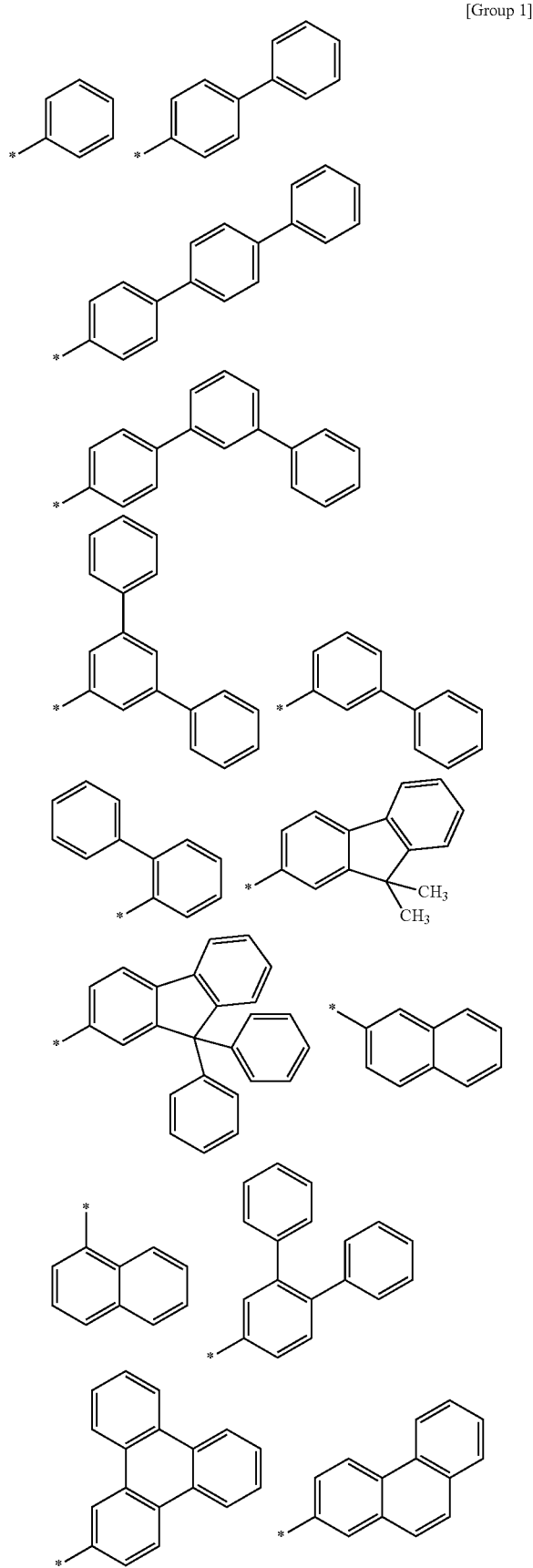
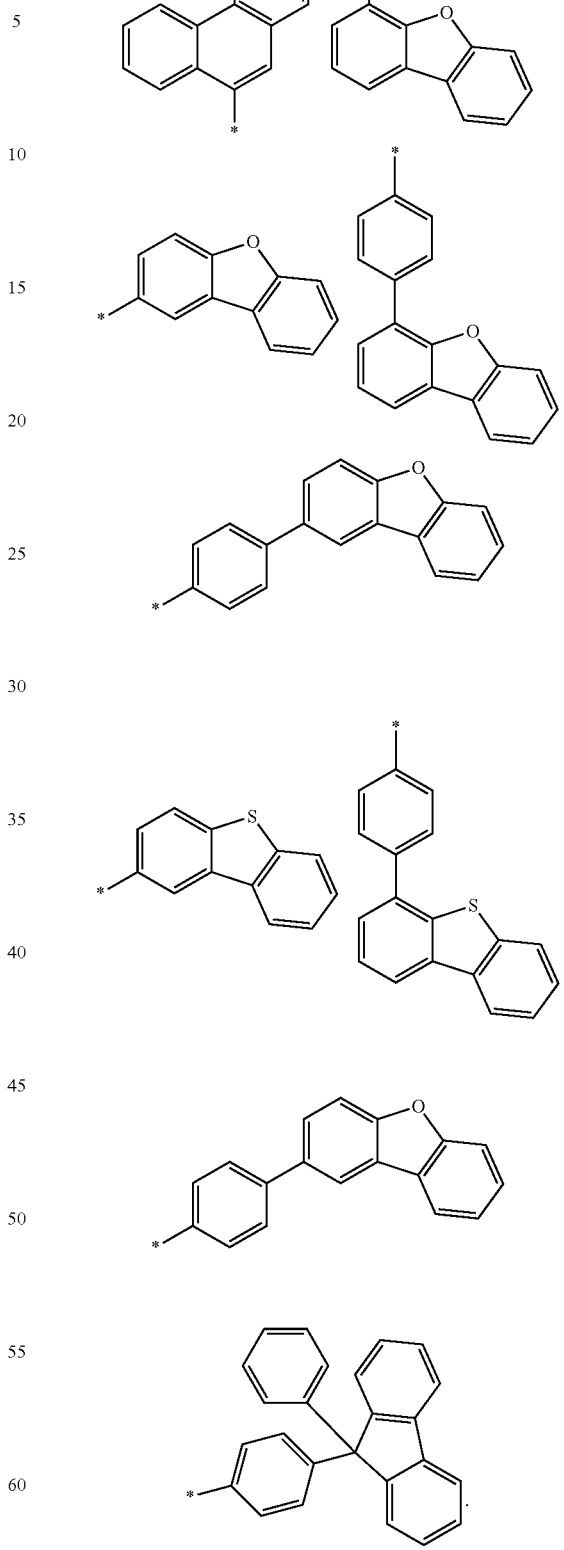
7. The organic optoelectric device of claim 1, wherein the organic compound represented by Chemical Formula 1 is one of the following compounds:

[CF A-1]
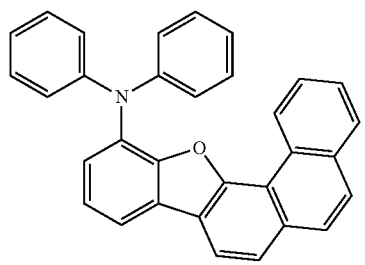
[CF A-2]
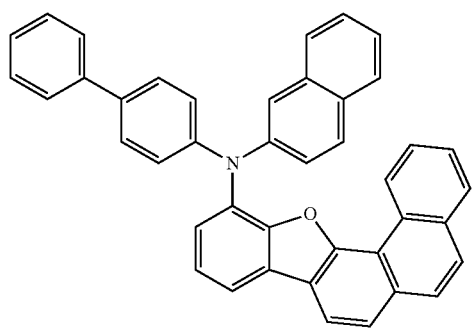
[CF A-3]
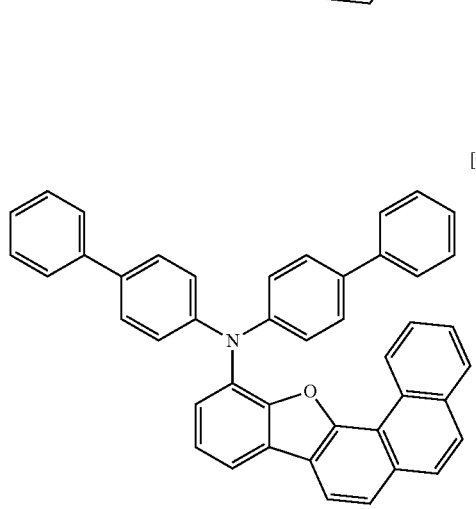
[CF A-4]
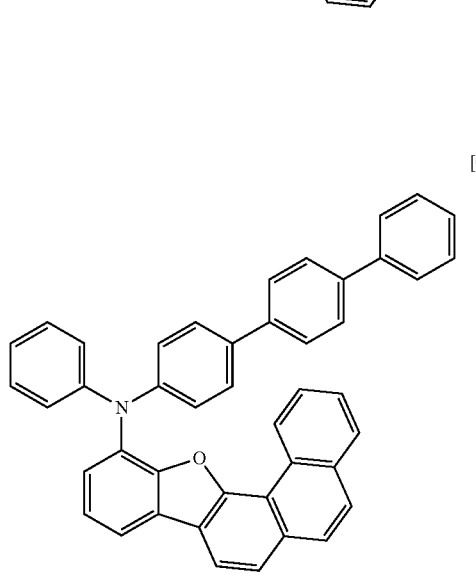
[CF A-5]
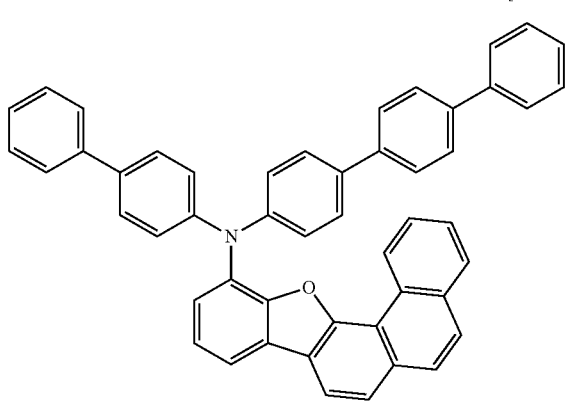
[CF A-6]
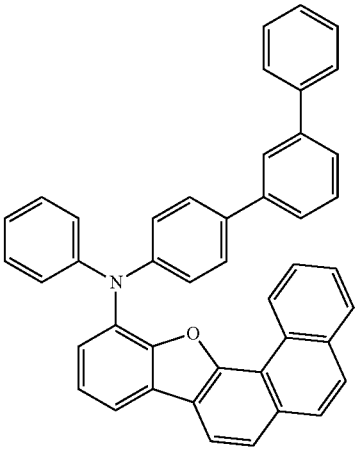
[CF A-7]
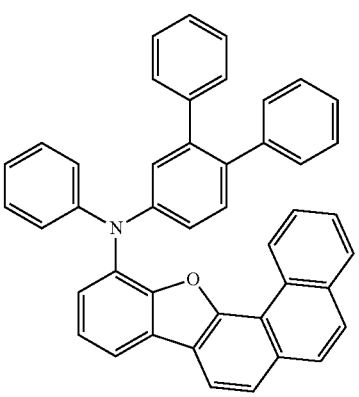

[CF A-8]
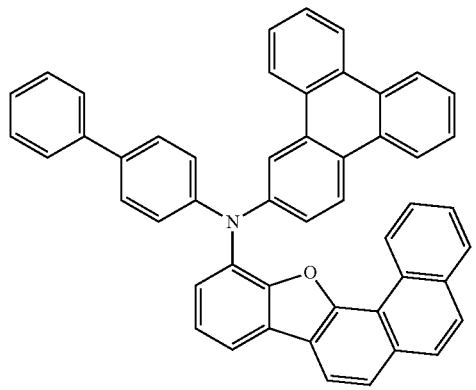
[CF A-9]
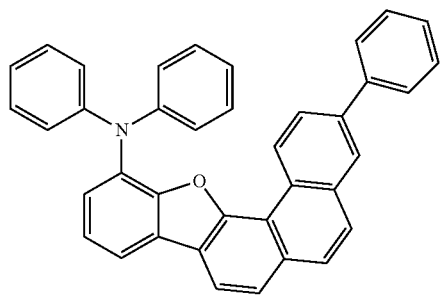
[CF B-2]
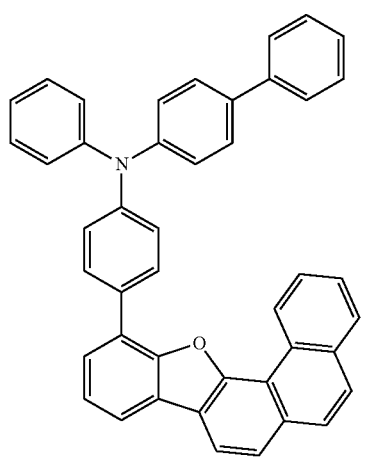
[CF B-3]
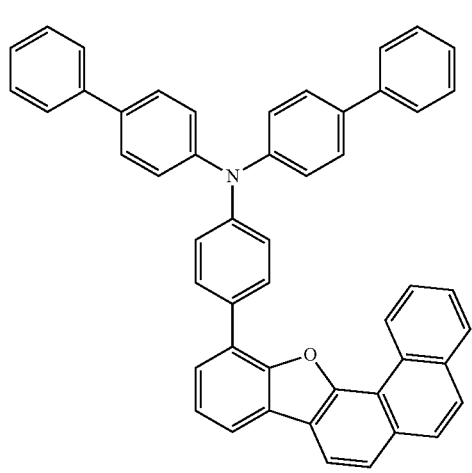
[CF B-4]
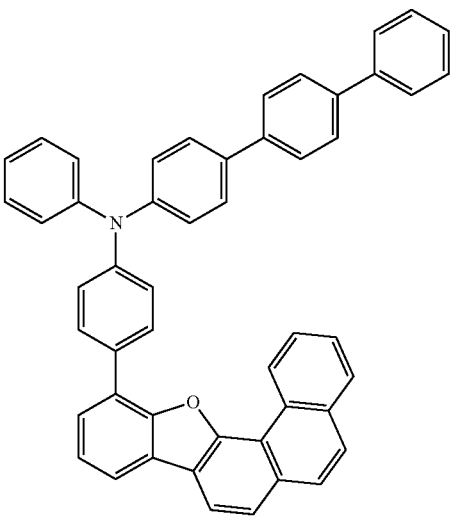
[CF B-5]
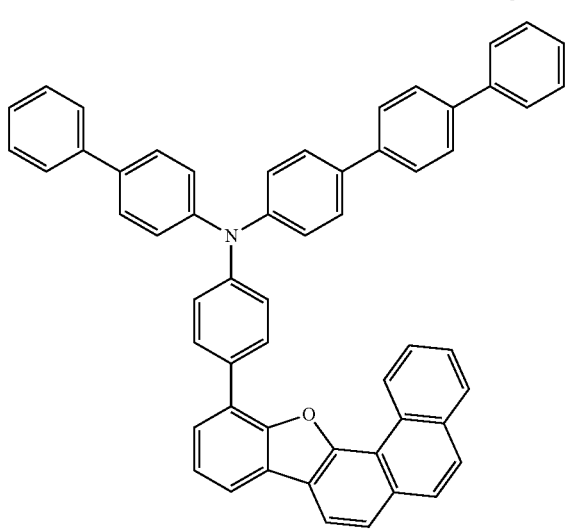
[CF B-6]
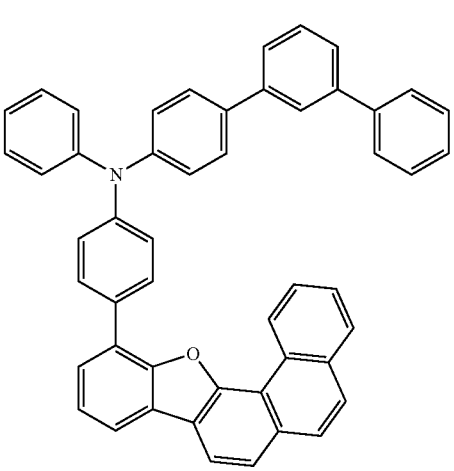

[CF B-7]
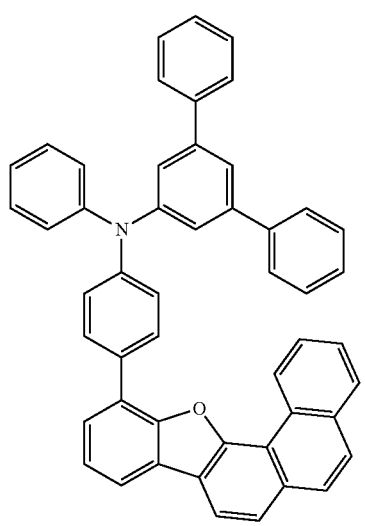
[CF B-10]
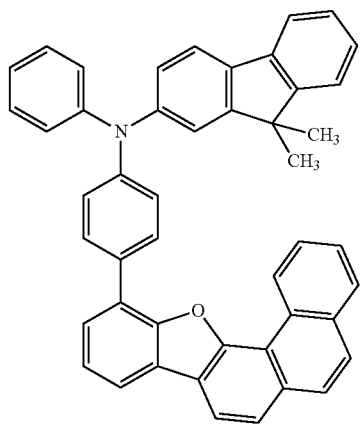
[CF B-8]
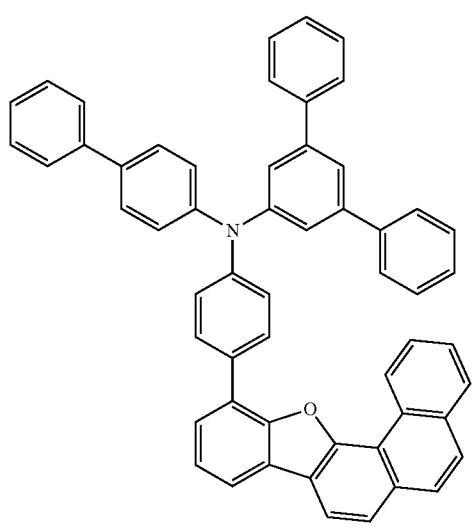
[CF B-11]
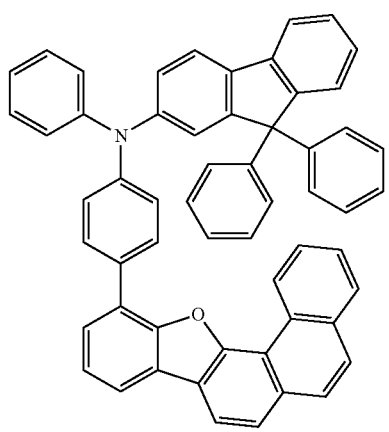
[CF B-9]
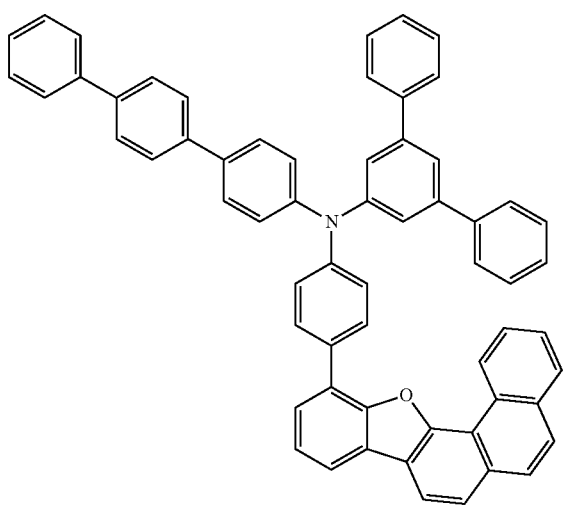
[CF B-12]
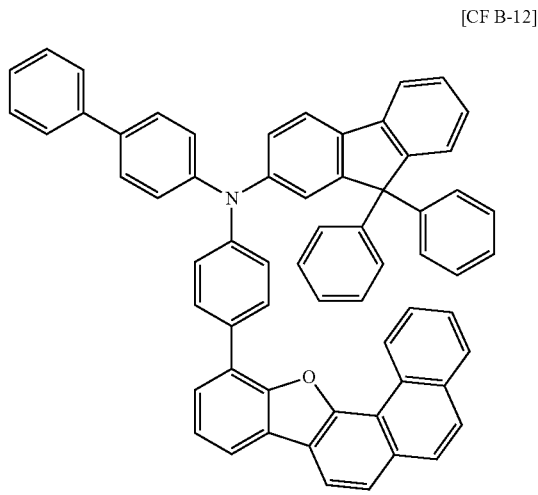

[CF B-13]
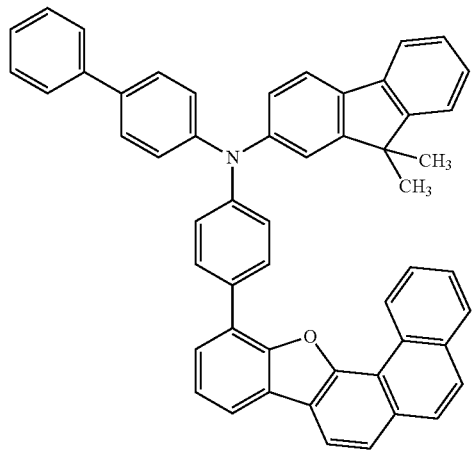
[CF B-16]
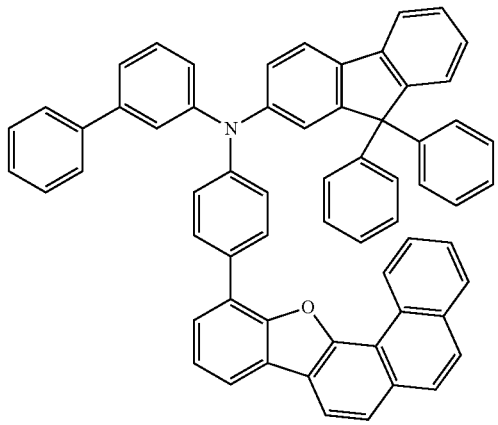
[CF B-14]
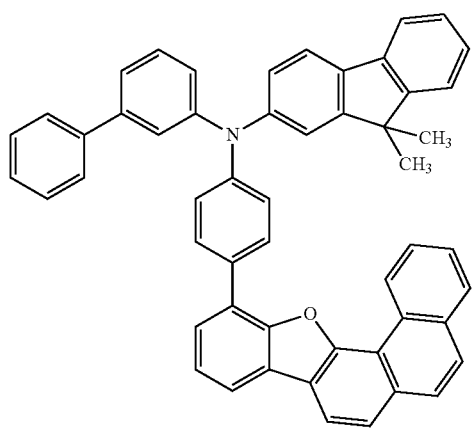
[CF B-17]
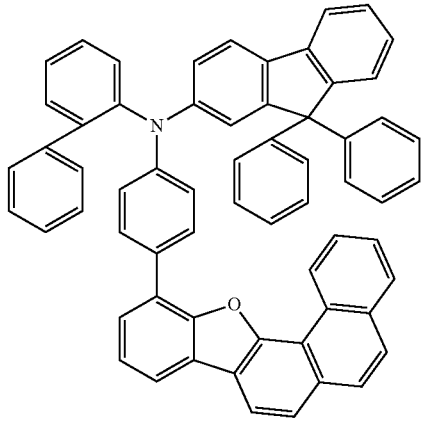
[CF B-15]
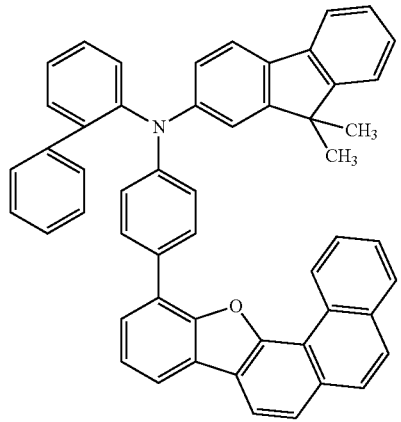
[CF B-18]
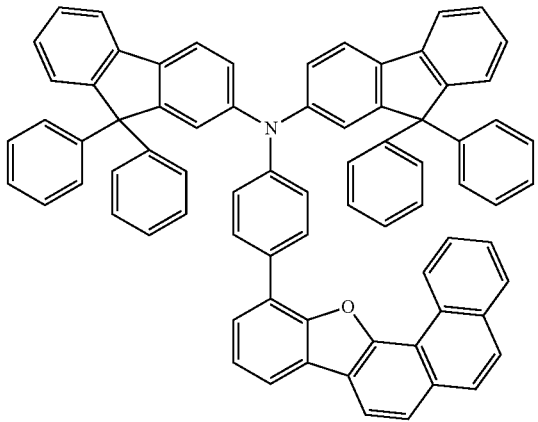

[CF B-20]
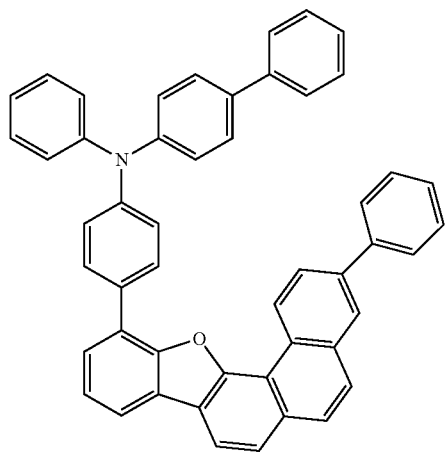
[CF B-23]
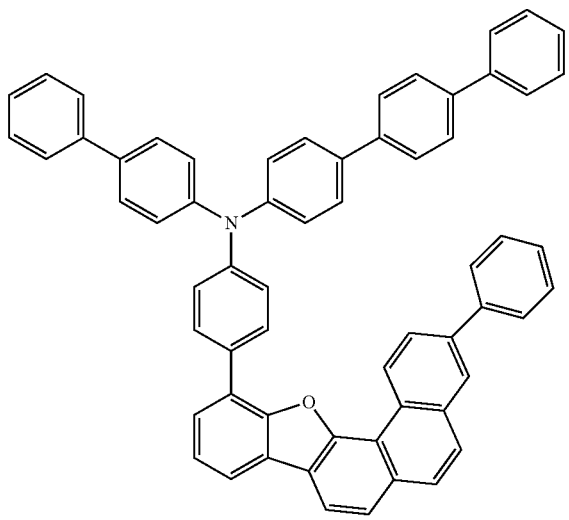
[CF B-21]
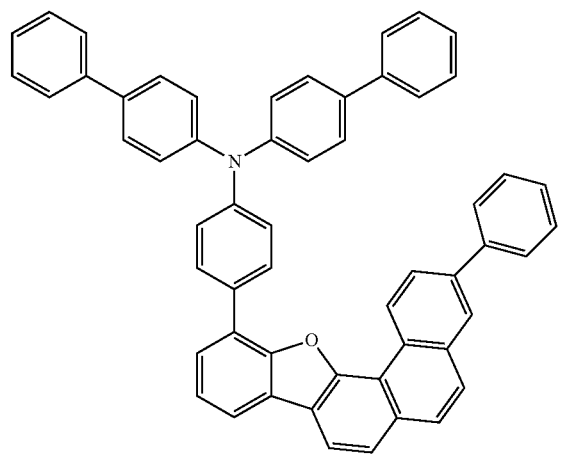
[CF B-24]
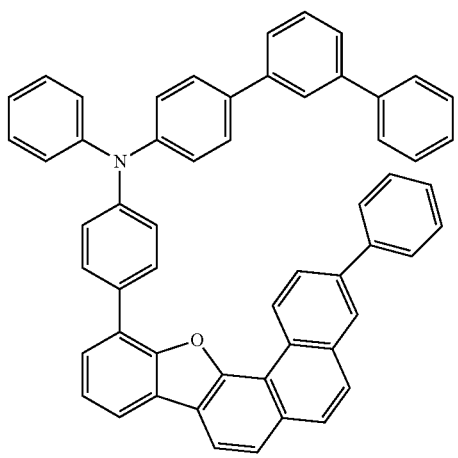
[CF B-22]
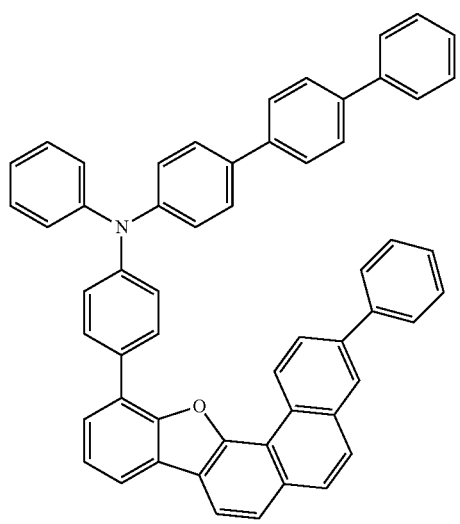
[CF B-25]
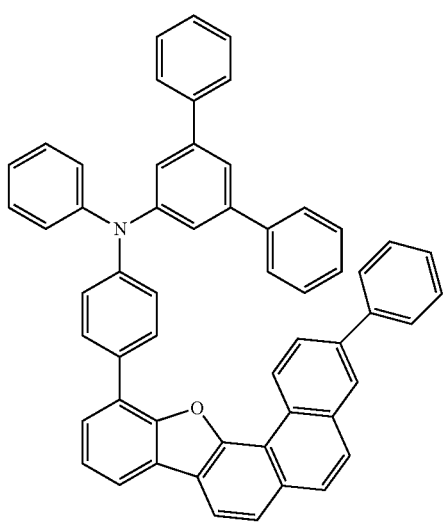

[CF B-26]
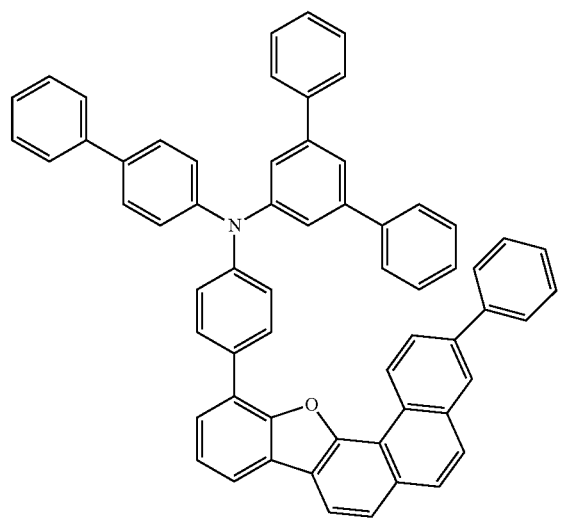
[CF B-29]
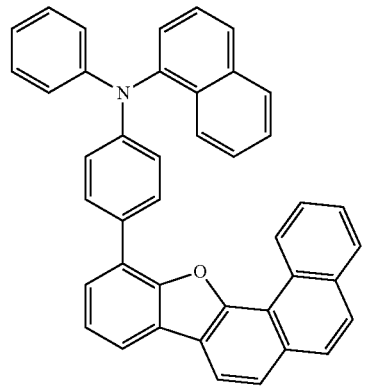
[CF B-27]
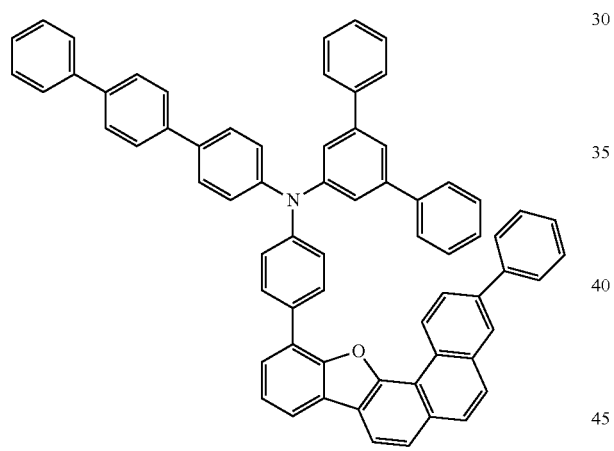
[CF B-30]
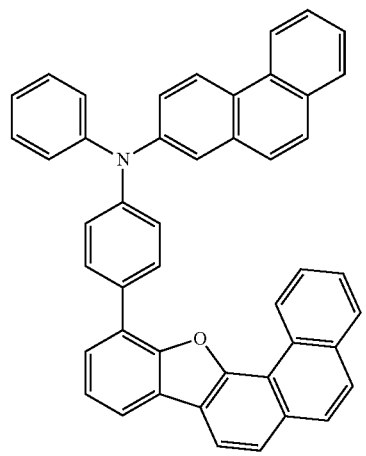
[CF B-28]
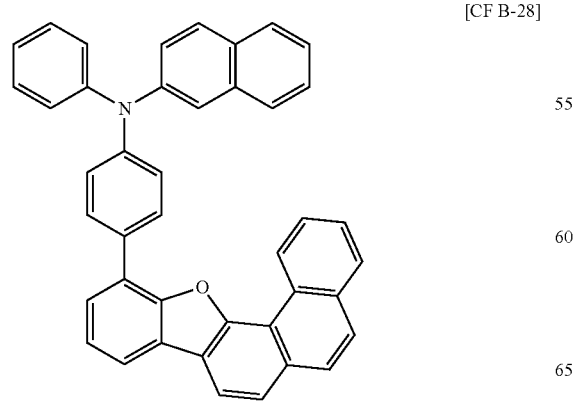
[CF B-31]
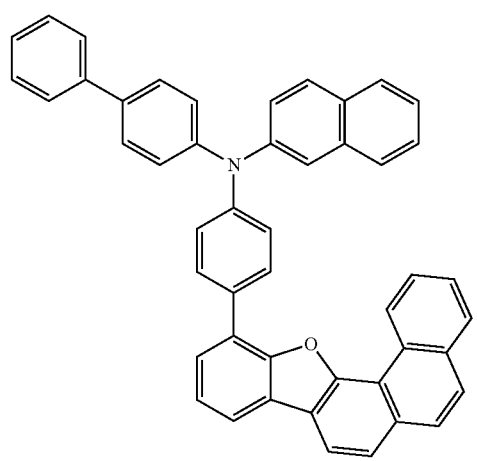

[CF B-32]
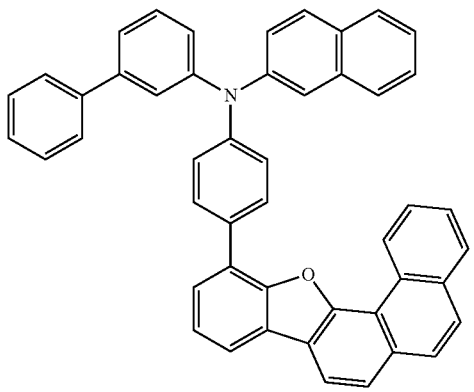
[CF B-35]
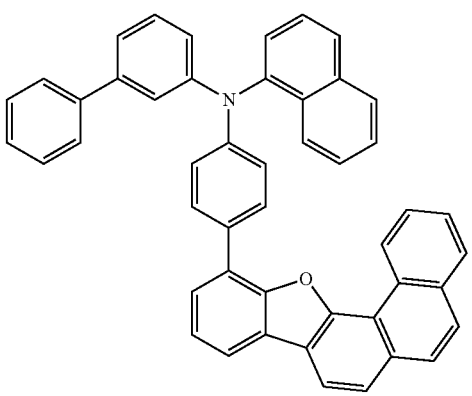
[CF B-33]
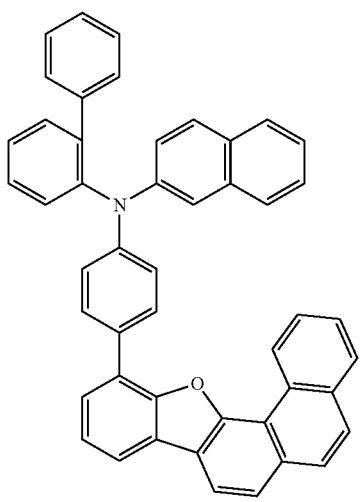
[CF B-36]
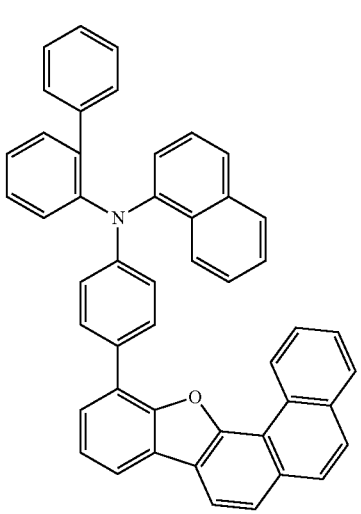
[CF B-34]
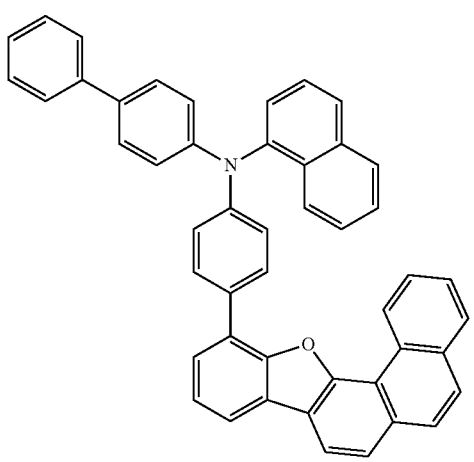
[CF B-37]
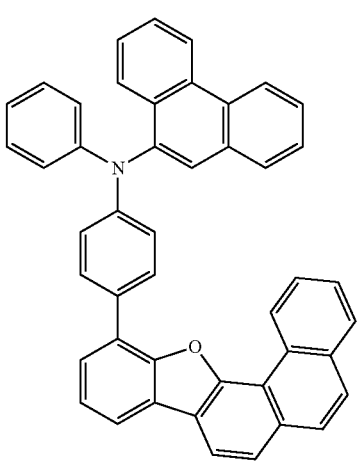

[CF B-38]
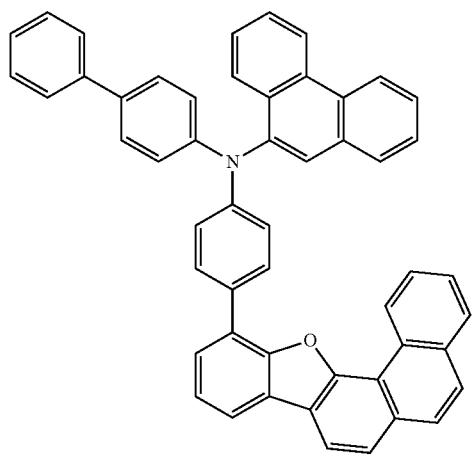
[CF B-41]
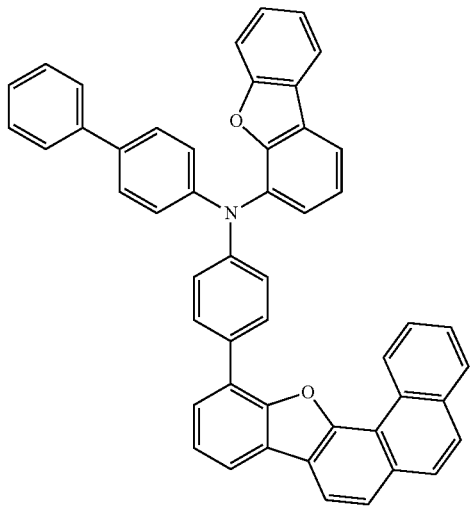
[CF B-39]
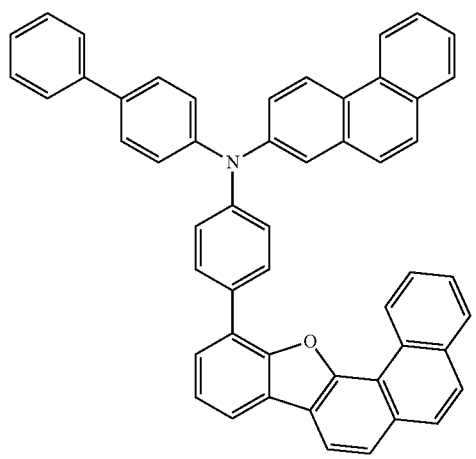
[CF B-42]
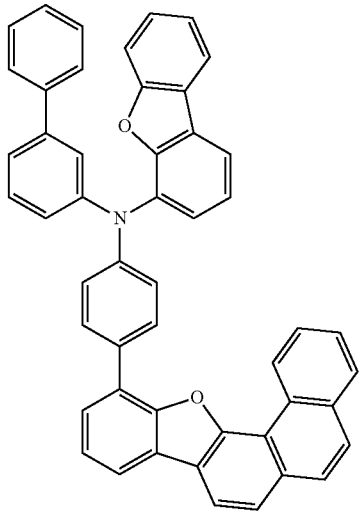
[CF B-40]
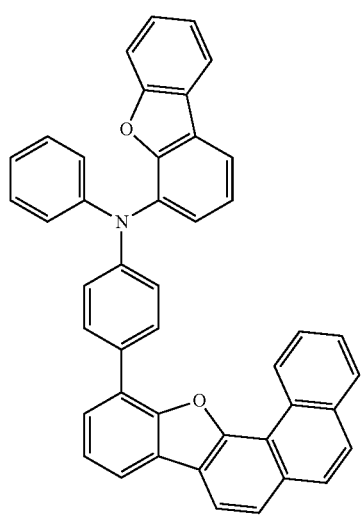
[CF B-43]
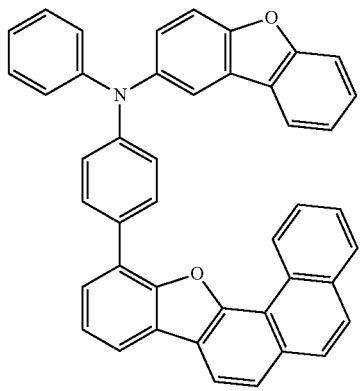

[CF B-44]
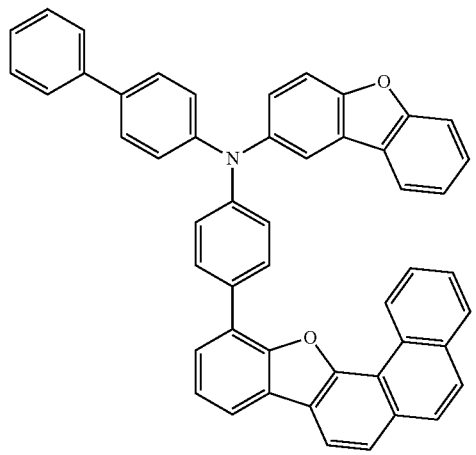
[CF B-47]
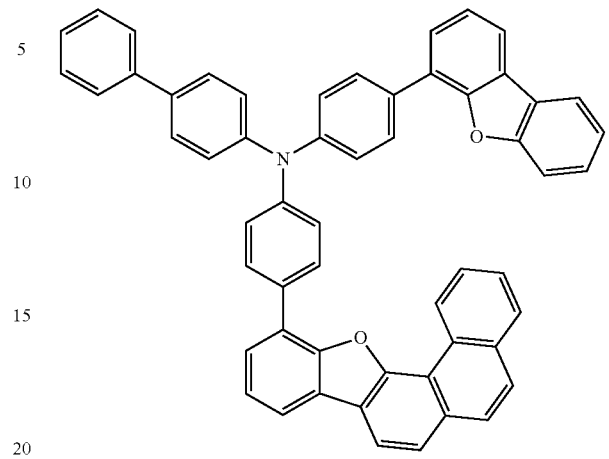
[CF B-45]
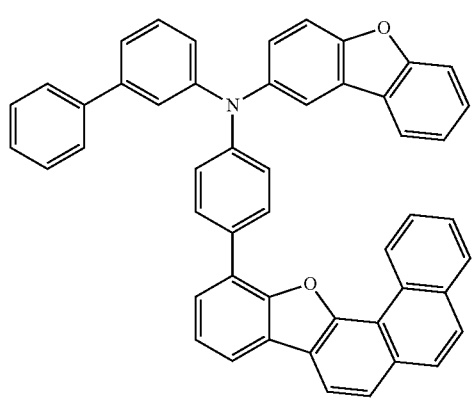
[CF B-48]
[CF B-46]
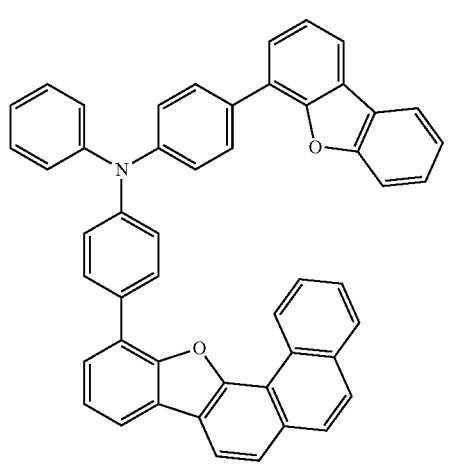
[CF B-49]
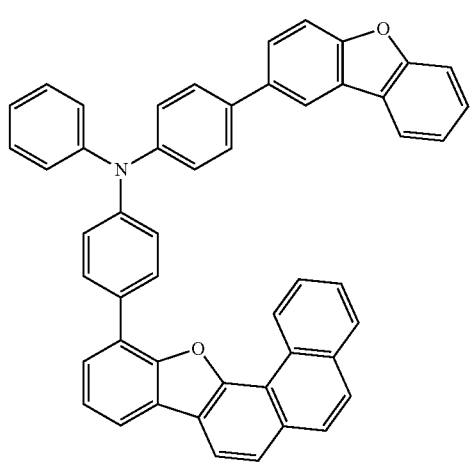

[CF B-50]
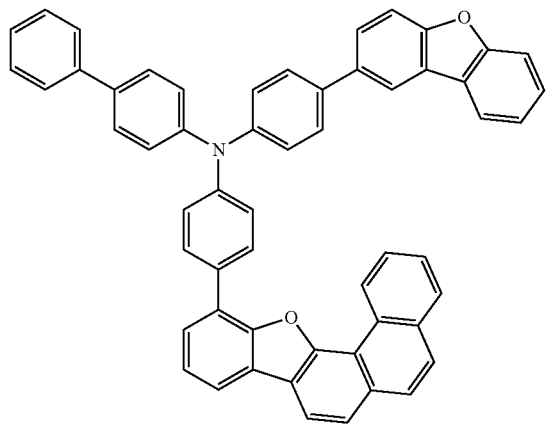
[CF B-51]
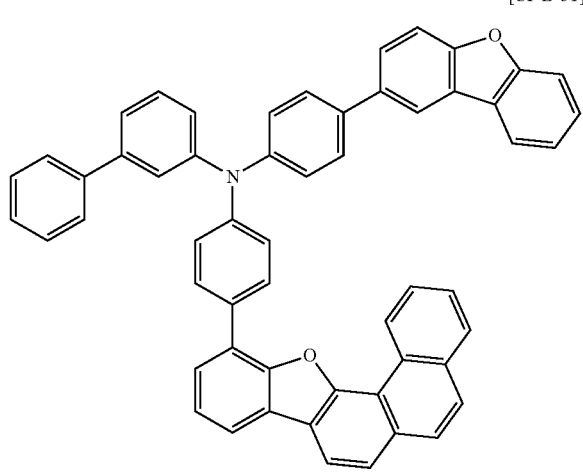
[CF B-52]
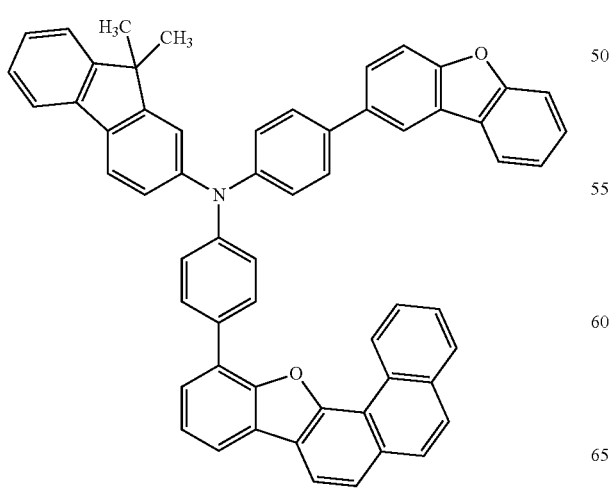
[CF B-53]
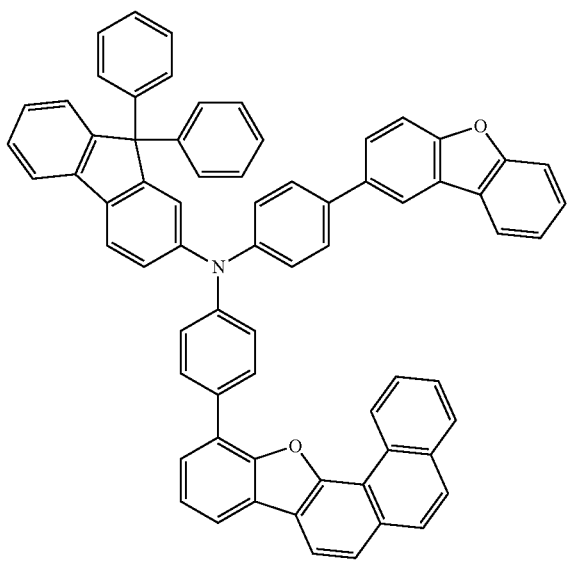
[CF B-54]
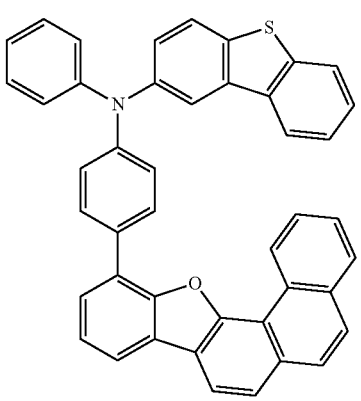
[CF B-55]
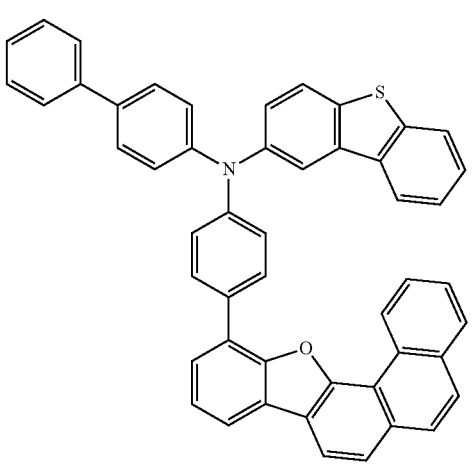

[CF B-56]
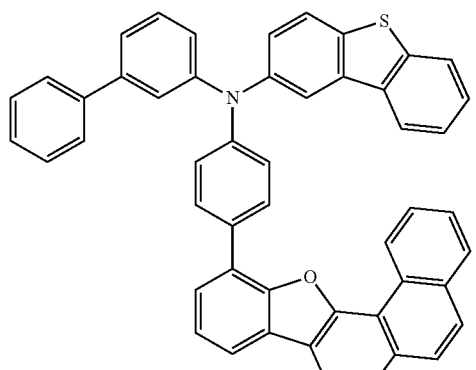
[CF B-57]
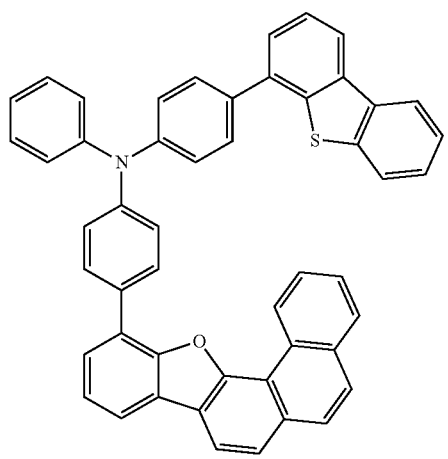
[CF B-58]
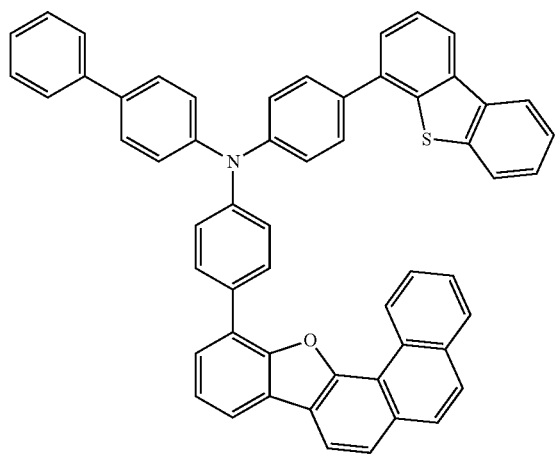
[CF B-59]
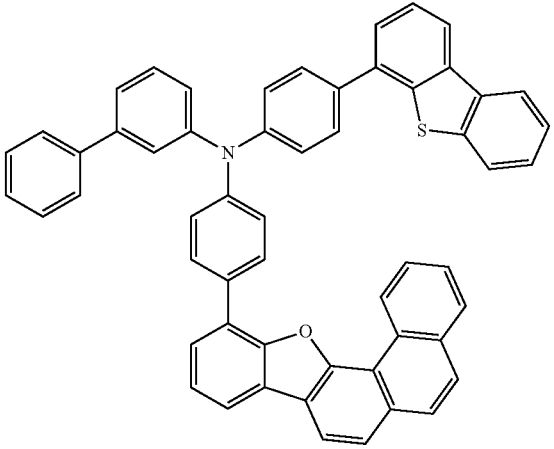
[CF B-60]
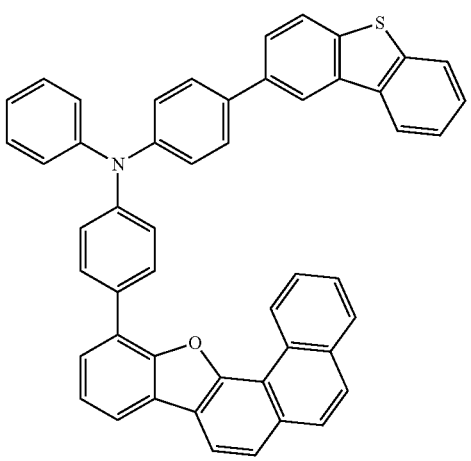
[CF B-61]
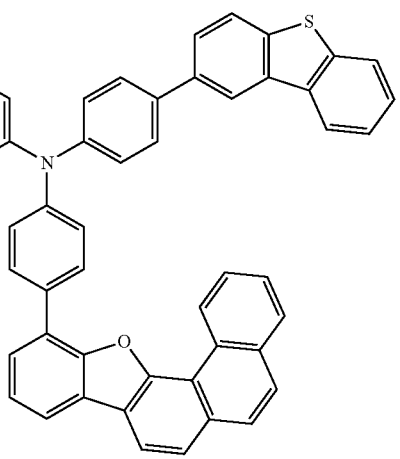

[CF B-62]
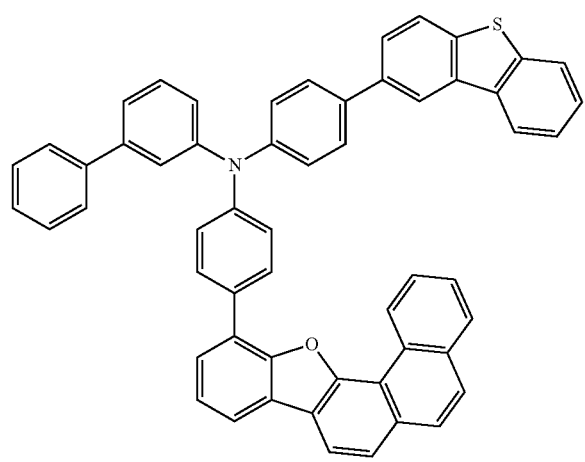
[CF B-63]
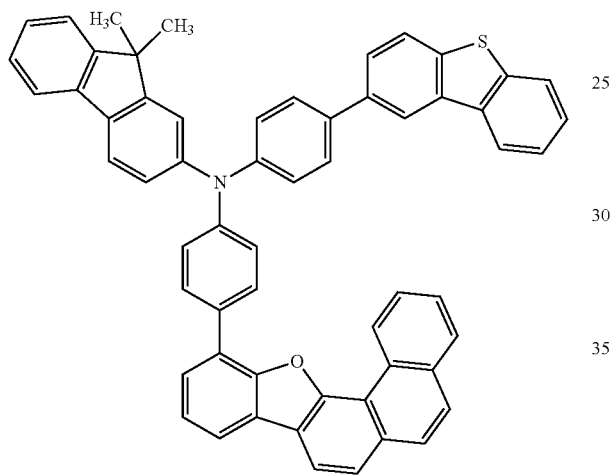
[CF B-64]
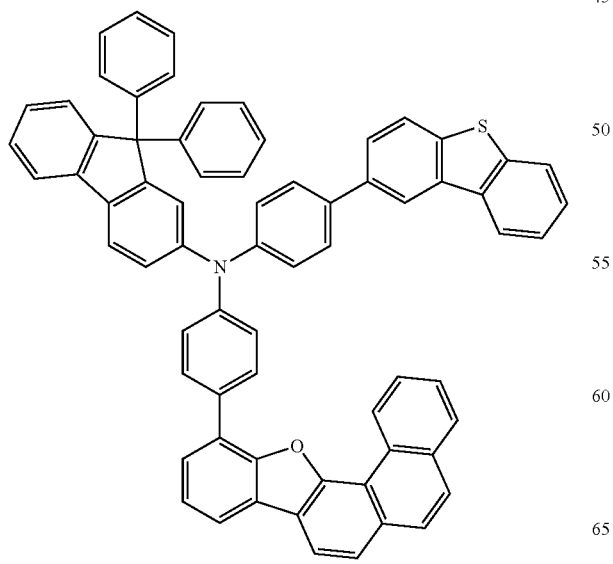
[CF B-65]
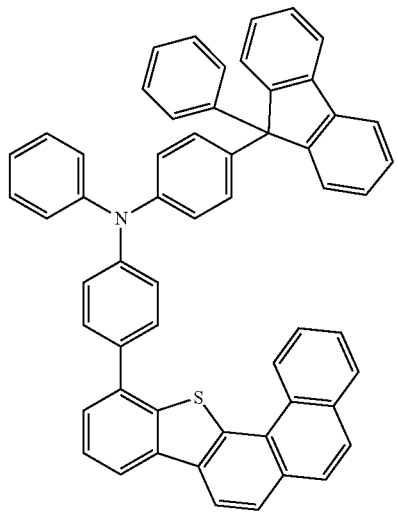
[CF B-66]
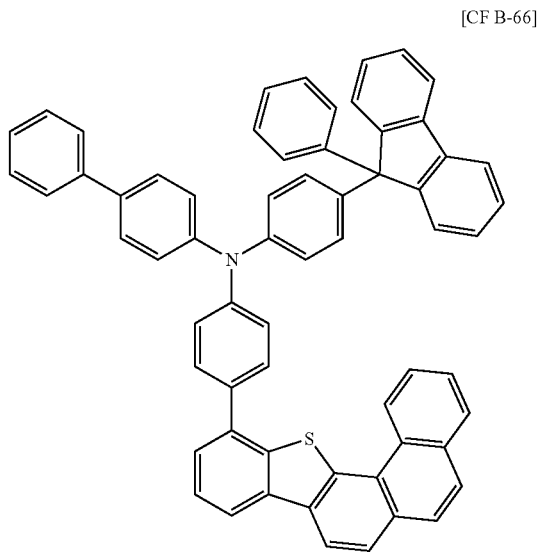
[CF B-67]
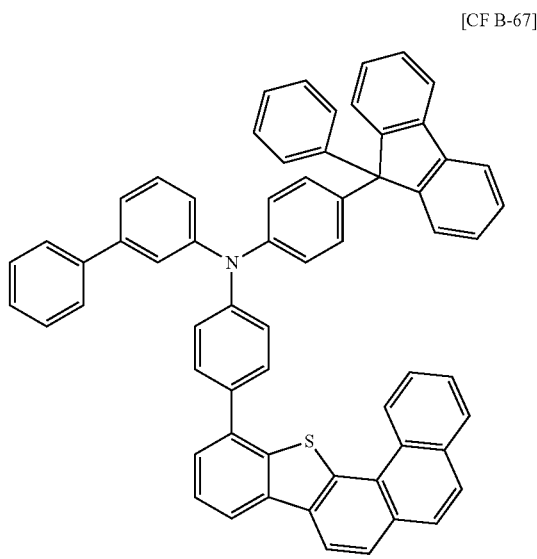

[CF B-68]
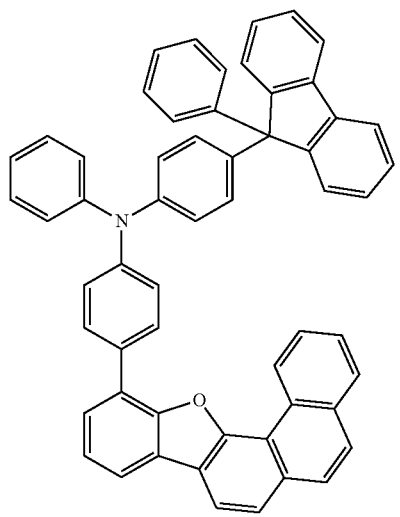
[CF B-69]
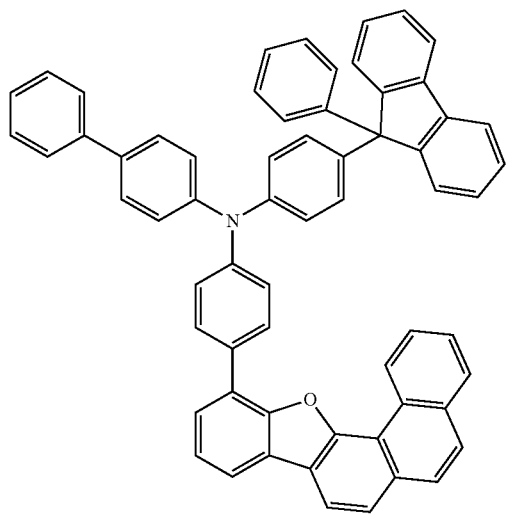
[CF B-70]
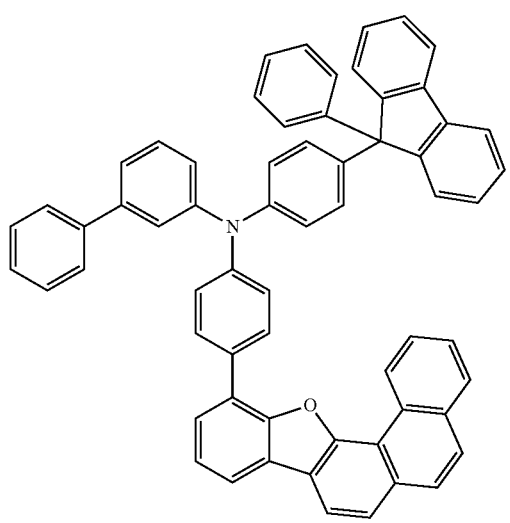
[CF B-71]
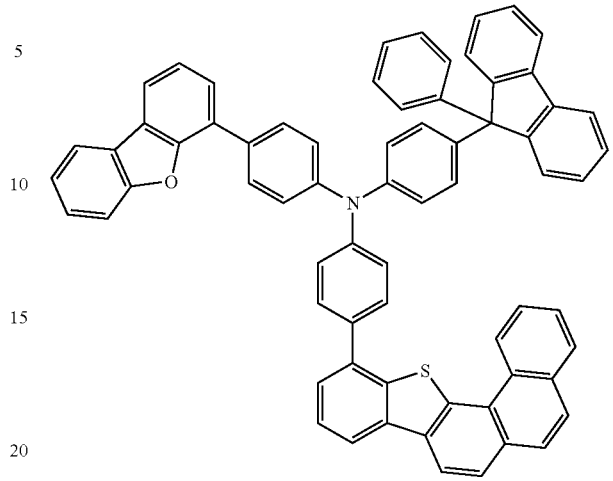
[CF B-72]
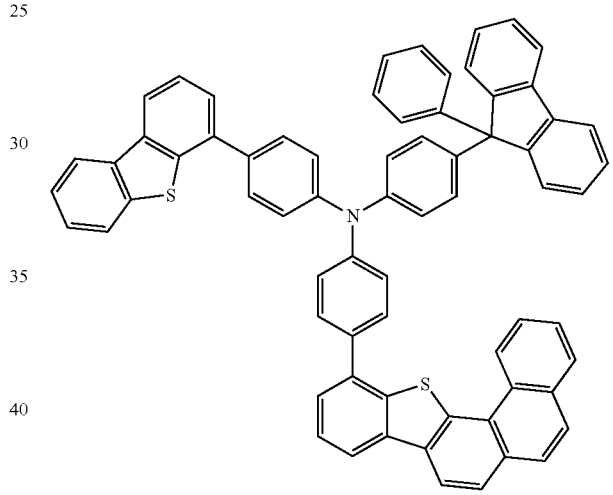
[CF B-73]
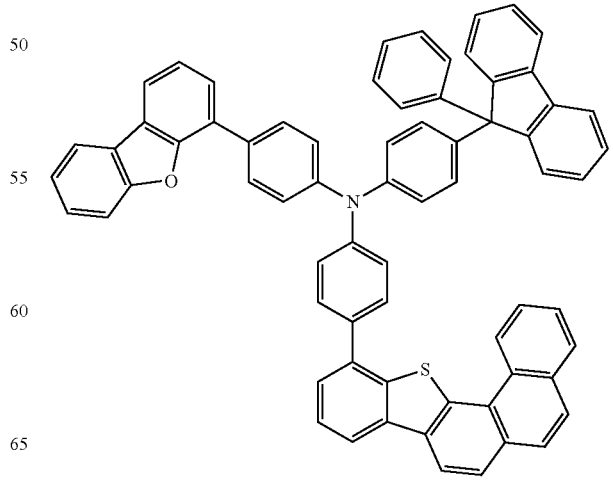

[CF B-74]
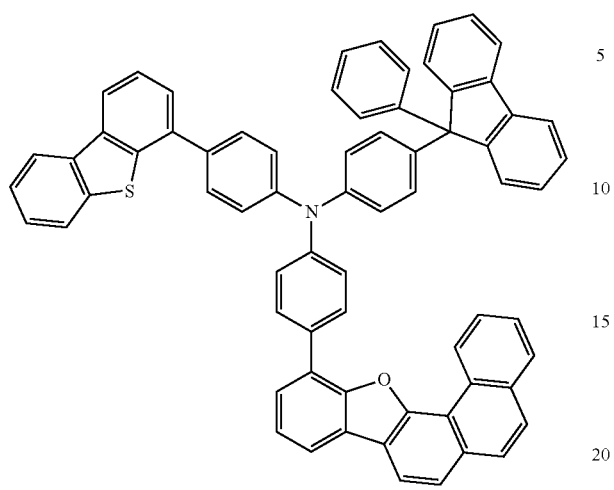
[CF B-78]
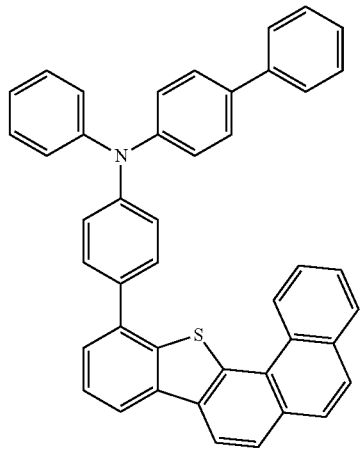
[CF B-75]
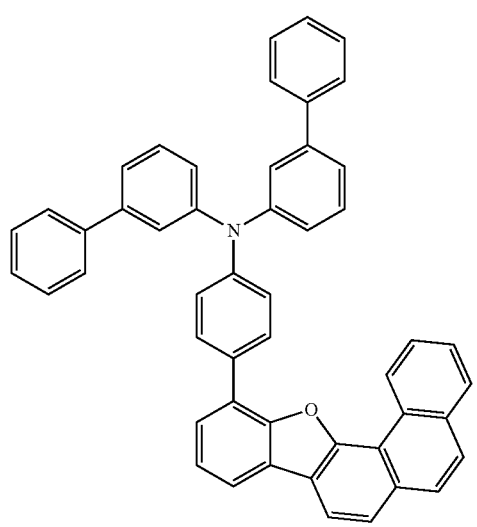
[CF B-79]
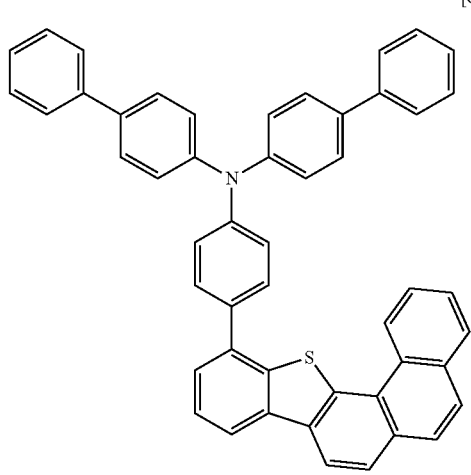
[CF B-77]
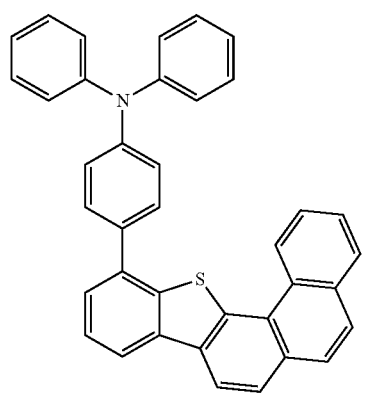
[CF B-80]
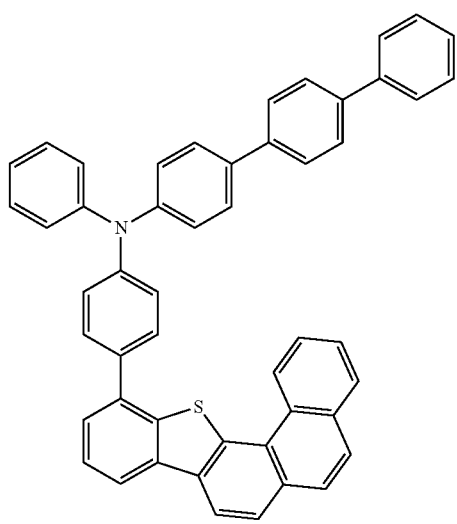

[CF B-81]
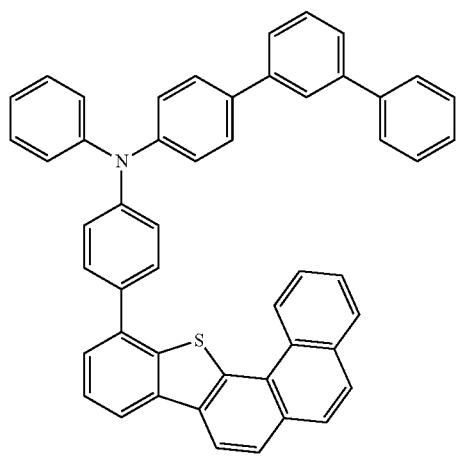
[CF B-82]
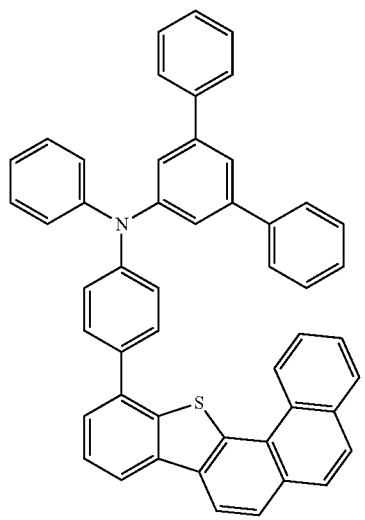
[CF B-83]
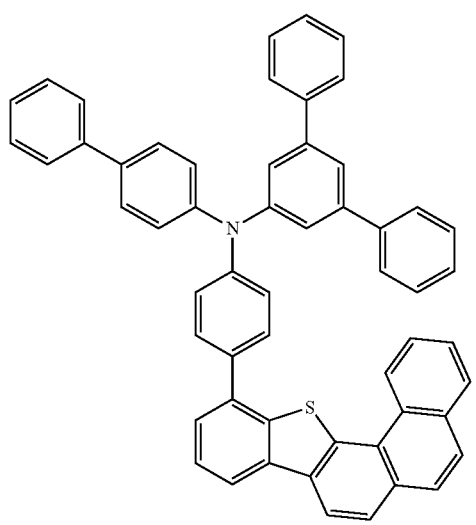
[CF B-84]
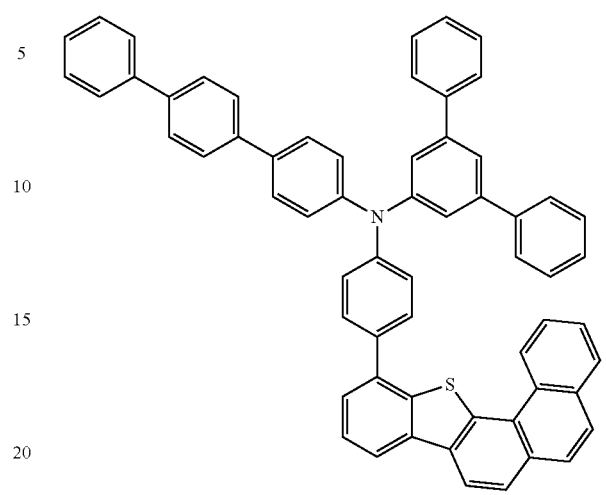
[CF B-85]
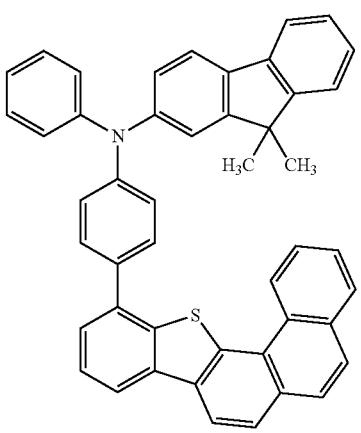
[CF B-86]
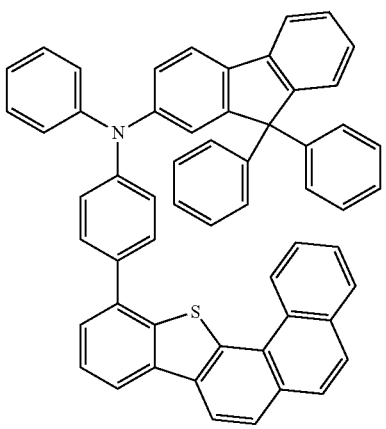

[CF B-87]
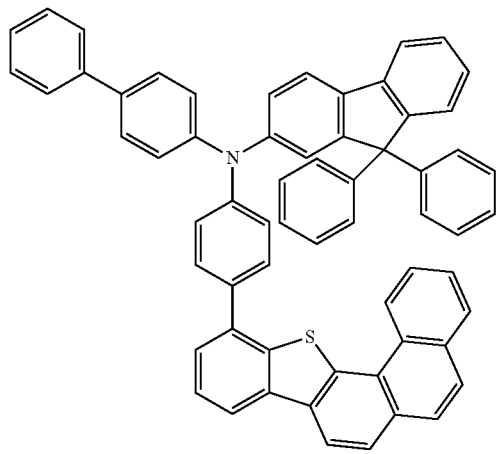
[CF B-90]
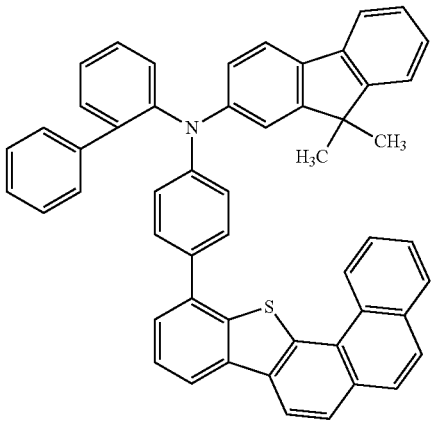
[CF B-88]
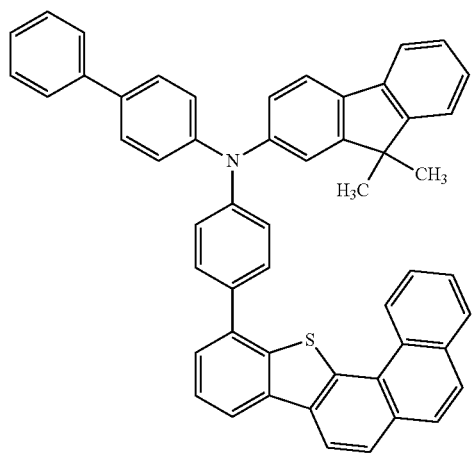
[CF B-91]
[CF B-89]
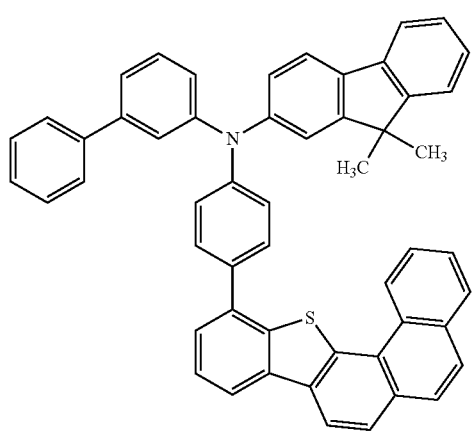
[CD B-92]
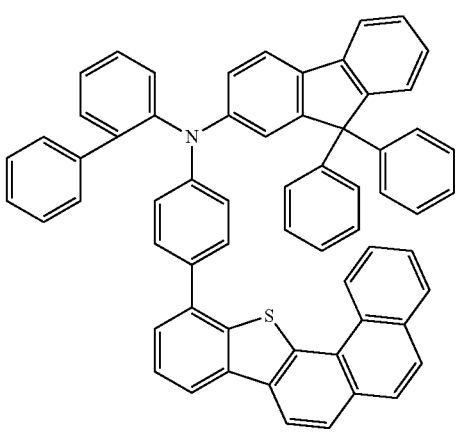

[CF B-93]
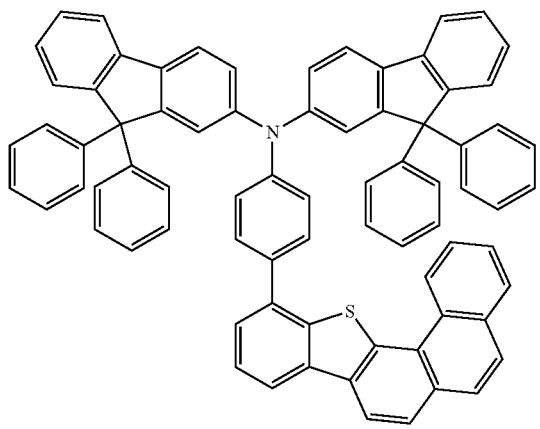
[CF C-1]
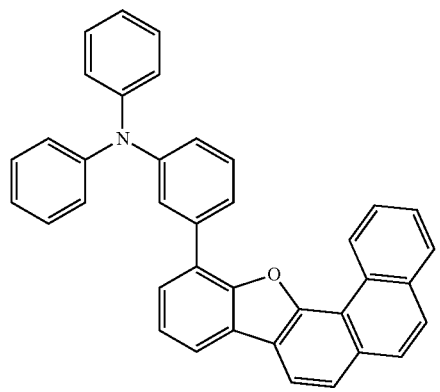
[CF C-2]
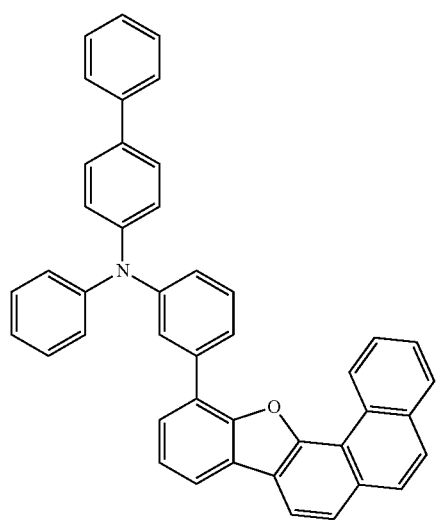
[CF C-3]
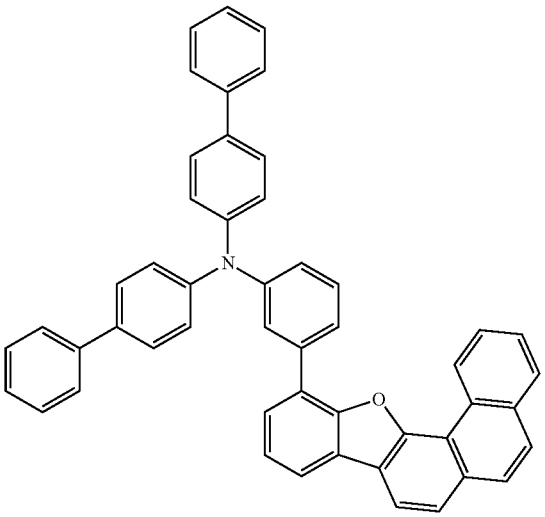
[CF C-4]
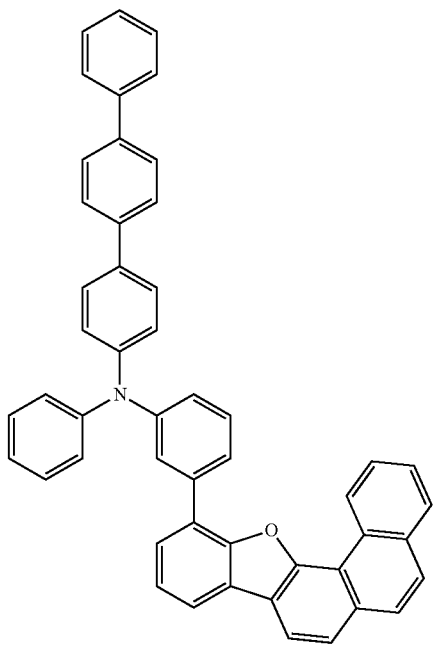

[CF C-5]
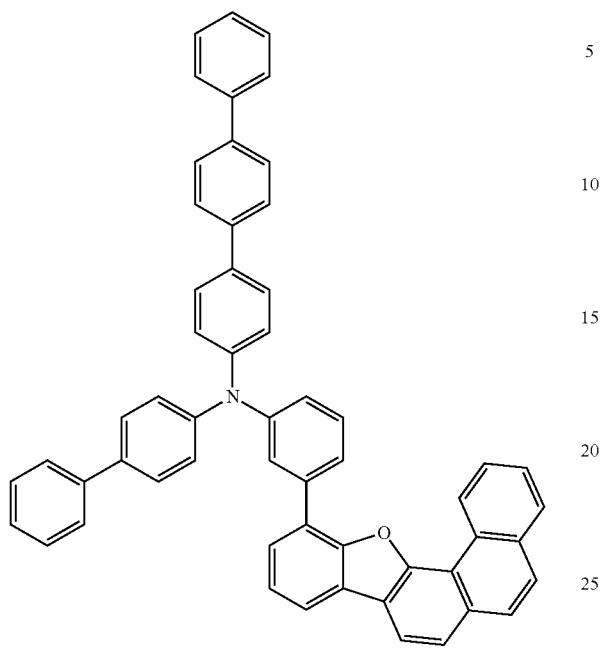
[CF C-6]
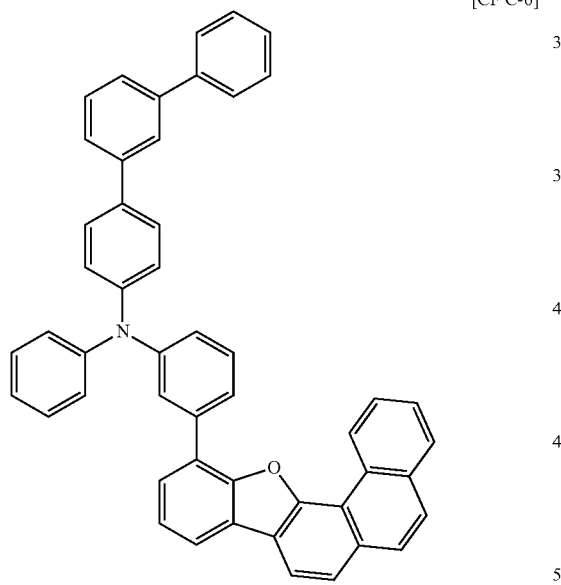
[CF C-7]
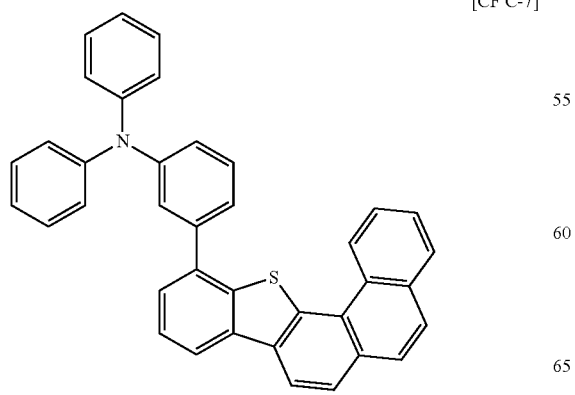
[CF C-8]
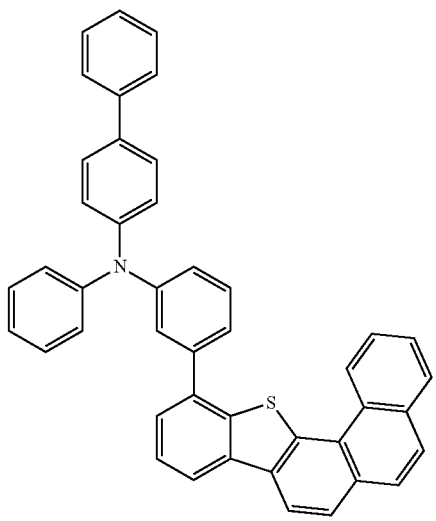
[CF C-9]
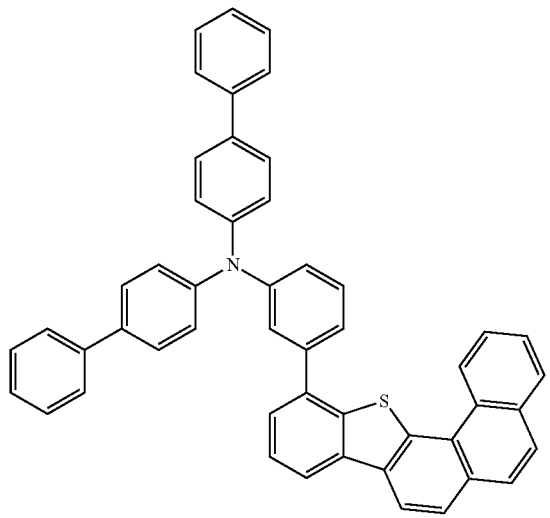

[CF C-10]
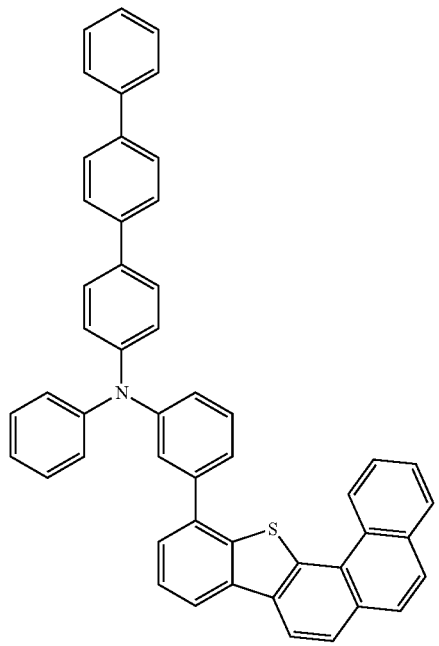
[CF C-11]
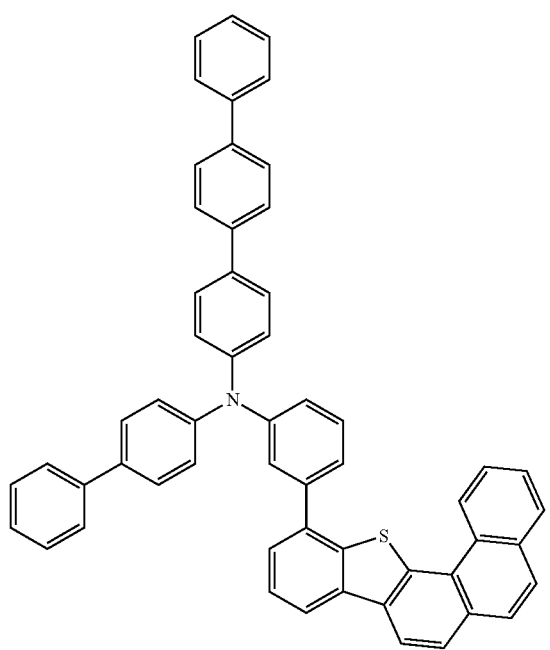
[CF C-12]
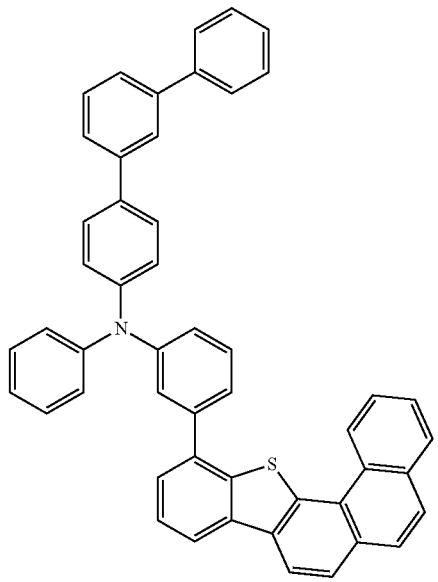
[CF D-1]
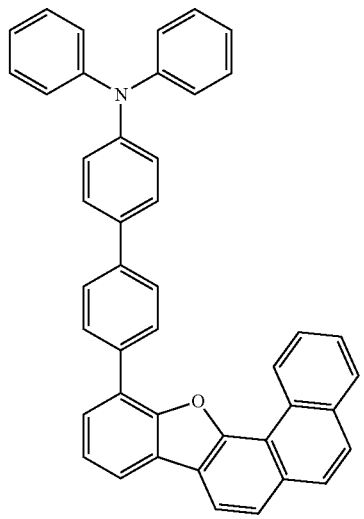

-continued
[CF D-2]
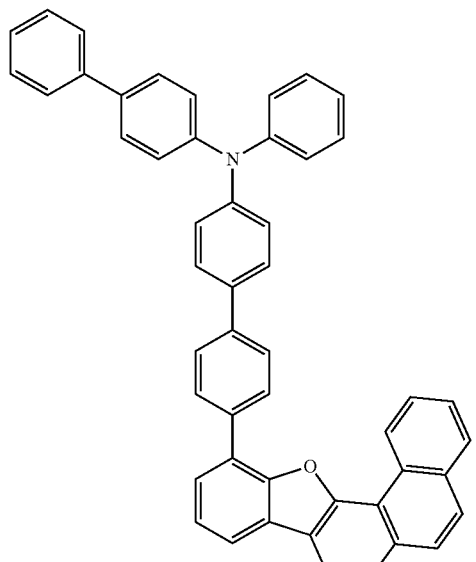
[CF D-4]
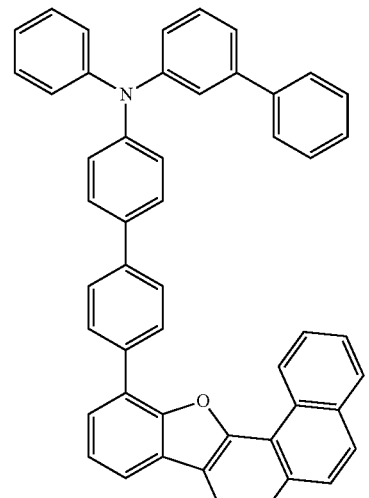
[CF D-3]
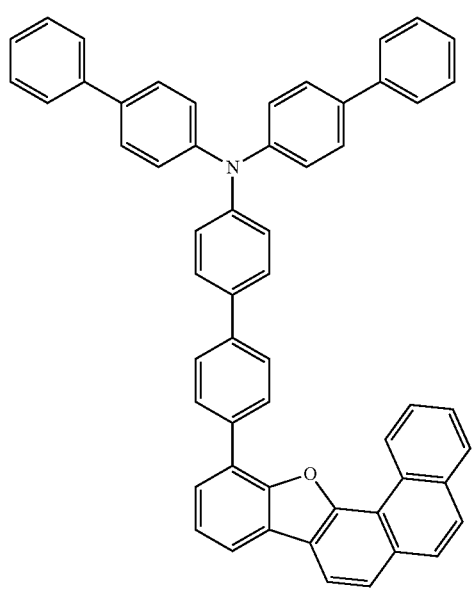

[CF D-7]
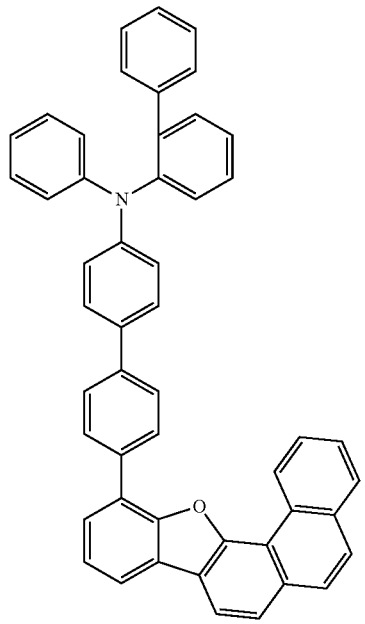
[CF D-9]
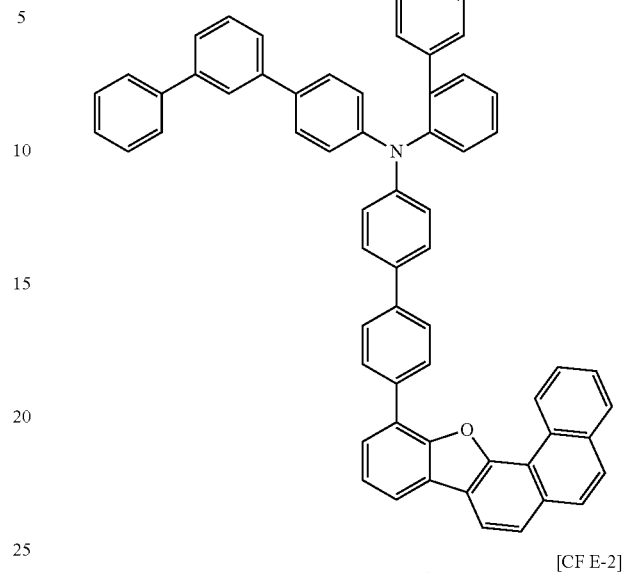
[CF E-2]
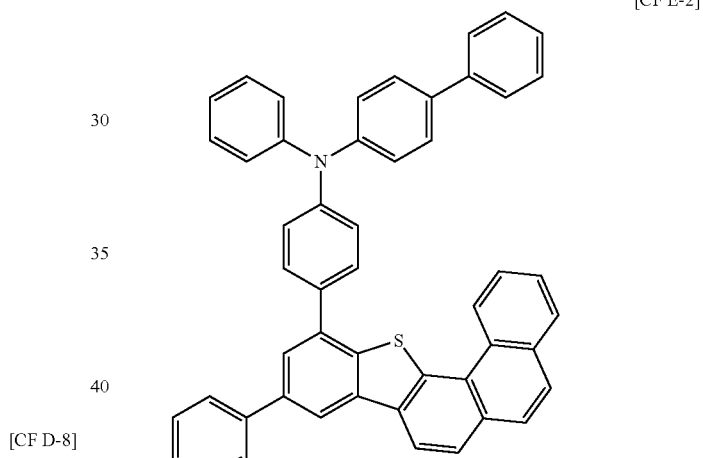
[CF D-8]
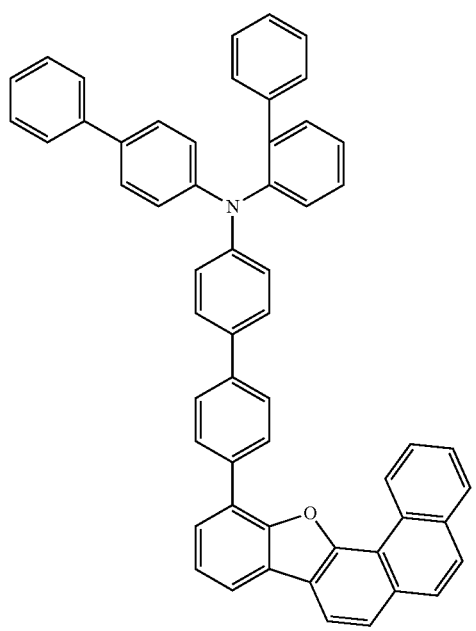
[CF E-3]
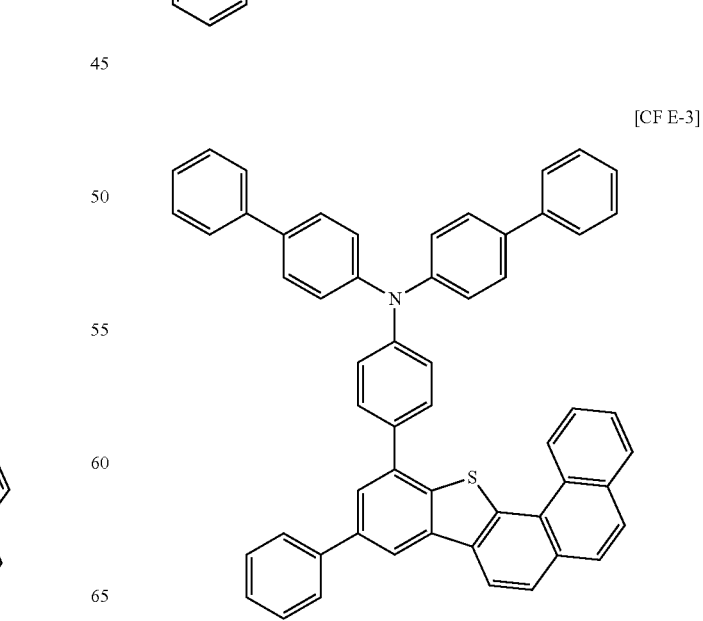

[CF E-5]
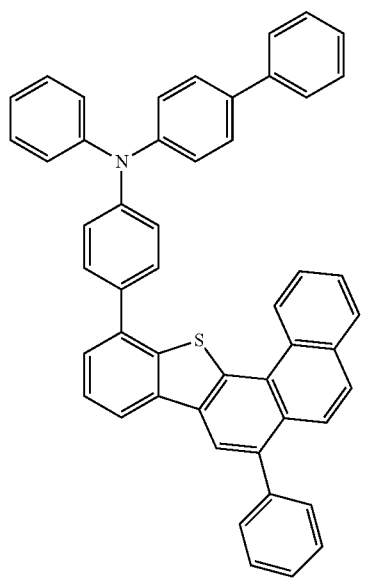
[CF E-6]
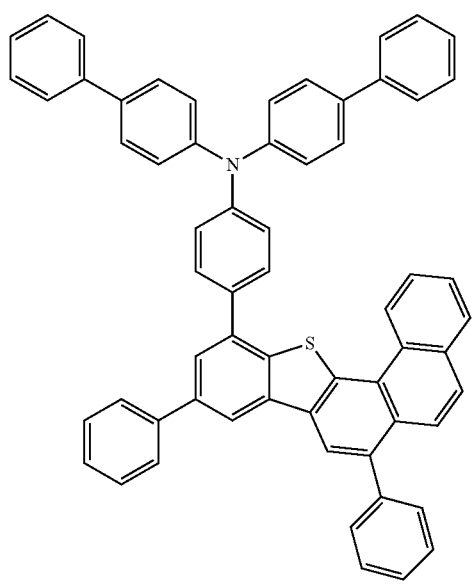
[CF E-7]
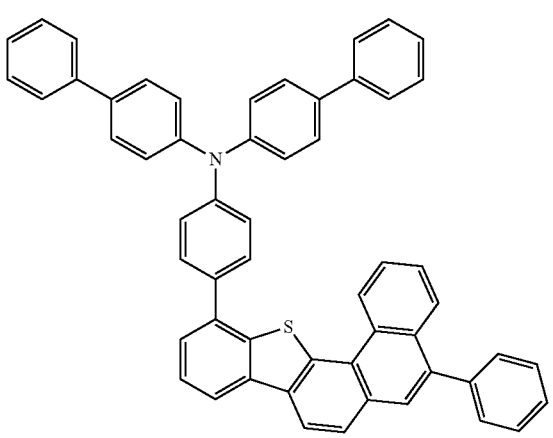
[CF E-8]
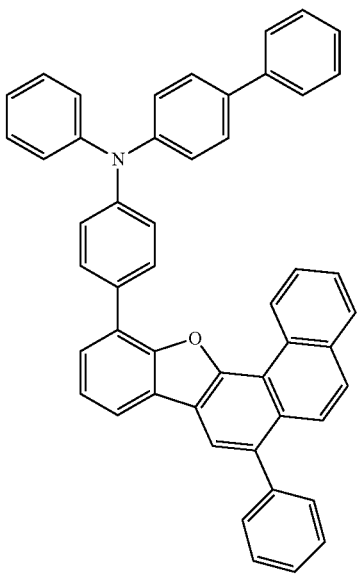
[CF E-9]
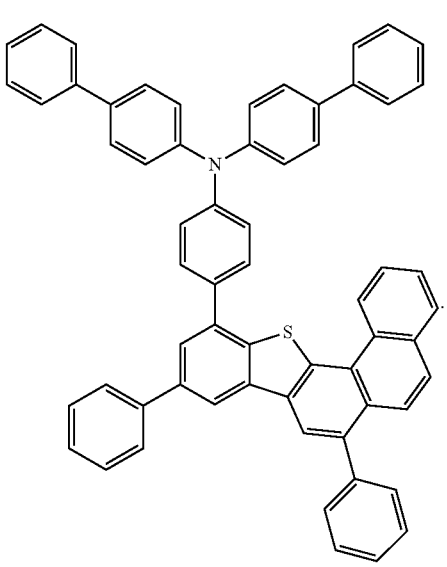
8. The organic optoelectric device of claim 1, wherein the first hole transport layer includes an organic compound represented by Chemical Formula 3:
[Chemical Formula 3]
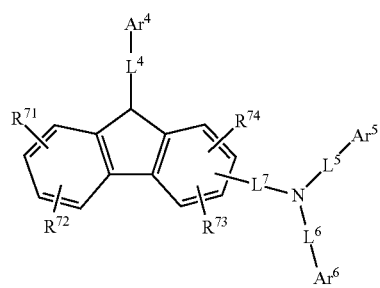
wherein, in Chemical Formula 3,
$R^{71}$ to $R^{74}$ are independently hydrogen, deuterium, a substituted or unsubstituted C1 to C10 alkyl group, a substituted or unsubstituted C6 to C30 aryl group, a substituted or unsubstituted C2 to C30 heterocyclic group, or a combination thereof, $R^{71}$ and $R^{72}$ are independently present or form a fused ring, $R^{73}$ and $R^{74}$ are independently present or form a fused ring, $Ar^4$ to $Ar^6$ are independently substituted or unsubstituted C6 to C30 aryl group or a substituted or unsubstituted C2 to C30 heterocyclic group, and $L^4$ to $L^7$ are independently a single bond, a substituted or unsubstituted C2 to C10 alkylene group, a substituted or unsubstituted C2 to C10 alkenylene group, a substituted or unsubstituted C2 to C10 alkynylene group, a substituted or unsubstituted C6 to C30 arylene group, a substituted or unsubstituted C2 to C30 heterocyclic group or a combination thereof.

9. The organic optoelectric device of claim 8, wherein $Ar^4$ of Chemical Formula 3 is a substituted or unsubstituted phenyl group or a substituted or unsubstituted biphenyl group, and $Ar^5$ and $Ar^6$ of Chemical Formula 3 are independently substituted or unsubstituted phenyl group, a substituted or unsubstituted biphenyl group, a substituted or unsubstituted fluorene group, a substituted or unsubstituted bisfluorene group, a substituted or unsubstituted triphenylene group, a substituted or unsubstituted anthracene group, a substituted or unsubstituted terphenyl group, a substituted or unsubstituted dibenzofuran group, or a substituted or unsubstituted dibenzothiophenyl group.

10. A display device comprising the organic optoelectric device of claim 1.

11. An organic optoelectric device, comprising:
an anode and a cathode facing each other, and
at least one organic layer between the anode and the cathode,
wherein the at least one organic layer includes:
an emission layer, and
a hole transport layer between the anode and the emission layer, the hole transport layer including a first hole transport layer adjacent to the anode and a second hole transport layer adjacent to the emission layer, wherein the second hole transport layer includes an organic compound represented by Chemical Formula 1:

[Chemical Formula 1]

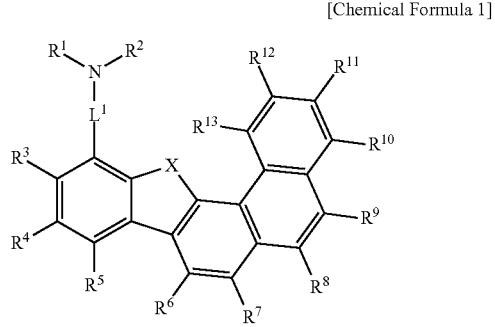

wherein, in Chemical Formula 1,

X is O or S, $L^1$ is a single bond, a substituted or unsubstituted C6 to C30 arylene group, or a substituted or unsubstituted C2 to C30 heterocyclic group, $R^1$ and $R^2$ are independently a substituted or unsubstituted C1 to C20 alkyl group, a substituted or unsubstituted C6 to C30 aryl group, a substituted or unsubstituted C2 to C30 heterocyclic group, a substituted or unsubstituted C3 to C40 silyl group, or a combination thereof, and $R^3$ to $R^{13}$ are independently hydrogen, deuterium, a halogen, a cyano group, a hydroxyl group, an amino group, a substituted or unsubstituted C1 to C20 amine group, a nitro group, a substituted or unsubstituted C1 to C20 alkyl group, a substituted or unsubstituted C6 to C30 aryl group, a substituted or unsubstituted C1 to C20 alkoxy group, a substituted or unsubstituted C6 to C20 aryloxy group, a substituted or unsubstituted C2 to C30 heterocyclic group, a substituted or unsubstituted C3 to C40 silyl group, or a combination thereof.

* * * * *